(12) United States Patent
Stierli et al.

(10) Patent No.: US 8,324,263 B2
(45) Date of Patent: Dec. 4, 2012

(54) MICROBIOCIDALLY ACTIVE CARBOXAMIDES

(75) Inventors: Daniel Stierli, Stein (CH); Antoine Daina, Geneva (CH); Harald Walter, Stein (CH); Ramya Rajan, Goa (IN); Hans Tobler, Basel (CH)

(73) Assignee: Syngenta Crop Protection, LLC, Greensboro, NC (US)

( * ) Notice: Subject to any disclaimer, the term of this patent is extended or adjusted under 35 U.S.C. 154(b) by 29 days.

(21) Appl. No.: 12/670,144

(22) PCT Filed: Jul. 24, 2008

(86) PCT No.: PCT/EP2008/006091
§ 371 (c)(1),
(2), (4) Date: Aug. 3, 2010

(87) PCT Pub. No.: WO2009/012998
PCT Pub. Date: Jan. 29, 2009

(65) Prior Publication Data
US 2010/0292239 A1 Nov. 18, 2010

(30) Foreign Application Priority Data

Jul. 26, 2007 (IN) .......................... 1581/DEL/2007
Sep. 3, 2007 (IN) .......................... 1867/DEL/2007

(51) Int. Cl.
*A01N 43/56* (2006.01)
*C07D 231/10* (2006.01)

(52) U.S. Cl. ............... 514/406; 514/407; 548/373.1; 548/374.1; 548/375.1

(58) Field of Classification Search ............. 514/406, 514/407; 548/373.1, 374.1, 375.1, 376.1
See application file for complete search history.

(56) References Cited

FOREIGN PATENT DOCUMENTS

| EP | 0405808 | 1/1991 |
|---|---|---|
| JP | 2003153668 | 7/1991 |
| JP | 2006056611 | 3/1994 |
| JP | 07089937 A * | 4/1995 |
| JP | 2007089937 | 4/1995 |
| JP | 2001342179 A * | 12/2001 |
| JP | 2001342180 | 12/2001 |
| JP | 2001342180 A * | 12/2001 |
| JP | 2001342183 | 12/2001 |
| JP | 20011342179 | 12/2001 |
| WO | 0191558 | 12/2001 |
| WO | 02051822 | 7/2002 |
| WO | 03004474 | 1/2003 |

* cited by examiner

*Primary Examiner* — Yong Chu
(74) *Attorney, Agent, or Firm* — R. Kody Jones

(57) ABSTRACT

Compounds of the formula (I), in which the substituents are as defined in claim 1 are suitable for use as microbiocides.

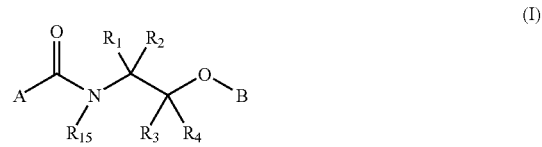

(I)

7 Claims, No Drawings

MICROBIOCIDALLY ACTIVE CARBOXAMIDES

This application is a 371 of International Application No. PCT/EP2008/006091 filed Jul. 24, 2008, which claims priority to IN 1581/DEL/2007 filed Jul. 26, 2007, and 1867/DEL/2007, filed Sep. 3, 2007, the contents of which are incorporated herein by reference.

The present invention relates to novel microbiocidally active, in particular fungicidally active, ethyloxy amides. It further relates to intermediates used in the preparation of these compounds, to compositions which comprise these compounds and to their use in agriculture or horticulture for controlling or preventing infestation of plants by phytopathogenic microorganisms, preferably fungi.

Similar compounds are also known in other fields of technology, for example, the use of aminoacetonitroles as insecticides is described in WO 03/004474.

It has been found that novel ethyloxy amides have microbiocidal activity. The present invention thus provides compounds of the formula I

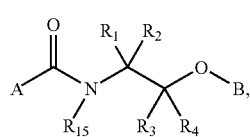

wherein
A is a 5-membered heterocyclic ring containing one to three heteroatoms, each independently selected from oxygen, nitrogen and sulphur, the heterocyclic ring being substituted by the groups $R_5$, $R_6$ and $R_7$;
$R_5$, $R_6$ and $R_7$ are each, independently, hydrogen, halogen, cyano, nitro, $C_1$-$C_4$alkyl, $C_1$-$C_4$halogenalkyl, $C_1$-$C_4$halogenalkoxy, $C_1$-$C_4$alkoxy($C_1$-$C_4$alkyl) or $C_1$-$C_4$halogenalkoxy($C_1$-$C_4$alkyl), provided that at least one of $R_5$, $R_6$ and $R_7$ is not hydrogen;
$R_1$, $R_2$, $R_3$ and $R_4$ independently of each other are hydrogen, halogen, $C_1$-$C_6$alkyl, $C_1$-$C_6$halogenalkyl, $C_3$-$C_6$cycloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, $C_1$-$C_6$halogenalkoxy, $C_1$-$C_6$alkylthio or $C_1$-$C_6$halogenalkylthio;
or $R_1$ and $R_2$ together are a $C_2$-$C_5$alkylene group, which is unsubstituted or substituted by one or more $C_1$-$C_6$alkyl groups;
or $R_1$ and $R_3$ together are a $C_1$-$C_5$alkylene group, which is unsubstituted or substituted by one or more $C_1$-$C_6$alkyl groups;
or $R_3$ and $R_4$ together are a $C_2$-$C_5$alkylene group, which is unsubstituted or substituted by one or more $C_1$-$C_6$alkyl groups;
$R_{15}$ is hydrogen or $C_3$-$C_7$cycloalkyl;
B is phenyl, naphthyl or a 5- to 10-membered heteroaromatic ring system containing one to three heteroatoms, each independently selected from oxygen, nitrogen and sulphur, the phenyl, naphthyl or 5- to 10-membered heteroaromatic ring system being substituted by one or more substituents $R_8$;
each substituent $R_8$ independently of each other is halogen, $C_1$-$C_6$alkoxy, —C(O)H, $C_1$-$C_6$alkylcarbonyl, amino, $C_1$-$C_6$alkylamino, di-$C_1$-$C_6$alkyl-amino, $C_1$-$C_6$alkylcarbonylamino, $C_1$-$C_6$haloalkoxy, $C_1$-$C_6$haloalkylthio, cyano, nitro, —C($R^a$)=N(O$R^b$), —N=C($R^e$)—N($R^f$)$_2$, $C_1$-$C_6$alkyl, which is unsubstituted or substituted by one or more substituents $R_9$, $C_2$-$C_6$alkenyl, which is unsubstituted or substituted by one or more substituents $R_9$, $C_2$-$C_6$alkynyl, which is unsubstituted or substituted by one or more substituents $R_9$, $C_2$-$C_6$alkenyloxy, which is unsubstituted or substituted by one or more substituents $R_9$, $C_3$-$C_6$cycloalkyl, which is unsubstituted or substituted by one or more substituents $R_9$, $C_6$-$C_{14}$bicycloalkyl, which is unsubstituted or substituted by one or more substituents $R_9$, phenyl, which is unsubstituted or substituted by one or more substituents $R_9$, or phenyloxy, which is unsubstituted or substituted by one or more substituents $R_9$;
each $R_9$ is independently of each other halogen, nitro, $C_3$-$C_6$cycloalkyl, $C_1$-$C_6$alkoxy, $C_1$-$C_6$halogenalkoxy, $C_1$-$C_6$alkylthio, $C_1$-$C_6$halogenalkylthio, $C_3$-$C_6$alkenyloxy, $C_3$-$C_6$alkynyloxy, phenyl, halophenyl, tri-$C_1$-$C_6$alkyl-silyl or —C($R^c$)=N(O$R^d$);
each $R^a$, $R^c$, $R^e$ and $R^f$ is independently of each other hydrogen or $C_1$-$C_6$alkyl;
each $R^b$ and $R^d$ is independently of each other $C_1$-$C_6$alkyl;
and tautomers/isomers/enantiomers of these compounds.

The alkyl groups occurring in the definitions of the substituents can be straight-chain or branched and are, for example, methyl, ethyl, n-propyl, n-butyl, n-pentyl, n-hexyl, iso-propyl, n-butyl, sec-butyl, iso-butyl or tent-butyl. Alkoxy, alkenyl and alkynyl radicals are derived from the alkyl radicals mentioned. The alkenyl and alkynyl groups can be mono- or di-unsaturated.

In the context of the present invention "substituted by one or more substituents" in the definition of the substituents, means typically, depending on the chemical structure of the substituents, monosubstituted to seven-times substituted, preferably monosubstituted to five-times substituted, more preferably mono-, double- or triple-substituted.

The cycloalkyl groups occurring in the definitions of the substituents are, for example, cyclopropyl, cyclobutyl, cyclopentyl or cyclohexyl.

Halogen is generally fluorine, chlorine, bromine or iodine, preferably fluorine, bromine or chlorine. This also applies, correspondingly, to halogen in combination with other meanings, such as halogenalkyl or halogenalkoxy.

Halogenalkyl groups preferably have a chain length of from 1 to 4 carbon atoms. Halogenalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Alkoxy is, for example, methoxy, ethoxy, propoxy, i-propoxy, n-butoxy, isobutoxy, sec-butoxy and tert-butoxy; preferably methoxy and ethoxy. Halogenalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Halogenphenyl is preferably phenyl substituted by 1, 2 or 3 halogen atoms, for example 4-chloro-phenyl.

$R_{15}$ as $C_3$-$C_7$cycloalkyl is cyclopropyl, cyclobutyl, cyclopentyl, cyclohexyl or cycloheptyl, preferably cyclopropyl.

In the context of the present invention a "5- or 6-membered heterocyclic ring containing one to three heteroatoms, each independently selected from oxygen, nitrogen and sulphur" preferably means pyrazolyl (especially pyrazol-4-yl), thiazolyl (especially thiazol-5-yl), pyrrolyl (especially pyrrol-3- yl), 1,2,3 triazolyl, oxazolyl (especially oxazol-5-yl), pyridyl (especially pyrid-3-yl) or 2,3 dihydro-[1,4]oxathiinyl (especially 2,3 dihydro-[1,4]oxathiin-5-yl).

The compounds of formula I can occur in different isomeric forms; the invention covers all those isomers and mixtures thereof. The compounds of the formula I may occur in different tautomeric forms. For example, compounds of formula I, wherein $R_{15}$ is hydrogen, exist in the tautomeric forms $I_I$ and $I_{II}$:

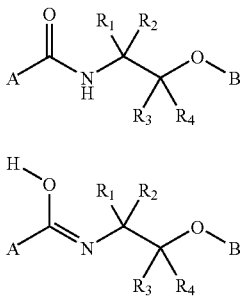

The invention covers all those tautomeric forms and mixtures thereof.

In a preferred group of compounds, A is $A_1$

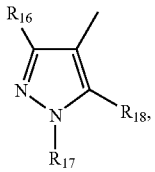

in which
$R_{16}$ is halogen, cyano, nitro, $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl;
$R_{17}$ is $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl; and
$R_{18}$ is hydrogen, halogen or cyano;
or A is $A_2$

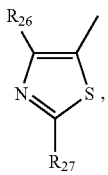

in which
$R_{26}$ is halogen, cyano, nitro, $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl; and
$R_{27}$ is $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl;
or A is $A_3$

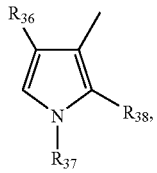

in which
$R_{36}$ is halogen, cyano, nitro, $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl;
$R_{37}$ is $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl; and
$R_{38}$ is hydrogen, halogen or cyano;
or A is $A_4$

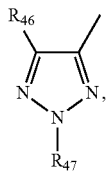

in which
$R_{46}$ and $R_{47}$ independently of one another are halogen, cyano, nitro, $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl.

Within said preferred group of compounds, further preferably A is $A_1$.

Within said preferred group of compounds, further preferably A is $A_2$.

Within said preferred group of compounds, further preferably A is $A_3$.

Within said preferred group of compounds, further preferably A is $A_4$.

In a particular preferred group of compounds A is $A_1$, wherein $R_{18}$ is hydrogen. In another particular preferred group of compounds A is $A_1$, wherein $R_{16}$ is $C_1$-$C_4$alkyl or $C_1$-$C_4$halogenalkyl, preferably $C_1$-$C_4$halogenalkyl; even more preferably $R_{16}$ is selected from $CF_2H$ and $CF_3$, $R_{17}$ is $C_1$-$C_4$alkyl; preferably methyl; and $R_{18}$ is hydrogen or halogen, preferably hydrogen. In one embodiment, $R_{16}$ is $CF_2H$, $R_{17}$ is methyl and $R_{18}$ is hydrogen. In another particular preferred group of compounds A is $A_2$, wherein $R_{26}$ is $C_1$-$C_4$alkyl or $C_1$-$C_4$halogenalkyl; and $R_{27}$ is $C_1$-$C_4$alkyl.

In yet another particular preferred group of compounds A is $A_3$, wherein $R_{36}$ is $C_1$-$C_4$alkyl or $C_1$-$C_4$halogenalkyl; $R_{37}$ is $C_1$-$C_4$alkyl; and $R_{38}$ is hydrogen or halogen.

In yet another particular preferred group of compounds A is $A_4$, wherein $R_{46}$ is $C_1$-$C_4$alkyl or $C_1$-$C_4$halogenalkyl; and $R_{47}$ is $C_1$-$C_4$alkyl.

In yet another particular preferred group of compounds A is A$_4$, wherein R$_{46}$ halogenmethyl, preferably R$_{46}$ is selected from CF$_3$, CF$_2$H and CFH$_2$; and R$_{47}$ is C$_1$-C$_4$alkyl.

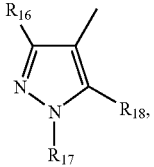
(A$_1$)

in which

R$_{16}$ is halogen, cyano, nitro, C$_1$-C$_4$alkyl, C$_1$-C$_4$halogenalkyl, C$_1$-C$_4$halogenalkoxy, C$_1$-C$_4$alkoxy-C$_1$-C$_4$alkyl or C$_1$-C$_4$halogenalkoxy-C$_1$-C$_4$alkyl;

R$_{17}$ is C$_1$-C$_4$alkyl, C$_1$-C$_4$halogenalkyl, C$_1$-C$_4$halogenalkoxy, C$_1$-C$_4$alkoxy-C$_1$-C$_4$alkyl or C$_1$-C$_4$halogenalkoxy-C$_1$-C$_4$alkyl; and R$_{18}$ is hydrogen, halogen or cyano;

or A is A$_2$

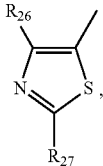
(A$_2$)

in which

R$_{26}$ is halogen, cyano, nitro, C$_1$-C$_4$alkyl, C$_1$-C$_4$halogenalkyl, C$_1$-C$_4$halogenalkoxy, C$_1$-C$_4$alkoxy-C$_1$-C$_4$alkyl or C$_1$-C$_4$halogenalkoxy-C$_1$-C$_4$alkyl; and R$_{27}$ is C$_1$-C$_4$alkyl, C$_1$-C$_4$halogenalkyl, C$_1$-C$_4$halogenalkoxy, C$_1$-C$_4$alkoxy-C$_1$-C$_4$alkyl or C$_1$-C$_4$halogenalkoxy-C$_1$-C$_4$alkyl;

or A is A$_3$

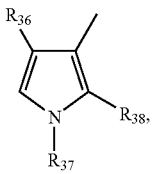
(A$_3$)

in which

R$_{36}$ is halogen, cyano, nitro, C$_1$-C$_4$alkyl, C$_1$-C$_4$halogenalkyl, C$_1$-C$_4$halogenalkoxy, C$_1$-C$_4$alkoxy-C$_1$-C$_4$alkyl or C$_1$-C$_4$halogenalkoxy-C$_1$-C$_4$alkyl;

R$_{37}$ is C$_1$-C$_4$alkyl, C$_1$-C$_4$halogenalkyl, C$_1$-C$_4$halogenalkoxy, C$_1$-C$_4$alkoxy-C$_1$-C$_4$alkyl or C$_1$-C$_4$halogenalkoxy-C$_1$-C$_4$alkyl; and R$_{38}$ is hydrogen, halogen or cyano;

or A is A$_4$

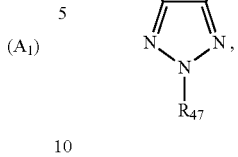
(A$_4$)

in which

R$_{46}$ and R$_{47}$ independently of one another are halogen, cyano, nitro, C$_1$-C$_4$alkyl, C$_1$-C$_4$halogenalkyl, C$_1$-C$_4$halogenalkoxy, C$_1$-C$_4$alkoxy-C$_1$-C$_4$alkyl or C$_1$-C$_4$halogenalkoxy-C$_1$-C$_4$alkyl.

In a preferred group of compounds, R$_1$, R$_2$, R$_3$ and R$_4$ independently of each other are hydrogen or C$_1$-C$_6$alkyl; or R$_1$ and R$_2$ together are a C$_2$-C$_5$alkylene group; or R$_1$ and R$_3$ together are a C$_1$-C$_5$alkylene group; or R$_3$ and R$_4$ together are a C$_2$-C$_5$alkylene group.

In a further preferred group of compounds, R$_1$, R$_2$, R$_3$ and R$_4$ independently of each other are hydrogen or C$_1$-C$_6$alkyl; more preferably R$_1$ and R$_2$ independently of each other are C$_1$-C$_6$alkyl; and R$_2$ and R$_4$ are each hydrogen. In a yet further preferred group of compounds, R$_1$ stands for C$_1$-C$_6$alkyl, preferably methyl; and R$_2$, R$_3$ and R$_4$ are each hydrogen.

In another further preferred group of compounds, R$_1$ and R$_2$ together are a C$_2$-C$_5$alkylene group, preferably ethylene; and R$_3$ and R$_4$ are both hydrogen.

In another further preferred group of compounds, R$_1$ and R$_3$ together are a C$_1$-C$_5$alkylene group, preferably methylene; and R$_2$ and R$_4$ are both hydrogen.

In another further preferred group of compounds, R$_1$, R$_2$, R$_3$ and R$_4$ are all hydrogen.

Preferably R$_{15}$ is hydrogen.

In a preferred group of compounds, B is phenyl, naphthyl or a 5-, 6-, 9- or 10-membered heteroaromatic ring system containing one to three heteroatoms, each independently selected from oxygen, nitrogen and sulphur, the phenyl, naphthyl or 5-, 6-, 9- or 10-membered heteroaromatic ring system being substituted by one or more substituents R$_8$;

In a preferred group of compounds, B is selected from the following groups:

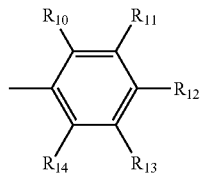
B$_1$

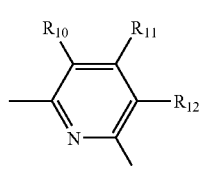
B$_2$

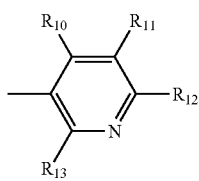 B₃
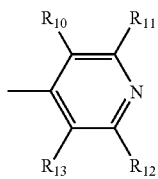 B₄
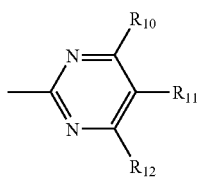 B₅
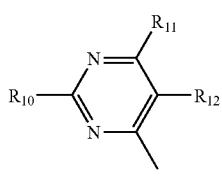 B₆
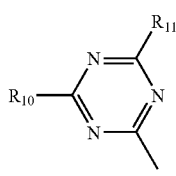 B₇
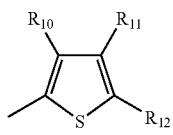 B₈
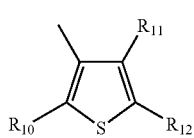 B₉
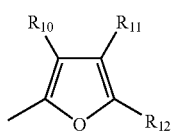 B₁₀
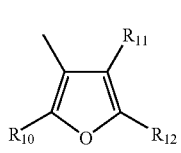 B₁₁
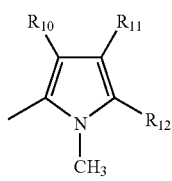 B₁₂
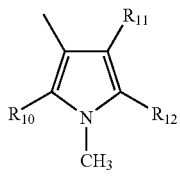 B₁₃
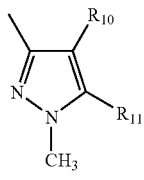 B₁₄
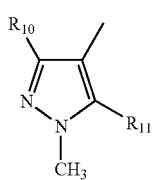 B₁₅
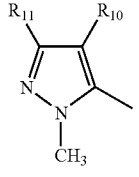 B₁₆
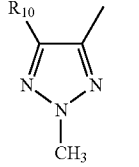 B₁₇
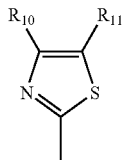 B₁₈
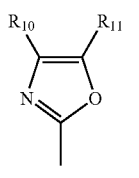 B₁₉

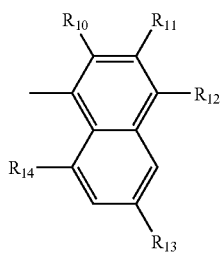

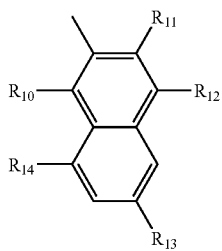

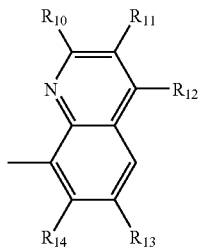

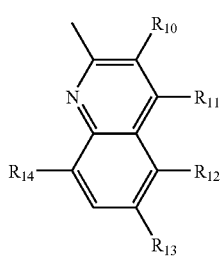

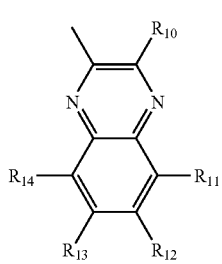

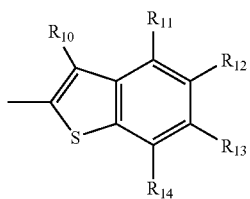

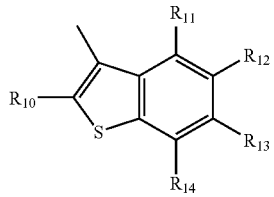

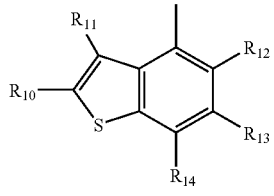

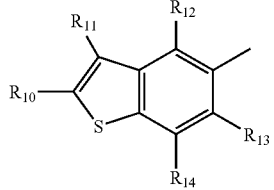

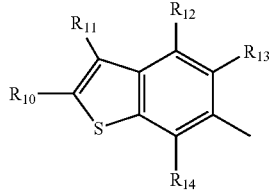

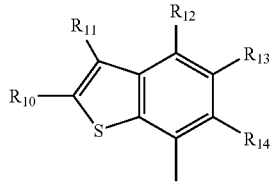

in which $R_{10}$, $R_{11}$, $R_{12}$, $R_{13}$ and $R_{14}$ each independently of each other stands for hydrogen, halogen, $C_1$-$C_6$alkoxy, —C(O)H, $C_1$-$C_6$alkylcarbonyl, amino, $C_1$-$C_6$alkylamino, di-$C_1$-$C_6$alkyl-amino, $C_1$-$C_6$alkylcarbonylamino, $C_1$-$C_6$haloalkoxy, $C_1$-$C_6$haloalkylthio, cyano, nitro, —C($R^a$)=N(O$R^b$), —N=C($R^e$)—N($R^f$)$_2$, $C_1$-$C_6$alkyl, which is unsubstituted or substituted by one or more substituents $R_9$, $C_2$-$C_6$alkenyl, which is unsubstituted or substituted by one or more substituents $R_9$, $C_2$-$C_6$alkynyl, which is unsubstituted or substituted by one or more substituents $R_9$, $C_2$-$C_6$alkenyloxy, which is unsubstituted or substituted by one or more substituents $R_9$, $C_3$-$C_6$cycloalkyl, which is unsubstituted or substituted by one or more substituents $R_9$, $C_6$-$C_{14}$bicycloalkyl, which is unsubstituted or substituted by one or more substituents $R_9$, phenyl, which is unsubstituted or substituted by one or more substituents $R_9$, or phenyloxy, which is unsubstituted or substituted by one or more substituents $R_9$;

each $R_9$ is independently of each other halogen, nitro, $C_3$-$C_6$cycloalkyl, $C_1$-$C_6$alkoxy, $C_1$-$C_6$halogenalkoxy, $C_1$-$C_6$alkylthio, $C_1$-$C_6$halogenalkylthio, $C_3$-$C_6$alkenyloxy, $C_3$-$C_6$alkynyloxy, phenyl, halophenyl, tri-$C_1$-$C_6$alkyl-silyl or —C($R^c$)=N(O$R^d$);

each $R^a$, $R^c$, $R^e$ and $R^f$ is independently of each other hydrogen or $C_1$-$C_6$alkyl;

each $R^b$ and $R^d$ is independently of each other $C_1$-$C_6$alkyl;

provided that at least one of $R_{10}$, $R_{11}$, $R_{12}$, $R_{13}$ and $R_{14}$ is not hydrogen.

Preferably, $R_{10}$, $R_{11}$, $R_{12}$, $R_{13}$ and $R_{14}$ each independently of each other stands for hydrogen, halogen, $C_1$-$C_6$alkoxy, $C_1$-$C_6$haloalkoxy, $C_1$-$C_6$haloalkylthio, —C($R^a$)=N(O$R^b$), $C_1$-$C_6$alkyl, which is unsubstituted or substituted by one or more substituents $R_9$, $C_2$-$C_6$alkenyl, which is unsubstituted or substituted by one or more substituents $R_9$, $C_2$-$C_6$alkynyl, which is unsubstituted or substituted by one or more substituents $R_9$, phenyl, which is unsubstituted or substituted by one or more substituents $R_9$; and each $R_9$ is independently of each other halogen or $C_1$-$C_6$alkoxy; provided that at least one of $R_{10}$, $R_{11}$, $R_{12}$, $R_{13}$ and $R_{14}$ is not hydrogen.

More preferably, $R_{10}$, $R_{11}$, $R_{12}$, $R_{13}$ and $R_{14}$ each independently of each other stands for hydrogen, halogen, $C_1$-$C_6$alkyl or $C_1$-$C_6$haloalkyl; provided that at least one of $R_{10}$, $R_{11}$, $R_{12}$, $R_{13}$ and $R_{14}$ is not hydrogen.

In a preferred group of compounds, B is selected from $B_1$, $B_2$, $B_3$, $B_4$, $B_{20}$, $B_{21}$, $B_{22}$, $B_{23}$, $B_{24}$, $B_{25}$, $B_{26}$, $B_{27}$, $B_{28}$, $B_{29}$ and $B_{30}$. More preferably, B is selected from $B_1$, $B_2$, $B_3$, $B_4$, $B_{20}$, $B_{21}$, $B_{22}$, $B_{23}$ and $B_{24}$. Even more preferably, B is $B_1$, $B_2$, $B_3$ or $B_4$. In one embodiment B is $B_1$.

In another embodiment B is $B_2$, $B_3$ or $B_4$. In yet another embodiment B is $B_2$. In yet another embodiment B is $B_3$. In yet another embodiment B is $B_4$.

In yet another embodiment B is $B_{20}$, $B_{21}$, $B_{22}$, $B_{23}$ or $B_{24}$. In yet another embodiment B is $B_{20}$ or $B_{21}$. In yet another embodiment B is $B_{20}$. In yet another embodiment B is $B_{21}$.

In yet another embodiment B is $B_{22}$, $B_{23}$ or $B_{24}$. In yet another embodiment B is $B_{22}$.

In yet another embodiment B is $B_{23}$. In yet another embodiment B is $B_{24}$.

In yet another embodiment B is $B_{25}$, $B_{26}$, $B_{27}$, $B_{28}$, $B_{29}$ or $B_{30}$. In yet another embodiment B is $B_{25}$. In yet another embodiment B is $B_{26}$. In yet another embodiment B is $B_{27}$. In yet another embodiment B is $B_{28}$. In yet another embodiment B is $B_{29}$. In yet another embodiment B is $B_{30}$.

In a preferred group of compounds, B is $B_1$

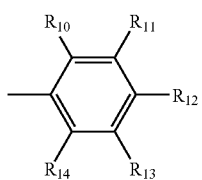

$B_1$ in which $R_{10}$, $R_{11}$, $R_{12}$, $R_{13}$ and $R_{14}$ each independently of each other stands for hydrogen, halogen, $C_1$-$C_6$alkoxy, —C(O)H, $C_1$-$C_6$alkylcarbonyl, amino, $C_1$-$C_6$alkylamino, di-$C_1$-$C_6$alkyl-amino, $C_1$-$C_6$alkylcarbonylamino, $C_1$-$C_6$haloalkoxy, $C_1$-$C_6$haloalkylthio, cyano, nitro, —C($R^a$)=N(O$R^b$), —N=C($R^e$)—N($R^f$)$_2$, $C_1$-$C_6$alkyl, which is unsubstituted or substituted by one or more substituents $R_9$, $C_2$-$C_6$alkenyl, which is unsubstituted or substituted by one or more substituents $R_9$, $C_2$-$C_6$alkynyl, which is unsubstituted or substituted by one or more substituents $R_9$, $C_2$-$C_6$alkenyloxy, which is unsubstituted or substituted by one or more substituents $R_9$, $C_3$-$C_6$cycloalkyl, which is unsubstituted or substituted by one or more substituents $R_9$, $C_6$-$C_{14}$bicycloalkyl, which is unsubstituted or substituted by one or more substituents $R_9$, phenyl, which is unsubstituted or substituted by one or more substituents $R_9$, or phenyloxy, which is unsubstituted or substituted by one or more substituents $R_9$;

each $R_9$ is independently of each other halogen, nitro, $C_3$-$C_6$cycloalkyl, $C_1$-$C_6$alkoxy, $C_1$-$C_6$halogenalkoxy, $C_1$-$C_6$alkylthio, $C_1$-$C_6$halogenalkylthio, $C_3$-$C_6$alkenyloxy, $C_3$-$C_6$alkynyloxy, phenyl, halophenyl, tri-$C_1$-$C_6$alkyl-silyl or —C($R^c$)=N(O$R^d$);

each $R^a$, $R^c$, $R^e$ and $R^f$ is independently of each other hydrogen or $C_1$-$C_6$alkyl;

each $R^b$ and $R^d$ is independently of each other $C_1$-$C_6$alkyl;

provided that at least one of $R_{10}$, $R_{11}$, $R_{12}$, $R_{13}$ and $R_{14}$ is not hydrogen.

In a preferred group of compounds, B is $B_1$, in which $R_{10}$, $R_{11}$, $R_{12}$, $R_{13}$ and $R_{14}$ each independently of each other stands for hydrogen, halogen, $C_1$-$C_6$alkoxy, $C_1$-$C_6$haloalkoxy, $C_1$-$C_6$haloalkylthio, —C($R^a$)=N(O$R^b$), $C_1$-$C_6$alkyl, which is unsubstituted or substituted by one or more substituents $R_9$, $C_2$-$C_6$alkenyl, which is unsubstituted or substituted by one or more substituents $R_9$, $C_2$-$C_6$alkynyl, which is unsubstituted or substituted by one or more substituents $R_9$, phenyl, which is unsubstituted or substituted by one or more substituents $R_9$; phenyloxy, which is unsubstituted or substituted by one or more substituents $R_9$; and each $R_9$ is independently of each other halogen or $C_1$-$C_6$alkoxy;

provided that at least one of $R_{10}$, $R_{11}$, $R_{12}$, $R_{13}$ and $R_{14}$ is not hydrogen.

In a further preferred group of compounds, B is $B_{1A}$

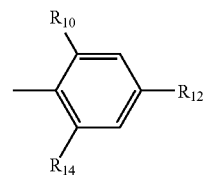

$B_{1A}$ in which $R_{10}$, $R_{12}$ and $R_{14}$ each independently of each other stands for hydrogen, halogen, $C_1$-$C_6$alkoxy, $C_1$-$C_6$haloalkoxy, $C_1$-$C_6$haloalkylthio, —C($R^a$)=N(O$R^b$), $C_1$-$C_6$alkyl, which is unsubstituted or substituted by one or more substituents $R_9$, $C_2$-$C_6$alkenyl, which is unsubstituted or substituted by one or more substituents $R_9$, $C_2$-$C_6$alkynyl, which is unsubstituted or substituted by one or more substituents $R_9$, phenyl, which is unsubstituted or substituted by one or more substituents $R_9$; phenyloxy, which is unsubstituted or substituted by one or more substituents $R_9$; and each $R_9$ is independently of each other halogen or $C_1$-$C_6$alkoxy; provided that at least one of $R_{10}$, $R_{12}$ and $R_{14}$ is not hydrogen.

Further preferred are compounds, wherein B is $B_{1A}$, in which $R_{10}$, $R_{12}$ and $R_{14}$ each independently of each other stands for hydrogen, halogen, $C_1$-$C_6$alkyl or $C_1$-$C_6$haloalkyl; provided that at least one of $R_{10}$, $R_{12}$ and $R_{14}$ is not hydrogen.

In one embodiment, $R_{10}$ and $R_{12}$ each independently of each other stands for halogen, $C_1$-$C_6$alkyl or $C_1$-$C_6$haloalkyl; and $R_{14}$ stands for hydrogen, halogen, $C_1$-$C_6$alkyl or $C_1$-$C_6$haloalkyl.

In a further embodiment, $R_{10}$ and $R_{12}$ each independently of each other stands for halogen, $C_1$-$C_6$alkyl or $C_1$-$C_6$haloalkyl; and $R_{14}$ stands for hydrogen.

In yet a further embodiment, $R_{10}$, $R_{12}$ and $R_{14}$ each independently of each other stands for halogen, $C_1$-$C_6$alkyl or $C_1$-$C_6$haloalkyl.

In yet a further embodiment, $R_{10}$ and $R_{14}$ each independently of each other stands for halogen, $C_1$-$C_6$alkyl or $C_1$-$C_6$haloalkyl; and $R_{12}$ stands for hydrogen, halogen, $C_1$-$C_6$alkyl or $C_1$-$C_6$haloalkyl.

In yet a further embodiment, $R_{10}$ and $R_{14}$ each independently of each other stands for halogen, $C_1$-$C_6$alkyl or $C_1$-$C_6$haloalkyl; and $R_{12}$ stands for hydrogen.

In yet a further embodiment, $R_{10}$ stands for halogen, $C_1$-$C_6$alkyl or $C_1$-$C_6$haloalkyl; and $R_{12}$ and $R_{14}$ both are hydrogen.

In yet a further embodiment, $R_{12}$ stands for halogen, $C_1$-$C_6$alkyl or $C_1$-$C_6$haloalkyl; and $R_{10}$ and $R_{14}$ both are hydrogen.

In a further preferred group of compounds, B is $B_{1B}$

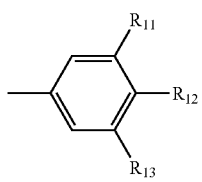

$B_{1B}$ in which $R_{11}$, $R_{12}$ and $R_{13}$ each independently of each other stands for hydrogen, halogen, $C_1$-$C_6$alkoxy, $C_1$-$C_6$haloalkoxy, $C_1$-$C_6$haloalkylthio, —C($R^a$)=N(O$R^b$), $C_1$-$C_6$alkyl, which is unsubstituted or substituted by one or more substituents $R_9$, $C_2$-$C_6$alkenyl, which is unsubstituted or substituted by one or more substituents $R_9$, $C_2$-$C_6$alkynyl, which is unsubstituted or substituted by one or more substituents $R_9$, phenyl, which is unsubstituted or substituted by one or more substituents $R_9$; phenyloxy, which is unsubstituted or substituted by one or more substituents $R_9$; and each $R_9$ is independently of each other halogen or $C_1$-$C_6$alkoxy; provided that at least one of $R_{11}$, $R_{12}$ and $R_{13}$ is not hydrogen.

Further preferred are compounds, wherein B is $B_{1B}$, in which $R_{11}$, $R_{12}$ and $R_{13}$ each independently of each other stands for hydrogen, halogen, $C_1$-$C_6$alkyl or $C_1$-$C_6$haloalkyl; provided that at least one of $R_{11}$, $R_{12}$ and $R_{13}$ is not hydrogen.

In one embodiment, $R_{11}$ and $R_{13}$ each independently of each other stands for halogen, $C_1$-$C_6$alkyl or $C_1$-$C_6$haloalkyl; and $R_{12}$ stands for hydrogen, halogen, $C_1$-$C_6$alkyl or $C_1$-$C_6$haloalkyl.

In a further embodiment, $R_{11}$ and $R_{13}$ each independently of each other stands for halogen, $C_1$-$C_6$alkyl or $C_1$-$C_6$haloalkyl; and $R_{12}$ stands for hydrogen.

In a further embodiment, $R_{11}$ and $R_{12}$ each independently of each other stands for halogen, $C_1$-$C_6$alkyl or $C_1$-$C_6$haloalkyl; and $R_{13}$ stands for hydrogen.

In a further embodiment, $R_{11}$, $R_{12}$ and $R_{13}$ each independently of each other stands for halogen, $C_1$-$C_6$alkyl or $C_1$-$C_6$haloalkyl.

If $R_1$ is different from $R_2$, the S-enantiomer is preferred.

The preparation of the compounds of formula I wherein $R_{15}$ is hydrogen is described below. The compounds of formula I, wherein $R_{15}$ is $C_3$-$C_7$cycloalkyl can be prepared analogously.

Compounds of formula I may be prepared by reacting a compound of formula II

(II)

in which B, $R_1$, $R_2$, $R_3$ and $R_4$ are as defined under formula I; with a compound of formula III

A—C(=O)—R*       (III), in which A is as defined under formula I, and R* is halogen, hydroxy or $C_{1-6}$ alkoxy, preferably chloro, in the presence of a base, such as triethylamine, Hunig base, sodium bicarbonate, sodium carbonate, potassium carbonate, pyridine or quinoline, but preferably triethylamine, and in a solvent, such as diethylether, TBME, THF, dichloromethane, chloroform, DMF or NMP, for between 10 minutes and 48 hours, preferably 12 to 24 hours, and between 0° C. and reflux, preferably 20 to 25° C.

When R* is hydroxy, a coupling agent, such as benzotriazol-1-yloxytris(dimethylamino)phosphoniumhexafluorophosphate, bis-(2-oxo-3-oxazolidinyl)-phosphinic acid chloride (BOP-Cl), N,N'-dicyclohexylcarbodiimide (DCC) or 1,1'-carbonyl-diimidazole (CDI), may be used.

Intermediates of the formula II, in which B, $R_1$, $R_2$, $R_3$ and $R_4$ are as defined under formula I; may be prepared according to the following reaction schemes (schemes 1 to 5) or in analogy to those reaction schemes.

Intermediates of formula IIb

(IIb)

in which B is as defined under formula I and $R_1$, $R_3$ and $R_4$ independently of each other are hydrogen, $C_1$-$C_6$ alkyl, $C_1$-$C_6$ halogenalkyl, $C_3$-$C_6$ cycloalkyl, $C_2$-$C_6$ alkenyl, $C_2$-$C_6$ haloalkenyl, $C_2$-$C_6$alkynyl, $C_2$-$C_6$ haloalkynyl, $C_1$-$C_6$ alkoxy, $C_1$-$C_6$ halogenalkoxy, $C_1$-$C_6$ alkylthio or $C_1$-$C_6$ halogenalkylthio; or $R_1$ and $R_3$ together are a $C_2$-$C_5$alkylene group, which is unsubstituted or substituted by one or more $C_1$-$C_6$alkyl groups; or $R_3$ and $R_4$ together are a $C_2$-$C_5$alkylene group, which is unsubstituted or substituted by one or more $C_1$-$C_6$alkyl groups; may be prepared as described in reaction scheme 1.

Scheme 1:
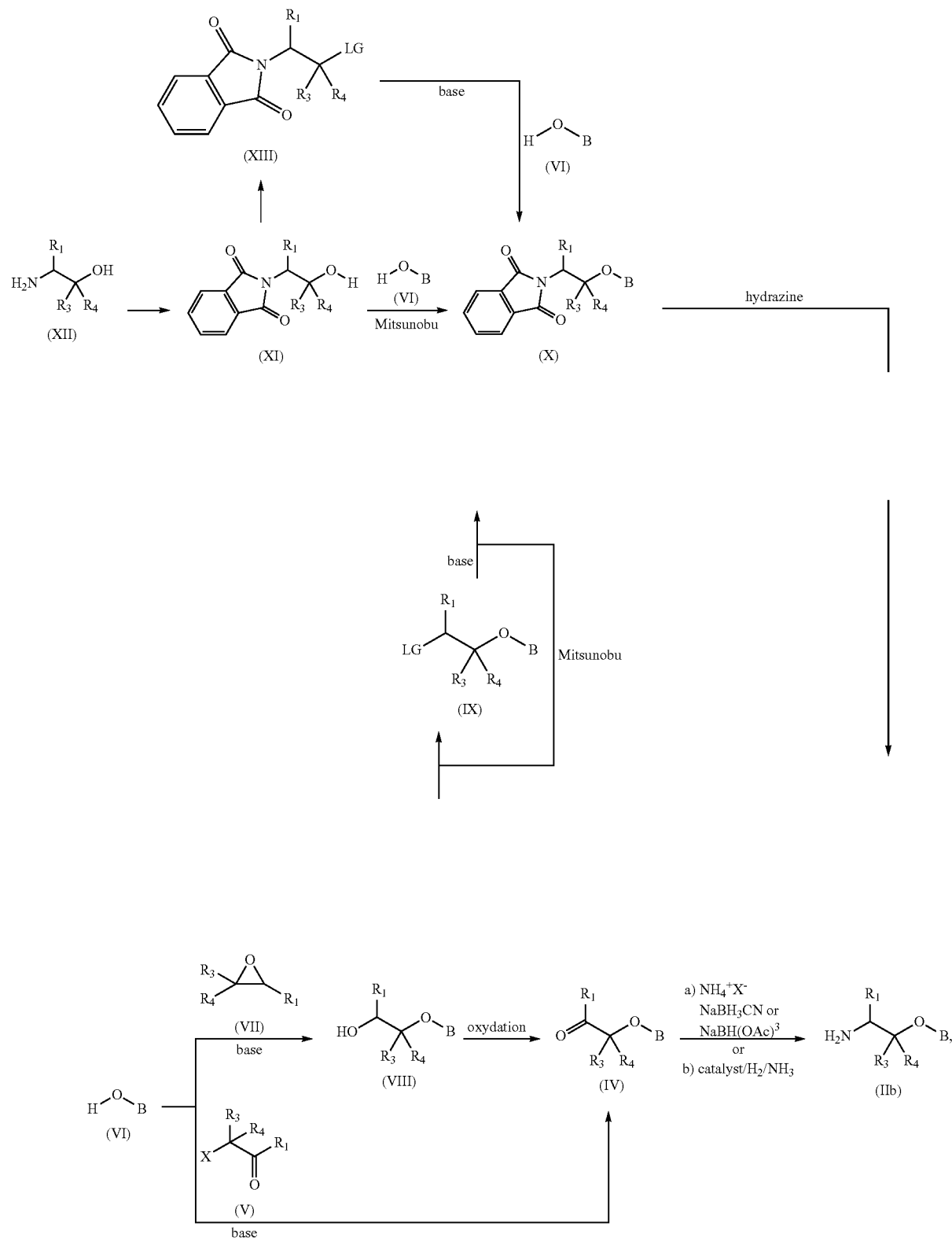

Intermediates of formula IIe, wherein $R_{15}$ is $C_3$-$C_7$cycloalkyl can be for example prepared as shown in Scheme 1a:

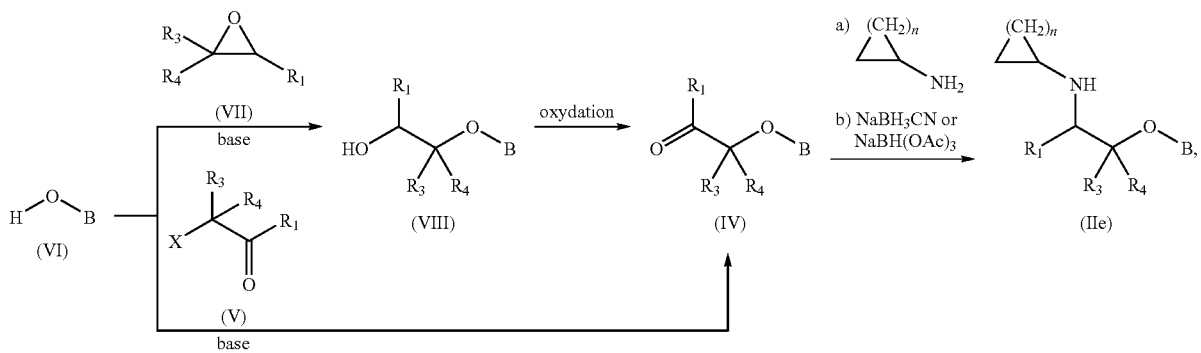

In Scheme 1a, the substituent n signifies 1, 2, 3, 4 or 5. Analogous processes for the preparation of a compound of formula IIe, wherein $R_{15}$ is $C_3$-$C_7$cycloalkyl are described in *J. Het. Chem.*, 1983, p. 1031-6; *J. Am. Soc.*, 2004, p 5192-5201 and *Synth. Commun.* 2003, p 3419-25.

Intermediates of formula IV, in which B, $R_1$, $R_3$ and $R_4$ are as defined under formula IIb, can be prepared by a Williamson reaction of a hydroxy derivative of formula VI, in which B is as defined under formula IIb, with a α-halogen carbonyl compound of formula V, in which $R_1$, $R_3$ and $R_4$ are as defined under formula IIb. Said alkylation reaction may be performed in the presence of a base. Suitable bases include metal hydroxides and/or carbonates such as lithium hydroxide, cesium carbonate, potassium carbonate, potassium hydroxide, sodium hydroxide or metal hydrides, such as sodium hydride and lithium hydride or cesiumfluoride. Suitable solvents include ketones, such as acetone and methyl ethyl ketone, and other solvents, such as N,N-dimethylformamide, dimethylacetamide and nitriles, such as acetonitrile and propionitrile. The reaction temperature can vary within wide limits, but typically is from ambient temperature to the boiling point of the reaction mixture.

Amines of formula IIb can then be prepared from compounds of formula IV by reductive amination with an excess of ammonium halide ($X^-$ is halide) or acetate salt ($X^-$ is acetate) in the presence of a 1-10 equivalents of hydride reducing reagent such as sodium or tetrabutyl cyanoborohydride or sodium triacetoxyborohydride. The reaction can be performed in protic solvents, such as alcohols methanol, ethanol, isopropanol, tert-butanol and the like, or in aprotic solvents, such as tetrahydrofuran or dichloromethane. An acid catalyst such as HCl or p-toluenesulfonic acid can be added portionwise in order to maintain a pH of 3-5 as determined by pH-meter or indicator dye, such as bromocresol green or methyl orange. The reaction temperature typically lies in the range of –5° C. to 60° C.

Alcohols of formula VIII, in which B, $R_1$, $R_3$ and $R_4$ are as defined under formula IIb, are available by ring opening of an epoxyde of formula VII, in which $R_1$, $R_3$ and $R_4$ are as defined under formula IIb, while using the hydroxy derivative of formula VI. The ring opening reaction may be performed in the presence of a catalyst. Suitable catalysts include bases, such as amines like pyridine, tri-ethanolamine and the like, or metal hydroxides and/or carbonates such as lithium hydroxide, cesium carbonate, potassium carbonate, potassium hydroxide, sodium hydroxide or metal hydrides, such as sodium hydride and lithium hydride or cesiumfluoride as well as Lewis acids, such as tetramethylammoniumchlorid. Suitable solvents include alcohols, such as ethanol, isopropanol, tert-butanol and the like, ketones, such as acetone and methyl ethyl ketone, and other solvents, such as N,N-dimethylformamide, dimethylacetamide and nitriles, such as acetonitrile and propionitrile. The reaction temperature can vary within wide limits, but typically is from ambient temperature to the boiling point of the reaction mixture.

The ketone intermediates of formula IV may then be prepared by oxidizing the corresponding alcohols of formula VIII. Advantageous oxidation procedures can be based on sulphur based oxidation agents (in the literature referred to, for example, as Swern-oxidation or Pfizer-Moffat-oxidation), metal based oxidation agents or hydrogen peroxide in the presence of metal catalysts, such as $Na_2WO_4$ (c.f. e.g. R. Noyori, Bull. *Chem. Soc. Jpn.* 1999, 72, 2287-2306).

An alternative access to the compounds of formula IIb (not using the ketone intermediate of formula IV) is also described in scheme 2. Said alternative access uses phthalimide derivatives.

Phthalimide derivatives of formula X, in which B, $R_1$, $R_3$ and $R_4$ are as defined under formula IIb, can be directly prepared by the Gabriel type synthesis reaction—as described by Mitsunobu (O. Mitsunobu, *Synthesis*, 1981, 1-28)—from the alcohol of formula VIII and phthalimide in the presence of 1-2 equivalents of triphenylphosphine and 1-2 equivalents dialkylazodicarboxylate, such as diethylazodicarboxylate or diisopropylazodicarboxylate. The reaction is generally run in an inert solvent, such as tetrahydrofurane or dichloromethane, at a temperature range of 0° C. to 80° C.

The removal of the phthalimide protection group being present in the compounds of formula X to form the desired compounds of formula IIb can be effected by hydrazinolysis or other methods set out in the literature, such as those referenced in Greene, T. W. Protective Groups in Organic Synthesis; J. Wiley & Sons: New York, (1991); Chapter 7.

The phthalimide derivatives of formula X can also be prepared from the alcohols of formula VIII via compounds of formula IX, in which B, $R_1$, $R_3$ and $R_4$ are as defined under formula IIb, and LG stands for a leaving group. Typical leaving groups are chloride, bromide, iodide, (methylsulfonyl)oxy or [(4-methylphenyl)sulfonyl]oxy. In such a reaction, the leaving group LG is displaced in the presence of an acid acceptor, which can be a tertiary amine, such as triethylamine, an alkoxyde, such as tertiary-butoxyde, or a carbonate, such as potassium carbonate. The displacements can be carried out in polar aprotic solvents, such as dimethylformamide or dimethylsulfoxide, ether solvents, such as tetrahydrofurane or dioxane, or protic solvents, such as ethanol. Reaction temperature typically lies in the range of from 20° C. to 150° C.

The phthalimide derivatives of formula X can also be prepared by another approach: phthalimide-protected β-amino alcohols of formula XI, in which $R_1$, $R_3$ and $R_4$ are as defined under formula IIb, can be transformed into the phthalimide derivatives of formula X by a substitution reaction of the hydroxy group while using the hydroxy derivatives of formula VI following the Mitsunobu-procedure (described in: Kenny, J. A., *Synlett*, 1999, (10), 1615-1617).

The compounds of formula XI can be synthesized from an amino alcohol of formula XII, in which $R_1$, $R_3$ and $R_4$ are as defined under formula IIb, by reacting with phthalic anhydride (as described in: Bose, A. K., *J. Org. Chem.*, 1958, 23, 1335-1338).

Yet another access to the phthalimide derivatives of formula X is the transformation of the compounds of formula XI into compounds of formula XIII, in which $R_1$, $R_3$ and $R_4$ are as defined under formula IIb, and LG is a leaving group as defined under formula IX, by standard methods for the conversion of alcohols to halides (as described in: March, J. Advanced Organic Chemistry; J. Wiley & Sons: New York, (1992); 4th Ed, pp 498-499). The compounds of the formula XIII can then be transformed into the compounds of formula X while using the displacement conditions described above for the transformation of the compounds of formula IX into the compounds of formula X.

Intermediates of formula IIc

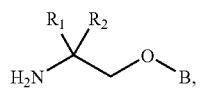

(IIc)

in which B is as defined under formula I and $R_1$, $R_3$ and $R_4$ independently of each other are hydrogen, $C_1$-$C_6$ alkyl, $C_1$-$C_6$ halogenalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ halogenalkoxy, $C_1$-$C_6$ alkylthio or $C_1$-$C_6$ halogenalkylthio; or $R_1$ and $R_2$ together are a $C_2$-$C_5$ alkylene group, which is unsubstituted or substituted by one or more $C_1$-$C_6$ alkyl groups; may be prepared as described in reaction scheme 2.

Scheme 2:

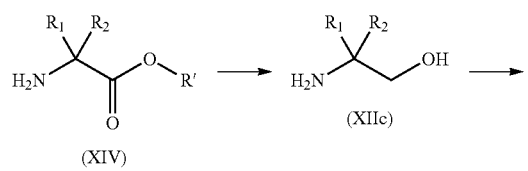

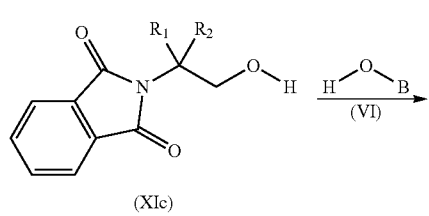

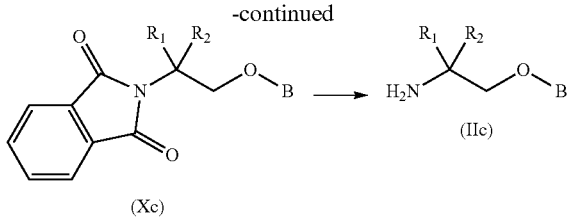

Amino acid derivatives of formula XIV, in which $R_1$ and $R_2$ are as defined under formula IIc, and R' is $C_1$-$C_6$ alkyl, may be reduced into amino alcohols of formula XIIc, in which $R_1$ and $R_2$ are as defined under formula IIc, by using known reduction methods. The amino alcohols of formula XIIc may be transformed into the desired compounds of formula IIc via the phthalimide intermediates of formulae XIc, in which $R_1$ and $R_2$ are as defined under formula IIc, and Xc, in which B, $R_1$ and $R_2$ are as defined under formula IIc, by using the hydroxy derivatives of formula VI and applying the same methodology as described for scheme 1.

Intermediates of the formula II

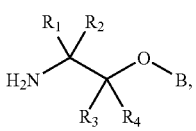

(II)

in which B, $R_1$, $R_2$, $R_3$ and $R_4$ are as defined under formula I, may also be prepared as described in reaction scheme 3a.

Scheme 3a:

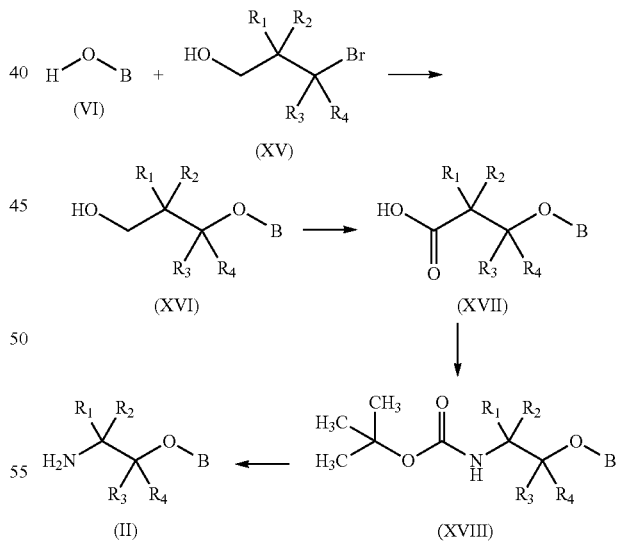

Intermediates of formula XVI, in which B, $R_1$, $R_2$, $R_3$, and $R_4$ are as defined under formula II, can be prepared by a Williamson reaction of a hydroxy derivative of formula VI, in which B is as defined under formula II, with a 3-bromo-propan-1-ol derivative of formula XV, in which $R_1$, $R_2$, $R_3$ and $R_4$ are as defined under formula II, as described in, for example, *Journal Medicinal Chemistry*, 46 (24), 5238-5248; 2003.

The compound of formula XVI can then be oxidized, for example by using RuO$_2$/NaIO$_4$, into the corresponding propanoic acid derivative of formula XVII, in which B, R$_1$, R$_2$, R$_3$, and R$_4$ are as defined under formula II.

The propanoic acid derivative of formula XVII can subsequently be transformed into a BOC-protected carbamate derivative of formula XVIII, in which B, R$_1$, R$_2$, R$_3$, and R$_4$ are as defined under formula II, via Curtius rearrangement of its hydrazide derivative prepared by the use of DPPA and quenching of the isocyanate derivative in the presence of t-Bu-OH (structures of the hydrazide and isocyanate derivatives not shown).

The removal of the BOC-protection group of the compounds of formula XVIII to form the compounds of formula II can be effected in the presence of a strong acid, such as HCl.

Alternatively, compounds of formula II (chiral if R$_1$ is different from R$_2$) may also be prepared as described in reaction scheme 3b:

opening by using oxygen nucleophiles may be performed in the presence of a base. Suitable bases include carbonates, such as lithium hydroxide, cesium carbonate, potassium carbonate, or metal hydrides, such as sodium hydride and lithium hydride. Suitable solvents include N,N-dimethylformamide, dimethylacetamide and DMSO. The reaction temperature can vary within wide limits, but typically is from ambient temperature to 100° C.

Intermediates of formula IId

(IId)

Scheme 3b:

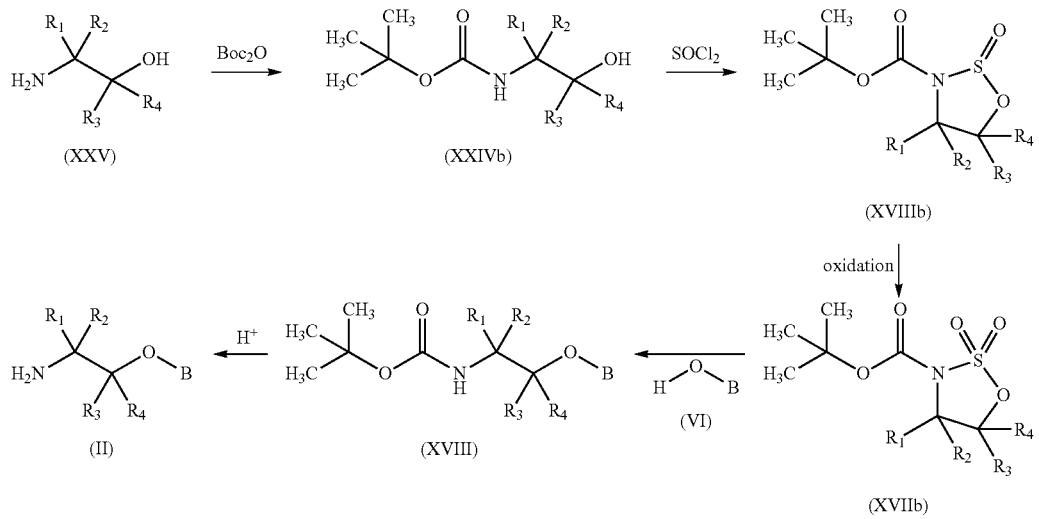

Chiral compounds of formula XXIVb, in which R$_1$, R$_2$, R$_3$, and R$_4$ are as defined under formula Ib and R$_1$ is different from R$_2$, may be prepared by reacting an chiral amino alcohol of formula XXV, in which R$_1$, R$_2$, R$_3$, and R$_4$ are as defined under formula Ib and R$_1$ is different from R$_2$, with Boc$_2$O under standard conditions. Cyclic sulfamidites of formula XXIIIb, in which R$_1$, R$_2$, R$_3$, and R$_4$ are as defined under formula Ib, can then be prepared from the compounds of formula XXIVb by using SOCl$_2$. This cyclisation reaction may be performed in the presence of a base. A suitable base is pyridine. Suitable solvents include dichloromethane and nitriles such as acetonitrile and propionitrile. The reaction temperature typically lies in the range of −50° C. to 20° C.

Cyclic sulfamidates of formula XXIIb, in which A, R$_1$, R$_2$, R$_3$, and R$_4$ are as defined under formula Ib, may be prepared oxidation of the cyclic sulfamidites of formula XXIIIb. Suitable oxidation reagents are RuO$_4$ and RuCl$_3$.3H$_2$O in combination with NaIO$_4$. Suitable solvents include mixtures of nitriles and water; as nitrile can be used, for example, acetonitrile or propionitrile. The reaction temperature typically lies in the range of 0° C. to 30° C.

The cyclic sulfamidates of formula XXIIb may then react with compounds of formula VI, in which B is as defined under formula Ib, to form compounds of formula XVIII. This ring-opening by using oxygen nucleophiles may be performed in which B is as defined under formula I and R$_3$ and R$_4$ independently of each other are hydrogen, C$_1$-C$_6$ alkyl, C$_1$-C$_6$ halogenalkyl, C$_3$-C$_6$cycloalkyl, C$_2$-C$_6$alkenyl, C$_2$-C$_6$haloalkenyl, C$_2$-C$_6$alkynyl, C$_2$-C$_6$ haloalkynyl, C$_1$-C$_6$alkoxy, C$_1$-C$_6$halogenalkoxy, C$_1$-C$_6$alkylthio or C$_1$-C$_6$ halogenalkylthio or R$_3$ and R$_4$ together are a C$_2$-C$_5$alkylene group, which is unsubstituted or substituted by one or more C$_1$-C$_6$alkyl groups; may be prepared as described in reaction scheme 4.

Scheme 4:

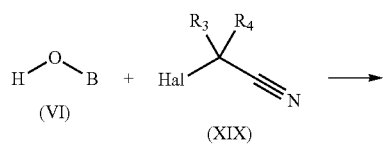

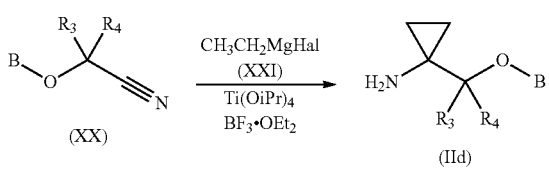

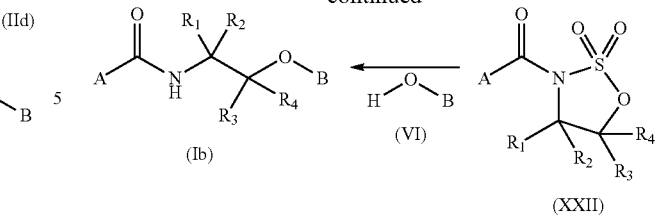

Nitriles of the formula XX, in which B, $R_3$ and $R_4$ are as defined under formula IId, can be prepared by reaction of a compound of formula XIX, in which $R_3$ and $R_4$ are as defined under formula IId, and Hal stands for halogen, with a compound of formula VI, in which B is as defined under formula IId, by using known methods.

The nitrile of formula XX can then undergo a Ti-(II)-mediated coupling with a Grignard-reagent of formula XXI, in which Hal stands for halogen, to afford the desired compounds of formula IId. Reaction conditions for this reaction are described, for example, by P. Bertus and J. Szymoniak (*J. Org. Chem.*, 2002, 67, 3965-3968) and in EP-1-595-873.

Compounds of formula Ib

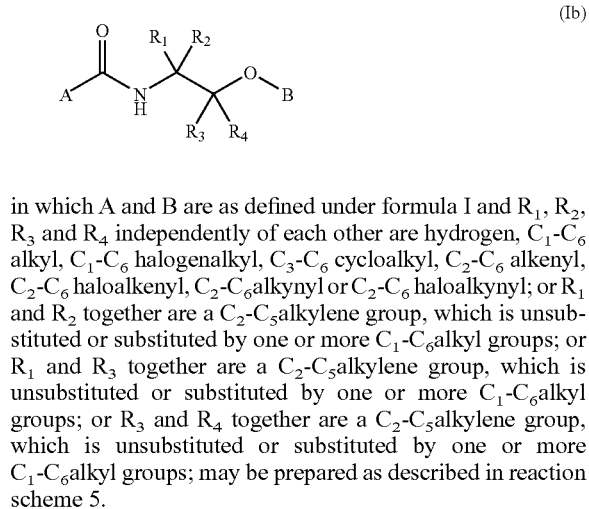

in which A and B are as defined under formula I and $R_1$, $R_2$, $R_3$ and $R_4$ independently of each other are hydrogen, $C_1$-$C_6$ alkyl, $C_1$-$C_6$ halogenalkyl, $C_3$-$C_6$ cycloalkyl, $C_2$-$C_6$ alkenyl, $C_2$-$C_6$ haloalkenyl, $C_2$-$C_6$ alkynyl or $C_2$-$C_6$ haloalkynyl; or $R_1$ and $R_2$ together are a $C_2$-$C_5$alkylene group, which is unsubstituted or substituted by one or more $C_1$-$C_6$alkyl groups; or $R_1$ and $R_3$ together are a $C_2$-$C_5$alkylene group, which is unsubstituted or substituted by one or more $C_1$-$C_6$alkyl groups; or $R_3$ and $R_4$ together are a $C_2$-$C_5$alkylene group, which is unsubstituted or substituted by one or more $C_1$-$C_6$alkyl groups; may be prepared as described in reaction scheme 5.

Scheme 5:

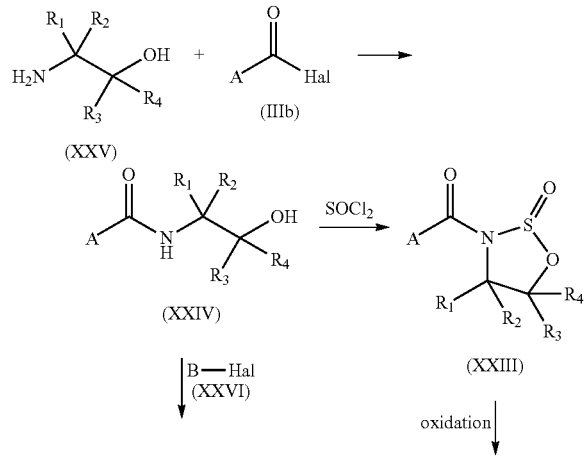

Compounds of formula XXIV, in which A, $R_1$, $R_2$, $R_3$, and $R_4$ are as defined under formula Ib, may be prepared by reacting an amino alcohol of formula XXV, in which $R_1$, $R_2$, $R_3$, and $R_4$ are as defined under formula Ib, with a compound of formula III, in which A is as defined under formula Ib and Hal stands for halogen, preferably chloro, in the presence of a base, such as triethylamine, Hunig base, sodium bicarbonate, sodium carbonate, potassium carbonate, pyridine or quinoline, but preferably triethylamine, and in a solvent, such as diethylether, TBME, THF, dichloromethane, chloroform, DMF or NMP, for between 10 minutes and 48 hours, preferably 12 to 24 hours, and between 0° C. and reflux, preferably 20 to 25° C.

Cyclic sulfamidites of formula XXIII, in which A, $R_1$, $R_2$, $R_3$, and $R_4$ are as defined under formula Ib, can then be prepared from the compounds of formula XXIV by using $SOCl_2$. This cyclisation reaction may be performed in the presence of a base. A suitable base is pyridine. Suitable solvents include dichloromethane and nitriles such as acetonitrile and propionitrile. The reaction temperature typically lies in the range of −50° C. to 20° C.

Cyclic sulfamidates of formula XXII, in which A, $R_1$, $R_2$, $R_3$, and $R_4$ are as defined under formula Ib, may be prepared oxidation of the cyclic sulfamidites of formula XXIII. Suitable oxidation reagents are $RuO_4$ and $RuCl_3.3H_2O$ in combination with $NaIO_4$. Suitable solvents include mixtures of nitriles and water; as nitrile can be used, for example, acetonitrile or propionitrile. The reaction temperature typically lies in the range of 0° C. to 30° C.

For a review of preparation methods for cyclic sulfates and sulfamidates, see Lohray, B. B. in *Advances in Heterocyclic Chemistry*; Katritzky, A. R., Ed.; Academic Press: San Diego, 1997; Vol. 68, pp 89-180; and Posakony J. J., *J. Org. Chem.*, 2002, 67, 5164-5169.

The cyclic sulfamidates of formula XXII may then react with compounds of formula VI, in which B is as defined under formula Ib, to form compounds of formula Ib. This ring-opening by using oxygen nucleophiles may be performed in the presence of a base. Suitable bases include carbonates, such as lithium hydroxide, cesium carbonate, potassium carbonate, or metal hydrides, such as sodium hydride and lithium hydride. Suitable solvents include N,N-dimethylformamide, dimethylacetamide and DMSO. The reaction temperature can vary within wide limits, but typically is from ambient temperature to 100° C.

Alternatively, compounds of formula Ib may be prepared by the reaction of compounds of formula XXIV and compounds of formula XXVI, in which B is as defined under formula Ib and Hal stands for halogen. This nucleophilic substitution reaction may preferably be used in the case that the compound of formula XXVI is an activated halogen-aromatic compound. In the case that the compound of formula XXVI is a non-activated compound, said reaction may be carried out under palladium- or copper-catalyst mediated conditions.

Scheme 6: Synthesis of Naphthole Intermediates wherein $R_3$ and $R_4$ are hydrogen:

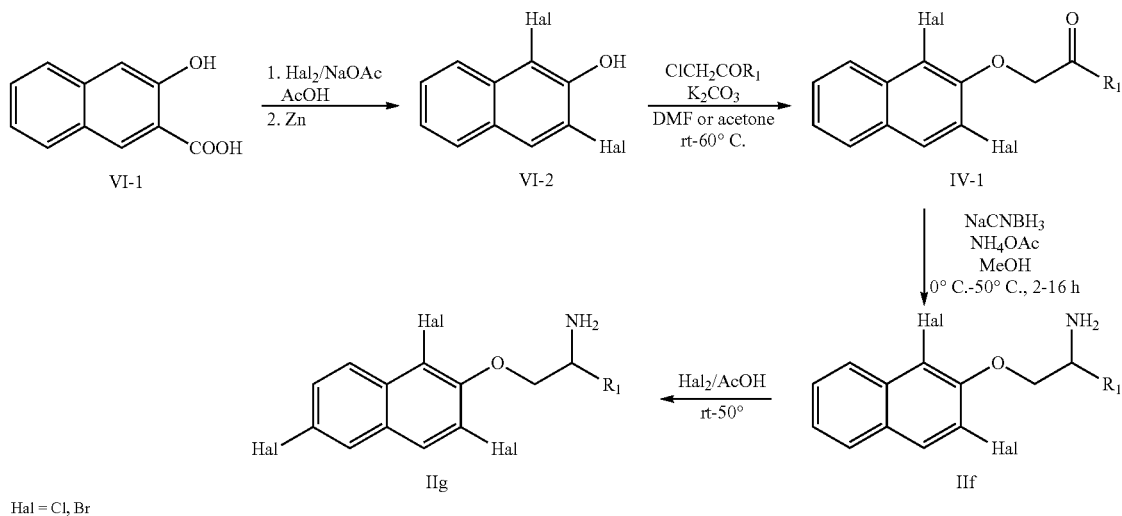

Hal = Cl, Br

For the synthesis of 1.3-substituted naphthols see Annalen 1930, 484, 245-300

Scheme 7: Synthesis of 5-hydroxybenzo[b]thiophene intermediates wherein $R_3$ and $R_4$ are hydrogen:

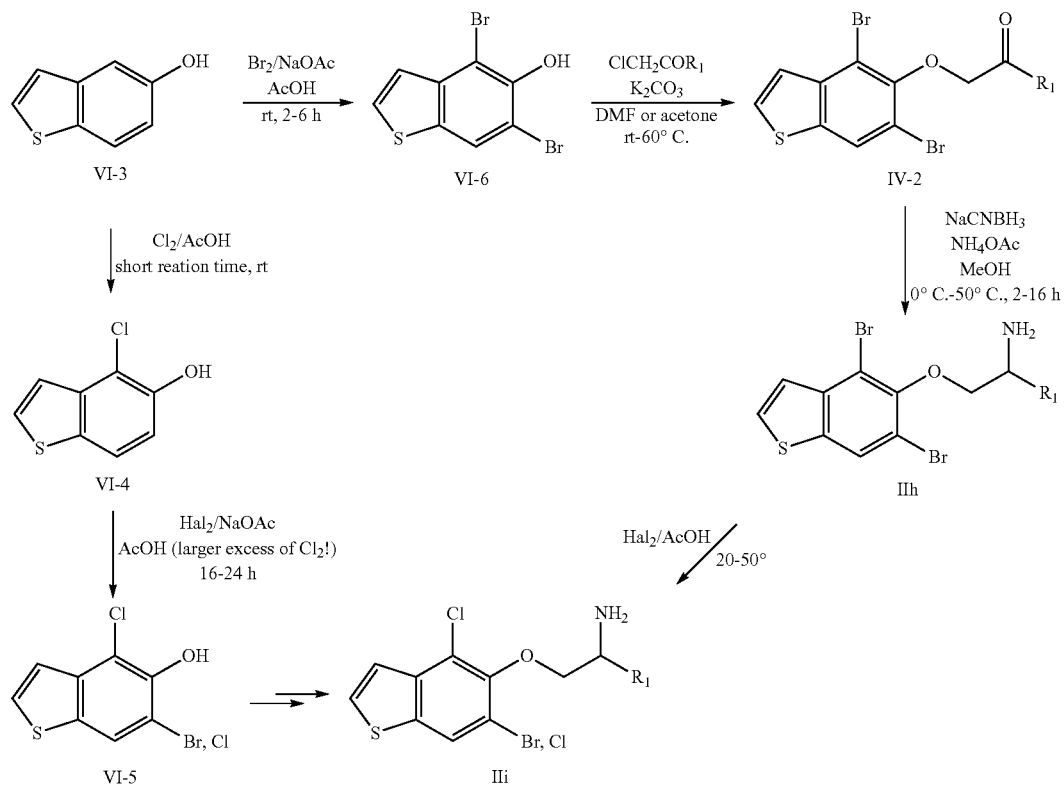

For the synthesis of 5-hydroxybenzo[b]thiophene see: Synthetic Communications, 1991, 21, 959-964.

The compounds of the formulae V, VI, VII, XII, XIV, XV, XIX, XXV and XXVI, wherein the substituents as described above, are known and commercially available or can be prepared according to the above-mentioned references or according to methods known in the art.

The compounds of the formula III and IIIb, wherein the substituents as described above, are known and partially commercially available. They can be prepared analogously as described, for example, in WO 00/09482, WO 02/38542, WO 04/018438, EP-0-589-301, WO 93/11117 and Arch. Pharm. Res. 2000, 23 (4), 315-323.

For preparing all further compounds of the formula I functionalized according to the definitions of A, B, $R_1$, $R_2$, $R_3$ and $R_4$, there are a large number of suitable known standard methods, such as alkylation, halogenation, acylation, amidation, oximation, oxidation and reduction. The choice of the preparation methods which are suitable are depending on the properties (reactivity) of the substituents in the intermediates.

The reactions to give compounds of the formula I are advantageously carried out in aprotic inert organic solvents. Such solvents are hydrocarbons such as benzene, toluene, xylene or cyclohexane, chlorinated hydrocarbons such as dichloromethane, trichloromethane, tetrachloromethane or chlorobenzene, ethers such as diethyl ether, ethylene glycol dimethyl ether, diethylene glycol dimethyl ether, tetrahydrofuran or dioxane, nitriles such as acetonitrile or propionitrile, amides such as N,N-dimethylformamide, diethylformamide or N-methylpyrrolidinone. The reaction temperatures are advantageously between −20° C. and +120° C. In general, the reactions are slightly exothermic and, as a rule, they can be carried out at ambient temperature. To shorten the reaction time, or else to start the reaction, the mixture may be heated briefly to the boiling point of the reaction mixture. The reaction times can also be shortened by adding a few drops of base as reaction catalyst. Suitable bases are, in particular, tertiary amines such as trimethylamine, triethylamine, quinuclidine, 1,4-diazabicyclo[2.2.2]octane, 1,5-diazabicyclo[4.3.0]non-5-ene or 1,5-diazabicyclo-[5.4.0]undec-7-ene. However, inorganic bases such as hydrides, e.g. sodium hydride or calcium hydride, hydroxides, e.g. sodium hydroxide or potassium hydroxide, carbonates such as sodium carbonate and potassium carbonate, or hydrogen carbonates such as potassium hydrogen carbonate and sodium hydrogen carbonate may also be used as bases. The bases can be used as such or else with catalytic amounts of a phase-transfer catalyst, for example a crown ether, in particular 18-crown-6, or a tetraalkylammonium salt.

The compounds of formula I can be isolated in the customary manner by concentrating and/or by evaporating the solvent and purified by recrystallization or trituration of the solid residue in solvents in which they are not readily soluble, such as ethers, aromatic hydrocarbons or chlorinated hydrocarbons.

The compounds I and, where appropriate, the tautomers thereof, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

The compounds I and, where appropriate, the tautomers thereof, can, if appropriate, also be obtained in the form of hydrates and/or include other solvents, for example those which may have been used for the crystallization of compounds which are present in solid form.

The intermediates of the formula II

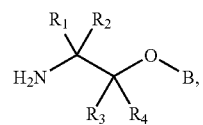

(II)

in which B, $R_1$, $R_2$, $R_3$ and $R_4$ are as defined under formula I, are novel and were developed specifically for the preparation of the compounds of the formula I. Accordingly, these intermediates of the formula II also form part of the subject-matter of the present invention.

The intermediates of the formula IIa

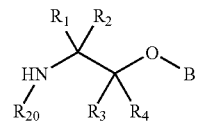

(IIa)

in which B, $R_1$, $R_2$, $R_3$ and $R_4$ are as defined under formula I, and $R_{20}$ is $C_3$-$C_7$cycloalkyl preferably cyclopropyl, are novel and were developed specifically for the preparation of the compounds of the formula I. Accordingly, these intermediates of the formula II also form part of the subject-matter of the present invention.

The intermediates of the formula IV

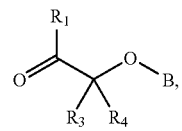

(IV)

in which B is as defined under formula I and $R_1$, $R_3$ and $R_4$ independently of each other are hydrogen, $C_1$-$C_6$ alkyl, $C_1$-$C_6$ halogenalkyl, $C_3$-$C_6$ cycloalkyl, $C_2$-$C_6$ alkenyl, $C_2$-$C_6$ haloalkenyl, $C_2$-$C_6$alkynyl, $C_2$-$C_6$ haloalkynyl, $C_1$-$C_6$ alkoxy, $C_1$-$C_6$ halogenalkoxy, $C_1$-$C_6$ alkylthio or $C_1$-$C_6$ halogenalkylthio; or $R_1$ and $R_3$ together are a $C_2$-$C_5$alkylene group, which is unsubstituted or substituted by one or more $C_1$-$C_6$alkyl groups; or $R_3$ and $R_4$ together are a $C_2$-$C_5$alkylene group, which is unsubstituted or substituted by one or more $C_1$-$C_6$alkyl groups; are novel and were developed specifically for the preparation of the compounds of the formula I.

Accordingly, these intermediates of the formula IV also form part of the subject-matter of the present invention.

The intermediates of the formula XXIV

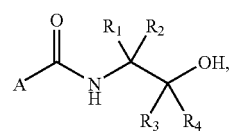

(XXIV)

in which A is as defined under formula I and $R_1$, $R_2$, $R_3$ and $R_4$ independently of each other are hydrogen, $C_1$-$C_6$ alkyl, $C_1$-$C_6$ halogenalkyl, $C_3$-$C_6$ cycloalkyl, $C_2$-$C_6$ alkenyl, $C_2$-$C_6$ haloalkenyl, $C_2$-$C_6$alkynyl or $C_2$-$C_6$ haloalkynyl; or $R_1$ and $R_2$ together are a $C_2$-$C_5$alkylene group, which is unsubstituted or substituted by one or more $C_1$-$C_6$alkyl groups; or $R_1$ and $R_3$ together are a $C_2$-$C_5$alkylene group, which is unsubstituted or substituted by one or more $C_1$-$C_6$alkyl groups; or $R_3$ and $R_4$ together are a $C_2$-$C_5$alkylene group, which is unsubstituted or substituted by one or more $C_1$-$C_6$alkyl groups; are novel and were developed specifically for the preparation of the compounds of the formula I. Accordingly, these intermediates of the formula XXIV also form part of the subject-matter of the present invention.

The intermediates of the formula XXIVa

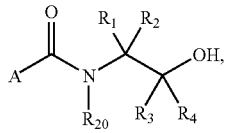

(XXIVa)

in which A is as defined under formula I, $R_{20}$ is $C_3$-$C_7$cycloalkyl, preferably cyclopropyl, and $R_1$, $R_2$, $R_3$ and $R_4$ independently of each other are hydrogen, $C_1$-$C_6$ alkyl, $C_1$-$C_6$ halogenalkyl, $C_3$-$C_6$ cycloalkyl, $C_2$-$C_6$ alkenyl, $C_2$-$C_6$ haloalkenyl, $C_2$-$C_6$alkynyl or $C_2$-$C_6$ haloalkynyl; or $R_1$ and $R_2$ together are a $C_2$-$C_6$alkylene group, which is unsubstituted or substituted by one or more $C_1$-$C_6$alkyl groups; or $R_1$ and $R_3$ together are a $C_2$-$C_5$alkylene group, which is unsubstituted or substituted by one or more $C_1$-$C_6$alkyl groups; or $R_3$ and $R_4$ together are a $C_2$-$C_5$alkylene group, which is unsubstituted or substituted by one or more $C_1$-$C_6$alkyl groups; are novel and were developed specifically for the preparation of the compounds of the formula I. Accordingly, these intermediates of the formula XXIV also form part of the subject-matter of the present invention.

The intermediates of the formula XXIIB

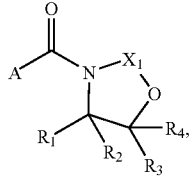

(XXIIB)

in which A is as defined under formula I; $X_1$ is —S(O)— or —S(O)$_2$—; and $R_1$, $R_2$, $R_3$ and $R_4$ independently of each other are hydrogen, $C_1$-$C_6$ alkyl, $C_1$-$C_6$ halogenalkyl, $C_3$-$C_6$ cycloalkyl, $C_2$-$C_6$ alkenyl, $C_2$-$C_6$ haloalkenyl, $C_2$-$C_6$alkynyl or $C_2$-$C_6$ haloalkynyl; or $R_1$ and $R_2$ together are a $C_2$-$C_5$alkylene group, which is unsubstituted or substituted by one or more $C_1$-$C_6$alkyl groups; or $R_1$ and $R_3$ together are a $C_2$-$C_5$alkylene group, which is unsubstituted or substituted by one or more $C_1$-$C_6$alkyl groups; or $R_3$ and $R_4$ together are a $C_2$-$C_5$alkylene group, which is unsubstituted or substituted by one or more $C_1$-$C_6$alkyl groups; are novel and were developed specifically for the preparation of the compounds of the formula I.

Accordingly, these intermediates of the formula XXIIB also form part of the subject-matter of the present invention.

It has now been found that the compounds of formula I according to the invention have, for practical purposes, a very advantageous spectrum of activities for protecting useful plants against diseases that are caused by phytopathogenic microorganisms, such as fungi, bacteria or viruses.

The invention relates to a method of controlling or preventing infestation of useful plants by phytopathogenic microorganisms, wherein a compound of formula I is applied as active ingredient to the plants, to parts thereof or the locus thereof. The compounds of formula I according to the invention are distinguished by excellent activity at low rates of application, by being well tolerated by plants and by being environmentally safe. They have very useful curative, preventive and systemic properties and are used for protecting numerous useful plants. The compounds of formula I can be used to inhibit or destroy the diseases that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula I as dressing agents for the treatment of plant propagation material, in particular of seeds (fruit, tubers, grains) and plant cuttings (e.g. rice), for the protection against fungal infections as well as against phytopathogenic fungi occurring in the soil.

Furthermore the compounds of formula I according to the invention may be used for controlling fungi in related areas, for example in the protection of technical materials, including wood and wood related technical products, in food storage or in hygiene management.

The compounds of formula I are, for example, effective against the phytopathogenic fungi of the following classes: Fungi imperfecti (e.g. *Botrytis, Pyricularia, Helminthosporium, Fusarium, Septoria, Cercospora* and *Alternaria*) and Basidiomycetes (e.g. *Rhizoctonia, Hemileia, Puccinia*). Additionally, they are also effective against the Ascomycetes classes (e.g. *Venturia* and *Erysiphe, Podosphaera, Monilinia, Uncinula*) and of the Oomycetes classes (e.g. *Phytophthora, Pythium, Plasmopara*). Outstanding activity has been observed against powdery mildew (*Erysiphe* spp.). Furthermore, the novel compounds of formula I are effective against phytopathogenic bacteria and viruses (e.g. against *Xanthomonas* spp, *Pseudomonas* spp, *Erwinia amylovora* as well as against the tobacco mosaic virus). Good activity has been observed against Asian soybean rust (*Phakopsora pachyrhizi*).

Within the scope of the invention, useful plants to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, *cinnamomum*, camphor) or plants such as tobacco, nuts, coffee, eggplants, sugar cane, tea, pepper, vines, hops, bananas and natural rubber plants, as well as ornamentals.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g.

imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

The compounds of formula I can be used in unmodified form or, preferably, together with carriers and adjuvants conventionally employed in the art of formulation.

Therefore the invention also relates to compositions for controlling and protecting against phytopathogenic microorganisms, comprising a compound of formula I and an inert carrier, and to a method of controlling or preventing infestation of useful plants by phytopathogenic microorganisms, wherein a composition, comprising a compound of formula I as active ingredient and an inert carrier, is applied to the plants, to parts thereof or the locus thereof.

To this end compounds of formula I and inert carriers are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula I or compositions, comprising a compound of formula I as active ingredient and an inert carrier, can be applied to the locus of the plant or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

A preferred method of applying a compound of formula I, or a composition, comprising a compound of formula I as active ingredient and an inert carrier, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation, i.e. a composition comprising the compound of formula I and, if desired, a solid or liquid adjuvant, is prepared in a known manner, typically by intimately mixing and/or grinding the compound with extenders, for example solvents, solid carriers and, optionally, surface-active compounds (surfactants).

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient rates of application are from 10 mg to 1 g of active substance per kg of seeds. The rate of application for the desired action can be determined by experiments. It depends for example on the type of action, the developmental stage of the useful plant, and on the application (location, timing, application method) and can, owing to these parameters, vary within wide limits.

Surprisingly, it has now been found that the compounds of formula I can also be used in methods of protecting crops of useful plants against attack by phytopathogenic organisms as well as the treatment of crops of useful plants infested by phytopathogenic organisms comprising administering a combination of glyphosate and at least one compound of formula I to the plant or locus thereof, wherein the plant is resistant or sensitive to glyphosate.

Said methods may provide unexpectedly improved control of diseases compared to using the compounds of formula I in the absence of glyphosate. Said methods may be effective at enhancing the control of disease by compounds of formula I. While the mixture of glyphosate and at least one compound of formula I may increase the disease spectrum controlled, at least in part, by the compound of formula I, an increase in the activity of the compound of formula I on disease species already known to be controlled to some degree by the compound of formula I can also be the effect observed.

Said methods are particularly effective against the phytopathogenic organisms of the kingdom Fungi, phylum Basidiomycot, class Uredinomycetes, subclass Urediniomycetidae and the order Uredinales (commonly referred to as rusts). Species of rusts having a particularly large impact on agriculture include those of the family Phakopsoraceae, particularly those of the genus *Phakopsora*, for example *Phakopsora pachyrhizi*, which is also referred to as Asian soybean rust, and those of the family Pucciniaceae, particularly those of the genus *Puccinia* such as *Puccinia graminis*, also known as stem rust or black rust, which is a problem disease in cereal crops and *Puccinia recondita*, also known as brown rust.

An embodiment of said method is a method of protecting crops of useful plants against attack by a phytopathogenic organism and/or the treatment of crops of useful plants infested by a phytopathogenic organism, said method comprising simultaneously applying glyphosate, including salts or esters thereof, and at least one compound of formula I, which has activity against the phytopathogenic organism to at least one member selected from the group consisting of the plant, a part of the plant and the locus of the plant.

The compounds of formula (I), or a pharmaceutical salt thereof, described above may also have an advantageous spectrum of activity for the treatment and/or prevention of microbial infection in an animal.

"Animal" can be any animal, for example, insect, mammal, reptile, fish, amphibian, preferably mammal, most preferably human. "Treatment" means the use on an animal which has microbial infection in order to reduce or slow or stop the increase or spread of the infection, or to reduce the infection or to cure the infection. "Prevention" means the use on an animal which has no apparent signs of microbial infection in order to prevent any future infection, or to reduce or slow the increase or spread of any future infection.

According to the present invention there is provided the use of a compound of formula (I) in the manufacture of a medicament for use in the treatment and/or prevention of microbial infection in an animal. There is also provided the use of a compound of formula (I) as a pharmaceutical agent. There is also provided the use of a compound of formula (I) as an antimicrobial agent in the treatment of an animal. According to the present invention there is also provided a pharmaceutical composition comprising as an active ingredient a compound of formula (I), or a pharmaceutically acceptable salt thereof, and a pharmaceutically acceptable diluent or carrier. This composition can be used for the treatment and/or prevention of antimicrobial infection in an animal. This pharmaceutical composition can be in a form suitable for oral administration, such as tablet, lozenges, hard capsules, aqueous suspensions, oily suspensions, emulsions dispersible powders, dispersible granules, syrups and elixirs. Alternatively this pharmaceutical composition can be in a form suitable for topical application, such as a spray, a cream or lotion. Alternatively this pharmaceutical composition can be in a form suitable for parenteral administration, for example injection. Alternatively this pharmaceutical composition can be in inhalable form, such as an aerosol spray.

The compounds of formula (I) may be effective against various microbial species able to cause a microbial infection in an animal. Examples of such microbial species are those causing Aspergillosis such as *Aspergillus fumigatus, A. flavus, A. terrus, A. nidulans* and *A. niger*, those causing Blastomycosis such as *Blastomyces dermatitidis*; those causing Candidiasis such as *Candida albicans, C. glabrata, C. tropicalis, C. parapsilosis, C. krusei* and *C. lusitaniae*; those causing Coccidioidomycosis such as *Coccidioides immitis*; those causing Cryptococcosis such as *Cryptococcus neoformans*; those causing Histoplasmosis such as *Histoplasma capsulatum* and those causing Zygomycosis such as *Absidia corymbifera, Rhizomucor pusillus* and *Rhizopus arrhizus*. Further examples are *Fusarium* Spp such as *Fusarium oxysporum* and *Fusarium solani* and *Scedosporium* Spp such as *Scedosporium apiospermum* and *Scedosporium prolificans*. Still further examples are *Microsporum* Spp, *Trichophyton* Spp, *Epidermophyton* Spp, *Mucor* Spp, *Sporothorix* Spp, *Phialophora* Spp, *Cladosporium* Spp, *Petriellidium* spp, *Paracoccidioides* Spp and *Histoplasma* Spp.

The following non-limiting Examples illustrate the above-described invention in greater detail without limiting it.

PREPARATION EXAMPLES

Example P1

Preparation of 3-difluoromethyl-1-methyl-1H-pyrazole-4-carboxylic acid [2-(4-acetyl-p-phenoxy)-1-methyl-ethyl]-amide (compound 1.098)

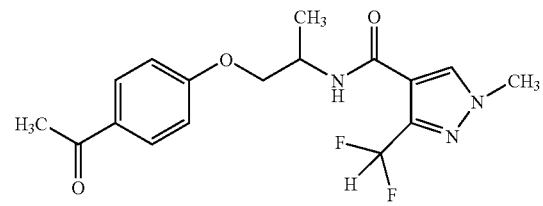

To a solution of 4-hydroxyacetophenone (0.14 g; 1 mmol) in dimethylformamide (4 ml) sodium hydride 50% in oil (0.04 g; 1 mmol) is added portion wise. The reaction mixture is stirred for 15 minutes at ambient temperature followed by the addition of 3-difluoromethyl-1-methyl-1H-pyrazol-4-yl)-4-methyl-2,2-dioxo-2-λ-*6*-[1,2,3]oxathiazolidin-3-yl)-methanone (0.33 g; 1.1 mmol), which is prepared as described in example P5c, in dimethylformamide (0.5 ml). The reaction mixture is stirred for 1 h at ambient temperature then poured onto 1M HCl (40 ml) and extracted with ethyl acetate (2×30 ml). The combined ethyl acetate layers are washed with water (20 ml) and then dried over $Na_2SO_4$. After removal of the solvent the residue is purified by flash chromatography over silica gel (eluent: cyclo hexane/ethyl acetate 7:3). 0.16 g (46% of theory) of 3-difluoromethyl-1-methyl-1H-pyrazole-4-carboxylic acid [2-(4-acetyl-p-phenoxy)-1-methyl-ethyl]-amide (compound 1.098) is obtained in form of a resin.

$^1$H NMR (400 MHz, $CDCl_3$): δ 1.40 (d, 3H, $CH_3$), 2.53 (s, 3H, $CH_3$), 3.90 (s, 3H, $CH_3$), 4.05-4.12 (m, 2H, $CH_2$), 4.52-4.57 (m, 1H, CH), 6.68 ($m_{broad}$, 1H, NH), 6.71-6.98 (t, 1H, $CHF_2$), 6.94-6.97 (d, 2H, Ar—H), 7.90-7.94 (m, 3H, 2H—Ar+1H, Pyrazol-H).

MS $[M+H]^+$ 352.

Example P2

Preparation of 3-difluoromethyl-1-methyl-1H-pyrazole-4-carboxylic acid [2-(2,6-dimethyl-phenoxy)-1-methyl-ethyl]-amide (compound 1.166) and 3-difluoromethyl-1-methyl-1H-pyrazole-4-carboxylic acid [2-(4-bromo-2,6-dimethyl-phenoxy)-1-methyl-ethyl]-amide (compound 1.168)

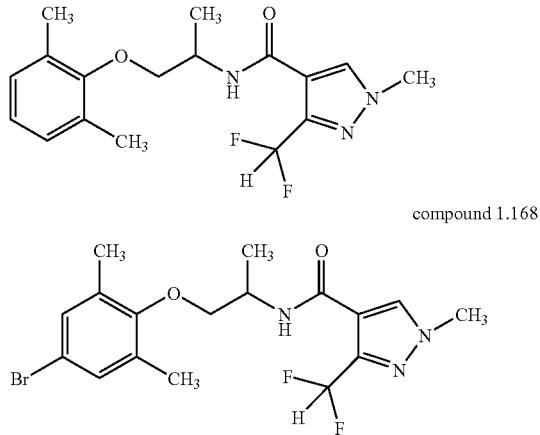

compound 1.166 compound 1.168

At 0° C., a solution of 3-difluoromethyl-1-methyl-1H-pyrazole-4-carbonyl chloride (0.29 g; 1.5 mmol) in dichloromethane (3 ml) is added dropwise to a stirred solution of 0.35 g (1.5 mmol) of a 4:1-mixture of 2-(4-bromo-2,6-dimethyl-phenoxy)-1-methyl-ethylamine (compound Z1.168) and 2-(2,6-dimethyl-phenoxy)-1-methyl-ethylamine (compound Z1.166), which is prepared as described in example P6, and triethylamine (0.3 g; 3 mmol) in dichloromethane (20 ml). The reaction mixture is stirred for 1 h at ambient temperature and then allowed to stand for 2 h. The reaction mixture is washed with 1M NaOH (10 ml) and 1M HCl (10 ml) and then dried over Na$_2$SO$_4$. After removal of the solvent, 0.65 g of a residue remained. Both reaction products are isolated by column-chromatography (column from Waters, RP PrepC18, 10 μm, 50 mm×250 mm; solvents: A=acetonitrile, B=water; gradient: 50% to 0% B in 15 min; flow rate: 2.0 ml/min):

a) 90 mg (18% of theory) of 3-difluoromethyl-1-methyl-1H-pyrazole-4-carboxylic acid [2-(2,6-dimethyl-phenoxy)-1-methyl-ethyl]-amide (compound 1.166) is obtained in the form of a solid (m.p. 142-146° C.). Retention time for this compound is 10.78 min.

$^1$H NMR (400 MHz, CDCl$_3$): δ 1.46-1.48 (d, 3H), 2.21 (2s, 6H), 3.77-3.87 (ddd, 2H), 3.94 (s, 3H), 4.47-4.53 (m, 1H), 6.76-7.03 (t, 1H), 6.79 (s, 1H), 6.91 (d, 1H), 7.00 (d, 2H), 7.93 (s, 1H).

MS [M+H]$^+$ 338.

b) 390 mg (63% of theory) of 3-difluoromethyl-1-methyl-1H-pyrazole-4-carboxylic acid [2-(4-bromo-2,6-dimethyl-phenoxy)-1-methyl-ethyl]-amide (compound 1.168) is obtained in the form of a solid (m.p. 119-121° C.). Retention time for this compound is 12.53 min.

$^1$H NMR (400 MHz, CDCl$_3$): δ 1.44-1.46 (d, 3H), 2.21 (2s, 6H), 3.72-3.85 (ddd, 2H), 3.89 (s, 3H), 4.46-4.51 (m, 1H), 6.76 (s, 1H), 6.77-7.03 (t, 1H), 7.11 (s, 1H), 7.93 (s, 1H).

MS [M+H]$^+$ 416/418.

Example P3

Preparation of 3-difluoromethyl-1-methyl-1H-pyrazole-4-carboxylic acid [1-methyl-2-(2,4,6-tribromo-phenoxy)-ethyl]-amide (compound 1.193)

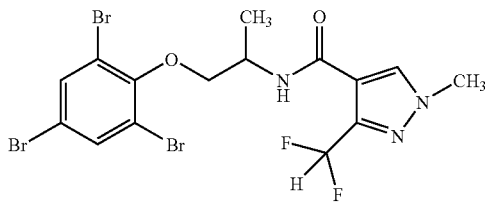

A mixture of 0.3 g (0.8 mmol) 1-methyl-2-(2,4,6-tribromo-phenoxy)-ethylamine (compound Z1.193, prepared as described in example P7) and 0.15 g (0.9 mmol) 3-difluoromethyl-1-methyl-1H-pyrazole-4-carboxylic acid in 2 ml pyridine under a nitrogen atmosphere is cooled to 0° C. Phosphorus oxychloride (0.08 ml, 0.9 mmol) is added dropwise and the reaction mixture is stirred at 80° C. for 12 h. The reaction mixture is diluted with water and 3-times extracted with ethyl acetate. The combined ethyl acetate layers are washed with 1.5 N HCl, saturated NaHCO$_3$, water and brine, dried over sodium sulphate and evaporated to dryness. The residue is purified by column chromatography (using 60-120 mesh-silica gel in hexane; eluent: ethyl acetate) to yield 0.12 g 3-difluoromethyl-1-methyl-1H-pyrazole-4-carboxylic acid [1-methyl-2-(2,4,6-tribromo-phenoxy)-ethyl]-amide (27% of theory) as a yellow solid.

$^1$H NMR (400 MHz, CDCl3): δ 1.48-1.50 (d, 3H), 3.93 (s, 3H, NCH3), 4.02-4.12 (ddd, 2H, CH2), 4.50-4.55 (m, 1H), 6.67 (s, 1H, NH), 6.78-7.05 (t, 1H, CHF2), 7.65 (s, 1H), 7.88 (S, 1H, pyrazole-H), LCMS {ESI+mode}: 543.8/545.77/549.81

Example P4

Preparation of 3-difluoromethyl-1-methyl-1H-pyrazole-4-carboxylic acid [2-(3-chloro-5-trifluoromethyl-pyridin-2-yloxy)-1-methyl-ethyl]-amide (compound 1.239)

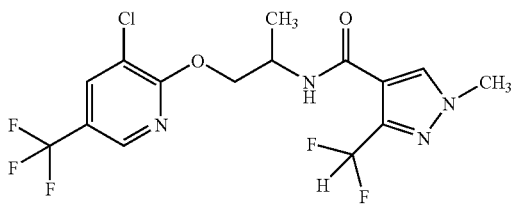

A solution of 2.3 g 3-difluoromethyl-1-methyl-1H-pyrazole-4-carboxylic acid (2-hydroxy-1-methyl-ethyl)-amide (10.0 mmol, prepared as described in example P5a) and 2.6 g 2-bromo-3-chloro-5-trifluoromethyl-pyridine (10 mmol) in dimethylformamide (30 ml) is treated at ambient temperature with 2.8 g potassium carbonate (20 mmol). The resulting suspension is stirred at 100° C. for 3 hours, cooled to ambient temperature, poured onto water (200 ml) and extracted with ethyl acetate (2×100 ml). The combined ethyl acetate layers are washed with water (20 ml) and dried over Na$_2$SO$_4$. After removal of the solvent the residue (4.2 g in the form of an oil) is purified by flash chromatography over silica gel (eluent: cyclohexane/ethyl acetate 3:7). 1.4 g (34% of theory) of 3-difluoromethyl-1-methyl-1H-pyrazole-4-carboxylic acid [2-(3-chloro-5-trifluoromethyl-pyridin-2-yloxy)-1-methyl-ethyl]-amide (compound 1.239) is obtained in form of a solid (mp. 115-118° C.).

$^1$H NMR (400 MHz, CDCl$_3$): δ 1.39-1.41 (d, 3H, CH$_3$), 3.91 (s, 3H, CH$_3$), 4.46-4.54 (m, 2H, CH$_2$), 4.60-4.66 (m, 1H, CH), 6.63 (s, 1H, NH), 6.67-6.81 (t, 1H, CHF2), 7.85 (d, 1H, Py-H), 7.90 (s, 1H, pyrazol-H), 8.30 (t, 1H, Py-H).

MS [M+H]$^+$ 413/415.

Example P5

Preparation of 3-difluoromethyl-1-methyl-1H-pyrazol-4-yl)-4-methyl-2,2-dioxo-2-λ-*6*-[1,2,3]oxathiazolidin-3-yl)-methanone a) Preparation of 3-difluoromethyl-1-methyl-1H-pyrazole-4-carboxylic acid (2-hydroxy-1-methyl-ethyl)-amide

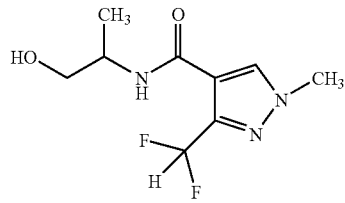

At 0° C., a solution of 38.9 g 3-difluoromethyl-1H-pyrazole-4-carbonyl chloride (0.2 mol) in 100 ml dichloromethane is added dropwise to a stirred solution of 15 g alaninol (0.2 mol) and 25 g triethylamine (0.25 mol) in 400 ml dichloromethane. The reaction mixture is stirred for 1 h at ambient temperature and then allowed to stand for 3 h at ambient temperature. After removal of the solvent the residue is purified by flash chromatography over silica gel 400 g (eluent: ethyl acetate/methanol 19:1). 42 g (90% of theory) of 3-difluoromethyl-1-methyl-1H-pyrazole-4-carboxylic acid (2-hydroxy-1-methyl-ethyl)-amide is obtained in form of a solid (mp. 81-87° C.).

$^1$H NMR (400 MHz, CDCl$_3$): δ 1.23-1.26 (d, 3H), 2.97 (s, 1H$_2$OH), 3.57-3.73 (ddd, 2H), 3.94 (s, 3H), 4.17-4.23 (m, 1H), 6.57 (s, 1H), 6.75-7.02 (t, 1H), 7.90 (s, 1H).

MS [M+H]$^+$ 234.

b) Preparation of 3-difluoromethyl-1-methyl-1H-pyrazol-4-yl)-4-methyl-2-oxo-2-λ-*4*-[1,2,3]oxathiazolidin-3-yl)-methanone

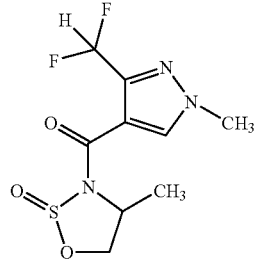

A solution of 14.6 ml SOCl$_2$ (200 mmol) in 98 ml dry acetonitrile under nitrogen atmosphere is cooled to −40° C. and 18.6 g 3-difluoromethyl-1-methyl-1H-pyrazole-4-carboxylic acid (2-hydroxy-1-methyl-ethyl)-amide (80 mmol) in 70 ml acetonitrile is added dropwise. 32.2 ml dry pyridine is added slowly. The mixture is then allowed to warm to ambient temperature and stirred for 1.5 h. The solvent volume is reduced to 100 ml, 200 ml ethylacetate is added and the resulting precipitate is filtered off. The filtrate is concentrated to an oil residue. Purification is achieved by filtration over 40 g silica gel with 400 ml ethylacetate to obtain 10.5 g (47% of theory) of 3-difluoromethyl-1-methyl-1H-pyrazol-4-yl)-4-methyl-2-oxo-2-λ-*4*-[1,2,3]oxathiazolidin-3-yl)-methanone in form of a resin.

MS [M+H]$^+$ 280.

c) Preparation of 3-difluoromethyl-1-methyl-1H-pyrazol-4-yl)-4-methyl-2,2-dioxo-2-λ-*6*-[1,2,3]oxathiazolidin-3-yl)-methanone

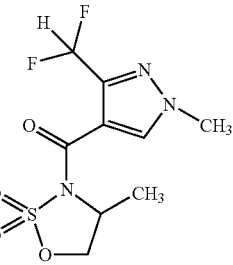

To a solution of 0.73 g 3-difluoromethyl-1-methyl-1H-pyrazol-4-yl)-4-methyl-2-oxo-2-λ-*4*-[1,2,3]oxathiazolidin-3-yl)-methanone (2.6 mmol) in 3.8 ml acetonitrile is added 0.85 mg ruthenium(III)chloride hydrate and 820 mg sodium(meta)periodate (3.8 mmol) at 0° C. 3.8 ml water is added dropwise. The reaction became exothermic up to 8° C. while cooling. The resulting dark suspension is allowed to warm to ambient temperature and stirred for 2 h, poured onto 40 ml water and extracted with ethylacetate (2×30 ml). The organic layer is dried over anhydrous sodium sulphate, filtered over 5 g silica gel and the solvent is removed to obtain 0.63 g (82% of theory) of 3-difluoromethyl-1-methyl-1H-pyrazol-4-yl)-4-methyl-2,2-dioxo-2-λ-*6*-[1,2,3]oxathiazolidin-3-yl)-methanone in form of a resin. The compound is used in example P1 without further purification $^1$H NMR (400 MHz, CDCl$_3$): δ 1.51-1.53 (d, 3H), 3.98 (s, 3H), 4.30-4.34+4.77-4.81 (m, 2H), 4.91-4.99 (m, 1H), 6.85-7.12 (t, 1H), 8.18 (s, 1H).

MS [M+H]$^+$ 296.

Example P6

Preparation of 2-(2,6-dimethyl-phenoxy)-1-methyl-ethylamine (compound Z1.166) and 2-(4-bromo-2,6-dimethyl-phenoxy)-1-methyl-ethylamine (compound Z1.168)

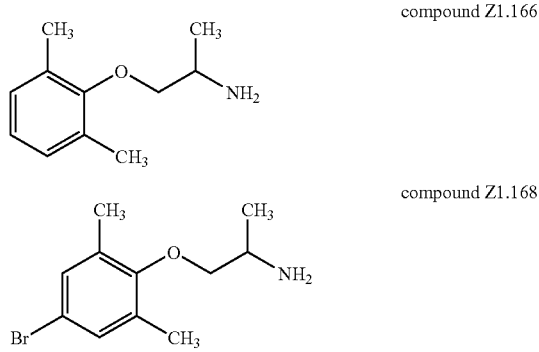

compound Z1.166 compound Z1.168

In a sulfonation flask 0.43 g mexiletine hydrochloride (CAS5370-01-4, 2 mol) is added to 10 ml glacial acetic acid. The resulting solution is cooled to 10° C. 0.32 g bromine (2 mmol) is added dropwise. The reaction mixture is stirred for 14 h at ambient temperature and poured onto ice-water. The pH of the mixture is adjusted to 10 with 5M NaOH and the mixture is extracted with ethyl acetate (2×30 ml). The combined ethyl acetate layers are washed with brine, dried over MgSO$_4$, filtered and dried under reduced pressure. 0.42 g of a 1:4-mixture of 2-(2,6-dimethyl-phenoxy)-1-methyl-ethylamine (compound Z1.166) and 2-(4-bromo-2,6-dimethyl-phenoxy)-1-methyl-ethylamine (compound Z1.168) is obtained in the form of a brown oil. The mixture is used in example P2 without further purification.

Example P7

1-Methyl-2-(2,4,6-tribromo-phenoxy)-ethylamine (compound Z1.193)

a) Preparation of 1-(2,4,6-tribromo-phenoxy)-propan-2-one

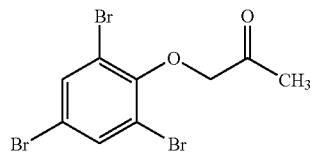

A mixture of 5 g 2,4,6-tribromophenol (15 mmol), 1.4 g 1-chloroacetone (15 mmol), 4.16 g anhydrous potassium carbonate (30 mmol) and 20 ml DMF is stirred at 27° C. Completion of the reaction is confirmed by TLC. The reaction mass is diluted with water and extracted with ethylacetate The organic layer is washed with water and brine, dried over anhydrous sodium sulphate and concentrated to obtain 5.6 g 1-(2,4,6-tribromo-phenoxy)-propan-2-one (97%).

$^1$H NMR (400 MHz, CDCl$_3$): –2.42 δ (s, 3H), 4.48 δ (s, 2H), 7.67 δ (s, 1H).

b) Preparation of 1-methyl-2-(2,4,6-tribromo-phenoxy)-ethylamine (compound Z1.193)

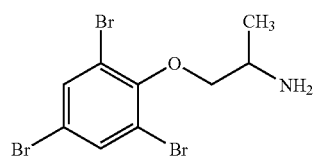

To a solution of 1 g 1-(2,4,6-tribromo-phenoxy)-propan-2-one (2.6 mmol) in 20 ml methanol is added 2.9 g ammonium acetate (39 mmol). The mixture is cooled to 0° C. and 0.81 g sodiumcyanoborohydride (13 mmol) is added. The reaction mixture is stirred overnight at ambient temperature. The completion of the reaction is confirmed by TLC. The reaction mixture is concentrated and the remaining residue is dissolved with 1.5 N HCl and washed with diethylether. The aqueous layer is neutralised and extracted with ethylacetate. The ethylacetate layer is dried over anhydrous sodium sulphate and the solvent removed. 0.32 g 1-methyl-2-(2,4,6-tribromo-phenoxy)-ethylamine (32%) is obtained.

LCMS—385.8/389.79/391.80

Example P8

Preparation of (S)-2-(2,6-dimethyl-phenoxy)-1-methyl-ethylamine hydrochloride (compound Z1.166 (S-enantiomere))

a) Preparation of (S)-4-Methyl-2-oxo-2-λ-*4*-[1,2,3]oxathiazolidine-3-carboxylic acid tert-butyl ester

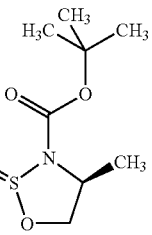

To a cooled (–50° C.) solution of SOCl$_2$ (53 ml, 77 mmol), imidazole (18.6 g, 274 mmol) and Et$_3$N (20.4 ml, 147 mmol) in anhydrous CH$_2$Cl$_2$ (550 mL) is added dropwise, a solution of (S)—N-Boc alaminol (12.0 g, 68 mmol) in anhydrous CH$_2$Cl$_2$ (150 mL) over 0.5 h. The mixture is then warmed to 0° C. and stirred for 4 h prior to the addition of water (600 mL). The organic portion is isolated, washed with brine (600 mL), dried (Na$_2$SO$_4$) and concentrated in vacuo to afford intermediate cyclic sulfamidite (15.14 g, 100%) as a colourless oil. This material is used immediately in the next stage without further purification.

b) Preparation of (S)-4-2,2-dioxo-2-λ-*6*-[1,2,3]oxathiazolidine-3-carboxylic acid tert-butyl ester

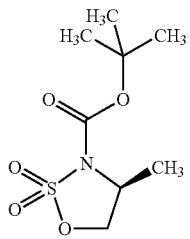

To an ice-cooled (0° C.) solution of intermediate cyclic sulfamidite from step a (15.14 g, 68 mmol) in MeCN (540 mL) is added sequentially NaIO$_4$ (72.0 g, 337 mmol), RuCl$_3$*H$_2$O (13 mg) and then water (420 mL). The mixture is stirred at 0° C. for 2 h and then diluted with water (900 mL) and extracted with Et$_2$O (2×1100 mL). The organic extracts are combined, washed with water (1200 mL) and then brine (1200 mL), dried (Na$_2$SO$_4$) and concentrated in vacuo. The residue is filtered through a pad of SiO$_2$ (60, eluting with Et$_2$O) to afford cyclic sulfamidate 4 (12.6 g, 78%, 4:1 rotamer ratio) as a colourless, crystalline solid; m.p. 112-120° C. (EtOAc-hexanes); $[\alpha]_{D25}$+5.29 (c=5.4, CHCl$_3$); $\delta_H$ (400 MHz, CDCl$_3$) (data for major rotamer only) 1.50 (3H, d, J=6.5, C4-CH$_3$), 1.53 (9H, s, NCO$_2$C(CH$_3$)$_3$), 4.00-4.10 (1H, m, C4-H), 4.68 (1H, dd, J=9.5 and 9.0, C3-H), 4.79 (1H, dd, J=9.0 and 7.0, C3-H).

c) Preparation of (S)-2-(2,6-dimethyl-phenoxy)-1-methyl-ethylamine hydrochloride (compound Z1.166 (S-enantiomere))

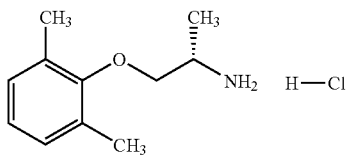

To a solution of 2,6-dimethylphenol (122 mg, 1.01 mmol) in anhydrous DMF (11 ml) is added NaH (50% dispersion in mineral oil, 50 mg, 1.01 mmol) and the resulting mixture is stirred at ambient temperature for 10 minutes. (S)-4-2,2-dioxo-2-λ-*6*-[1,2,3]oxathiazolidine-3-carboxylic acid tert-butyl ester (200 mg, 0.84 mmol) in anhydrous DMF (4 ml) is added and the mixture is stirred at r.t. for 3 h prior to concentration in vacuo. The residue is suspended in dioxane (6 ml), water (100 μL) and conc. H$_2$SO$_4$ (100 μL) are added and the mixture is stirred at ambient temperature for 0.5 h. Further conc. H$_2$SO$_4$ (100 μL) is added and the mixture is stirred at ambient temperature for another 0.5 h. The mixture is neutralised with saturated aq. NaHCO$_3$ and extracted with CH$_2$Cl$_2$ (3×30 mL). The combined organic extracts are concentrated in vacuo to afford crude amine (200 mg), as a brownish oil. This crude material is solved in diethylether (3 ml) and treated with 1 N HCl in diethylether to form a precipate. The solid is filtered of and dried in vacuo to afford (55 mg; 37%) of pure (S)-2-(2,6-dimethyl-phenoxy)-1-methyl-ethylamine hydrochloride in form of a white solid (mp. 190-193° C.). $[\alpha]_{D24}$+2.6 (c=1.0, MeOH).

The compound Z1.166 (S-enantiomere) is further transformed into compound 1.166 (S-enantiomere) by known methods.

Tables 1 to 7: Compounds of Formula IA

The invention is further illustrated by the preferred individual compounds of formula (IA) listed below in Tables 1 to 7. Characterising data is given in Table 12.

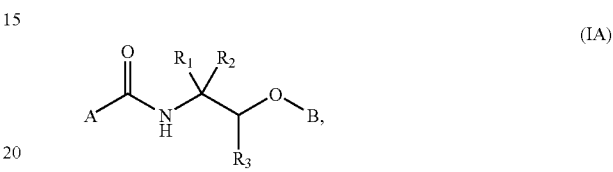

wherein

B is one of the preferred groups B1 to B26, B28 or B29:

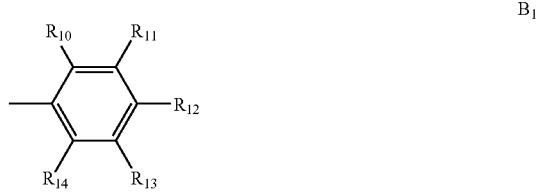

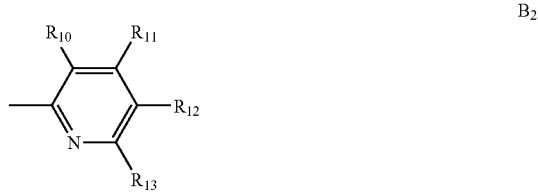

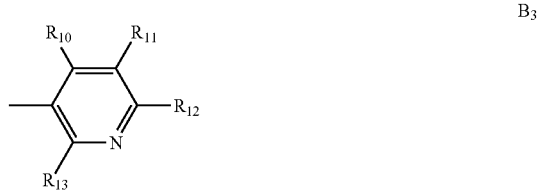

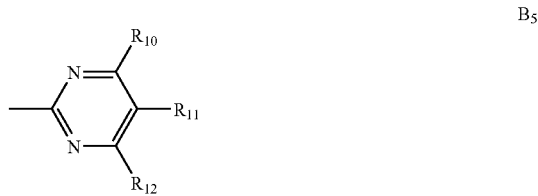

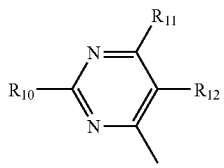
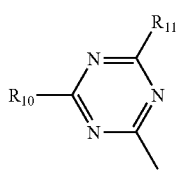
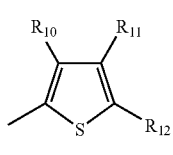
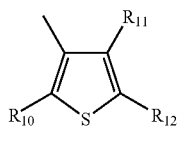
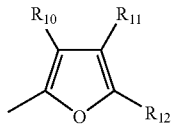
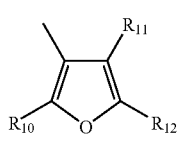
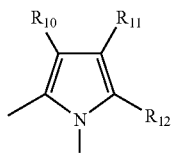
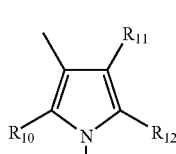
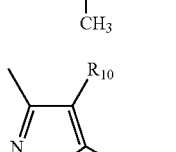
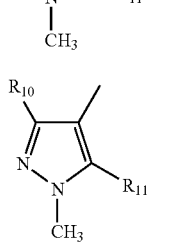
B6
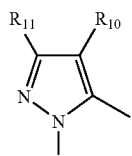
B7
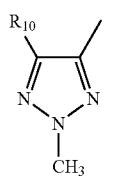
B8
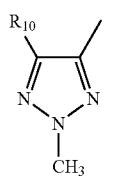
B9
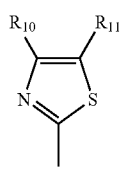
B10
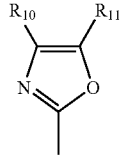
B11
B12
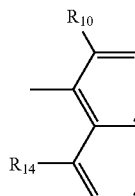
B13
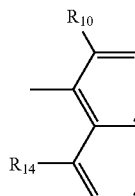
B14
B15
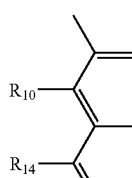
B16
B17
B18
B19
B20
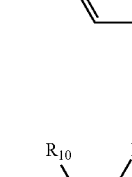
B21
B22

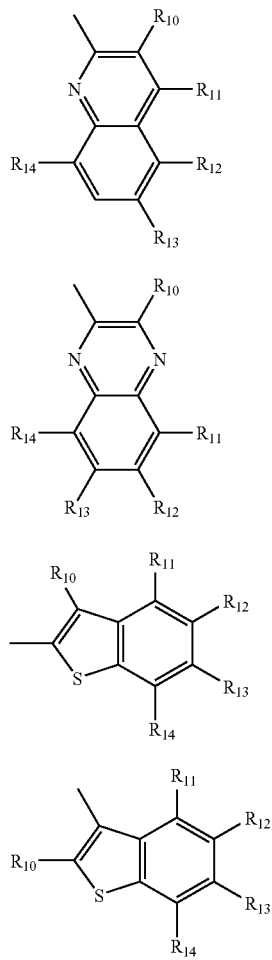

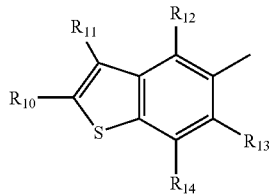

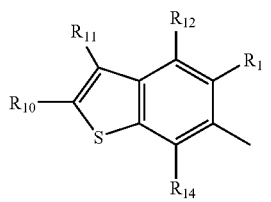

Each of Tables 1 to 7, which follow the Table Y below, comprises 643 compounds of the formula (IA) in which $R_1$, $R_2$, $R_3$, B, $R_{10}$, $R_{11}$, $R_{12}$, $R_{13}$ and $R_{14}$ and have the values given in Table Y and A has the value given in the relevant Table 1 to 7. Thus Table 1 corresponds to Table Y when Y is 1 and A has the value given under the Table 1 heading, Table 2 corresponds to Table Y when Y is 2 and A has the value given under the Table 2 heading, and so on for Tables 3 to 7.

In Tables 1 to 11 below "Me" stands for methyl, "Et" stands for ethyl, "i-Pr" stands for isopropyl, "c-Pr" stands for cyclopropyl and "t-Bu" stands for tertiary butyl.

TABLE Y

| Cpd No. | $R_2$ | $R_1$ | $R_3$ | B | $R_{10}$ | $R_{11}$ | $R_{12}$ | $R_{13}$ | $R_{14}$ |
|---|---|---|---|---|---|---|---|---|---|
| Y.001 | H | H | H | B1 | Cl | H | H | H | H |
| Y.002 | H | H | H | B1 | Cl | Cl | H | H | H |
| Y.003 | H | H | H | B1 | Cl | H | Cl | H | H |
| Y.004 | H | H | H | B1 | Cl | H | H | Cl | H |
| Y.005 | H | H | H | B1 | Cl | H | H | H | Cl |
| Y.006 | H | H | H | B1 | H | Cl | Cl | H | H |
| Y.007 | H | H | H | B1 | H | Cl | H | Cl | H |
| Y.008 | H | H | H | B1 | Cl | H | Cl | H | Cl |
| Y.009 | H | H | H | B1 | Cl | H | Br | H | Cl |
| Y.010 | H | H | H | B1 | Cl | H | I | H | Cl |
| Y.011 | H | H | H | B1 | Cl | H | $CHF_2$ | H | Cl |
| Y.012 | H | H | H | B1 | Cl | H | $CF_3$ | H | Cl |
| Y.013 | H | H | H | B1 | Cl | H | C≡C—H | H | Cl |
| Y.014 | H | H | H | B1 | Cl | H | C≡C—Me | H | Cl |
| Y.015 | H | H | H | B1 | Cl | H | C≡C—Si(Me)$_3$ | H | Cl |
| Y.016 | H | H | H | B1 | Cl | H | C≡C-t-Bu | H | Cl |
| Y.017 | H | H | H | B1 | Cl | H | C≡C-i-Pr | H | Cl |
| Y.018 | H | H | H | B1 | Cl | H | C≡C—CH$_2$OMe | H | Cl |
| Y.019 | H | H | H | B1 | Cl | H | C≡C-p-Cl-phenyl | H | Cl |
| Y.020 | H | H | H | B1 | Cl | H | p-Cl-phenyl | H | Cl |
| Y.021 | H | H | H | B1 | Cl | H | CHO | H | Cl |
| Y.022 | H | H | H | B1 | Cl | H | CH=NOMe | H | Cl |
| Y.023 | H | H | H | B1 | Cl | H | COMe | H | Cl |
| Y.024 | H | H | H | B1 | Cl | H | C(Me)=NOMe | H | Cl |
| Y.025 | H | H | H | B1 | Cl | H | $NO_2$ | H | Cl |
| Y.026 | H | H | H | B1 | Cl | H | $NH_2$ | H | Cl |
| Y.027 | H | H | H | B1 | Cl | H | NHMe | H | Cl |
| Y.028 | H | H | H | B1 | Cl | H | N(Me)$_2$ | H | Cl |
| Y.029 | H | H | H | B1 | Cl | H | NHCOMe | H | Cl |

TABLE Y-continued

| Cpd No. | R₂ | R₁ | R₃ | B | R₁₀ | R₁₁ | R₁₂ | R₁₃ | R₁₄ |
|---|---|---|---|---|---|---|---|---|---|
| Y.030 | H | H | H | B1 | Cl | H | N=CHNEt(Me) | H | Cl |
| Y.031 | H | H | H | B1 | Cl | H | OCF₃ | H | Cl |
| Y.032 | H | H | H | B1 | Cl | H | OCH₂CH=CHCl₂ | H | Cl |
| Y.033 | H | H | H | B1 | Cl | H | p-Cl-phenoxy | H | Cl |
| Y.034 | H | H | H | B1 | Cl | Me | Cl | H | Cl |
| Y.035 | H | H | H | B1 | Cl | Cl | Cl | H | Cl |
| Y.036 | H | H | H | B1 | Cl | H | Cl | Cl | Cl |
| Y.037 | H | H | H | B1 | Cl | Cl | Cl | Cl | Cl |
| Y.038 | H | H | H | B1 | Cl | H | H | H | Me |
| Y.039 | H | H | H | B1 | Cl | H | Cl | H | Me |
| Y.040 | H | H | H | B1 | Cl | H | Br | H | Me |
| Y.041 | H | H | H | B1 | Cl | H | CF₃ | H | Me |
| Y.042 | H | H | H | B1 | Cl | H | C≡C—H | H | Me |
| Y.043 | H | H | H | B1 | Cl | H | C≡C—CH₂OMe | H | Me |
| Y.044 | H | H | H | B1 | Cl | H | C(Me)=NOMe | H | Me |
| Y.045 | H | H | H | B1 | Cl | H | H | H | CHO |
| Y.046 | H | H | H | B1 | Cl | H | Cl | H | CHO |
| Y.047 | H | H | H | B1 | Cl | H | Br | H | CHO |
| Y.048 | H | H | H | B1 | Cl | H | CF₃ | H | CHO |
| Y.049 | H | H | H | B1 | Cl | H | C≡C—H | H | CHO |
| Y.050 | H | H | H | B1 | Cl | H | C≡C—CH₂OMe | H | CHO |
| Y.051 | H | H | H | B1 | Cl | H | C(Me)=NOMe | H | CHO |
| Y.052 | H | H | H | B1 | Cl | H | H | H | OMe |
| Y.053 | H | H | H | B1 | Cl | H | Cl | H | OMe |
| Y.054 | H | H | H | B1 | Cl | H | Br | H | OMe |
| Y.055 | H | H | H | B1 | Cl | H | CF₃ | H | OMe |
| Y.056 | H | H | H | B1 | Cl | H | C≡C—H | H | OMe |
| Y.057 | H | H | H | B1 | Cl | H | C≡C—CH₂OMe | H | OMe |
| Y.058 | H | H | H | B1 | Cl | H | C(Me)=NOMe | H | OMe |
| Y.059 | H | H | H | B1 | OMe | H | H | H | OMe |
| Y.060 | H | H | H | B1 | OMe | H | Cl | H | OMe |
| Y.061 | H | H | H | B1 | OMe | H | Br | H | OMe |
| Y.062 | H | H | H | B1 | OMe | H | CF₃ | H | OMe |
| Y.063 | H | H | H | B1 | OMe | H | C≡C—H | H | OMe |
| Y.064 | H | H | H | B1 | OMe | H | C≡C—CH₂OMe | H | OMe |
| Y.065 | H | H | H | B1 | OMe | H | C(Me)=NOMe | H | OMe |
| Y.066 | H | H | H | B1 | Me | H | H | H | Me |
| Y.067 | H | H | H | B1 | Me | H | Cl | H | Me |
| Y.068 | H | H | H | B1 | Me | H | Br | H | Me |
| Y.069 | H | H | H | B1 | Me | H | I | H | Me |
| Y.070 | H | H | H | B1 | Me | H | CF₃ | H | Me |
| Y.071 | H | H | H | B1 | Me | H | C≡C—H | H | Me |
| Y.072 | H | H | H | B1 | Me | H | Me | H | Me |
| Y.073 | H | H | H | B1 | Me | H | C≡C—CH₂OMe | H | Me |
| Y.074 | H | H | H | B1 | Me | H | C(Me)=NOMe | H | Me |
| Y.075 | H | H | H | B1 | Me | H | NO₂ | H | Me |
| Y.076 | H | H | H | B1 | Me | H | NH₂ | H | Me |
| Y.077 | H | H | H | B1 | Me | H | NHCOMe | H | Me |
| Y.078 | H | H | H | B1 | Me | H | p-Cl-phenyl | H | Me |
| Y.079 | H | H | H | B1 | Me | H | H | H | CHO |
| Y.080 | H | H | H | B1 | Me | H | Cl | H | CHO |
| Y.081 | H | H | H | B1 | Me | H | Br | H | CHO |
| Y.082 | H | H | H | B1 | i-Pr | H | H | H | i-Pr |
| Y.083 | H | H | H | B1 | i-Pr | H | Cl | H | i-Pr |
| Y.084 | H | H | H | B1 | i-Pr | H | Br | H | i-Pr |
| Y.085 | H | H | H | B1 | t-Bu | H | H | H | t-Bu |
| Y.086 | H | H | H | B1 | t-Bu | H | Cl | H | t-Bu |
| Y.087 | H | H | H | B1 | t-Bu | H | Br | H | t-Bu |
| Y.088 | H | H | H | B1 | t-Bu | H | Me | H | t-Bu |
| Y.089 | H | H | H | B1 | t-Bu | H | t-Bu | H | t-Bu |
| Y.090 | H | H | H | B1 | t-Bu | H | OMe | H | t-Bu |
| Y.091 | H | H | H | B1 | Br | H | H | H | Br |
| Y.092 | H | H | H | B1 | Br | H | Br | H | Br |
| Y.093 | H | H | H | B1 | F | H | H | H | F |
| Y.094 | H | H | H | B1 | F | H | Cl | H | F |
| Y.095 | H | H | H | B1 | F | H | Br | H | F |
| Y.096 | H | H | H | B1 | I | H | H | H | I |
| Y.097 | H | H | H | B1 | I | H | Cl | H | I |
| Y.098 | H | Me | H | B1 | H | H | COMe | H | H |
| Y.099 | H | Me | H | B1 | H | H | F | F | H |
| Y.100 | H | Me | H | B1 | Me | H | Cl | H | H |
| Y.101 | H | Me | H | B1 | H | Cl | Cl | H | H |
| Y.102 | H | Me | H | B1 | H | t-Bu | H | t-Bu | H |
| Y.103 | H | Me | H | B1 | Cl | H | Cl | H | H |
| Y.104 | H | Me | H | B1 | Cl | H | H | Cl | H |
| Y.105 | H | Me | H | B1 | Cl | H | H | H | Cl |
| Y.106 | H | Me | H | B1 | H | Cl | Cl | H | H |
| Y.107 | H | Me | H | B1 | H | Cl | H | Cl | H |

TABLE Y-continued

| Cpd No. | R$_2$ | R$_1$ | R$_3$ | B | R$_{10}$ | R$_{11}$ | R$_{12}$ | R$_{13}$ | R$_{14}$ |
|---|---|---|---|---|---|---|---|---|---|
| Y.108 | H | Me | H | B1 | Cl | H | Cl | H | Cl |
| Y.109 | H | Me | H | B1 | Cl | H | Br | H | Cl |
| Y.110 | H | Me | H | B1 | Cl | H | I | H | Cl |
| Y.111 | H | Me | H | B1 | Cl | H | CHF$_2$ | H | Cl |
| Y.112 | H | Me | H | B1 | Cl | H | CF$_3$ | H | Cl |
| Y.113 | H | Me | H | B1 | Cl | H | C≡C—H | H | Cl |
| Y.114 | H | Me | H | B1 | Cl | H | C≡C—Me | H | Cl |
| Y.115 | H | Me | H | B1 | Cl | H | C≡C—Si(Me)$_3$ | H | Cl |
| Y.116 | H | Me | H | B1 | Cl | H | C≡C-t-Bu | H | Cl |
| Y.117 | H | Me | H | B1 | Cl | H | C≡C—C-i-Pr | H | Cl |
| Y.118 | H | Me | H | B1 | Cl | H | C≡C—CH$_2$OMe | H | Cl |
| Y.119 | H | Me | H | B1 | Cl | H | C≡C-p-Cl-phenyl | H | Cl |
| Y.120 | H | Me | H | B1 | Cl | H | p-Cl-phenyl | H | Cl |
| Y.121 | H | Me | H | B1 | Cl | H | CHO | H | Cl |
| Y.122 | H | Me | H | B1 | Cl | H | CH═NOMe | H | Cl |
| Y.123 | H | Me | H | B1 | Cl | H | COMe | H | Cl |
| Y.124 | H | Me | H | B1 | Cl | H | C(Me)═NOMe | H | Cl |
| Y.125 | H | Me | H | B1 | Cl | H | NO$_2$ | H | Cl |
| Y.126 | H | Me | H | B1 | Cl | H | NH$_2$ | H | Cl |
| Y.127 | H | Me | H | B1 | Cl | H | NHMe | H | Cl |
| Y.128 | H | Me | H | B1 | Cl | H | N(Me)$_2$ | H | Cl |
| Y.129 | H | Me | H | B1 | Cl | H | NHCOMe | H | Cl |
| Y.130 | H | Me | H | B1 | Cl | H | N═CHNEt(Me) | H | Cl |
| Y.131 | H | Me | H | B1 | Cl | H | OCF$_3$ | H | Cl |
| Y.132 | H | Me | H | B1 | Cl | H | OCH$_2$CH═CHCl$_2$ | H | Cl |
| Y.133 | H | Me | H | B1 | Cl | H | p-Cl-phenoxy | H | Cl |
| Y.134 | H | Me | H | B1 | Cl | Me | Cl | H | Cl |
| Y.135 | H | Me | H | B1 | Cl | Cl | Cl | H | Cl |
| Y.136 | H | Me | H | B1 | Cl | H | Cl | Cl | Cl |
| Y.137 | H | Me | H | B1 | Cl | Cl | Cl | Cl | Cl |
| Y.138 | H | Me | H | B1 | Cl | H | H | H | Me |
| Y.139 | H | Me | H | B1 | Cl | H | Cl | H | Me |
| Y.140 | H | Me | H | B1 | Cl | H | Br | H | Me |
| Y.141 | H | Me | H | B1 | Cl | H | CF$_3$ | H | Me |
| Y.142 | H | Me | H | B1 | Cl | H | C≡C—H | H | Me |
| Y.143 | H | Me | H | B1 | Cl | H | C≡C—CH$_2$OMe | H | Me |
| Y.144 | H | Me | H | B1 | Cl | H | C(Me)═NOMe | H | Me |
| Y.145 | H | Me | H | B1 | Cl | H | H | H | CHO |
| Y.146 | H | Me | H | B1 | Cl | H | Cl | H | CHO |
| Y.147 | H | Me | H | B1 | Cl | H | Br | H | CHO |
| Y.148 | H | Me | H | B1 | Cl | H | CF$_3$ | H | CHO |
| Y.149 | H | Me | H | B1 | Cl | H | C≡C—H | H | CHO |
| Y.150 | H | Me | H | B1 | Cl | H | C≡C—CH$_2$OMe | H | CHO |
| Y.151 | H | Me | H | B1 | Cl | H | C(Me)═NOMe | H | CHO |
| Y.152 | H | Me | H | B1 | Cl | H | H | H | OMe |
| Y.153 | H | Me | H | B1 | Cl | H | Cl | H | OMe |
| Y.154 | H | Me | H | B1 | Cl | H | Br | H | OMe |
| Y.155 | H | Me | H | B1 | Cl | H | CF$_3$ | H | OMe |
| Y.156 | H | Me | H | B1 | Cl | H | C≡C—H | H | OMe |
| Y.157 | H | Me | H | B1 | Cl | H | C≡C—CH$_2$OMe | H | OMe |
| Y.158 | H | Me | H | B1 | Cl | H | C(Me)═NOMe | H | OMe |
| Y.159 | H | Me | H | B1 | OMe | H | H | H | OMe |
| Y.160 | H | Me | H | B1 | OMe | H | Cl | H | OMe |
| Y.161 | H | Me | H | B1 | OMe | H | Br | H | OMe |
| Y.162 | H | Me | H | B1 | OMe | H | CF$_3$ | H | OMe |
| Y.163 | H | Me | H | B1 | OMe | H | C≡C—H | H | OMe |
| Y.164 | H | Me | H | B1 | OMe | H | C≡C—CH$_2$OMe | H | OMe |
| Y.165 | H | Me | H | B1 | OMe | H | C(Me)═NOMe | H | OMe |
| Y.166 | H | Me | H | B1 | Me | H | H | H | Me |
| Y.167 | H | Me | H | B1 | Me | H | Cl | H | Me |
| Y.168 | H | Me | H | B1 | Me | H | Br | H | Me |
| Y.169 | H | Me | H | B1 | Me | H | I | H | Me |
| Y.170 | H | Me | H | B1 | Me | H | CF$_3$ | H | Me |
| Y.171 | H | Me | H | B1 | Me | H | C≡C—H | H | Me |
| Y.172 | H | Me | H | B1 | Me | H | Me | H | Me |
| Y.173 | H | Me | H | B1 | Me | H | C≡C—CH$_2$OMe | H | Me |
| Y.174 | H | Me | H | B1 | Me | H | C(Me)═NOMe | H | Me |
| Y.175 | H | Me | H | B1 | Me | H | NO$_2$ | H | Me |
| Y.176 | H | Me | H | B1 | Me | H | NH$_2$ | H | Me |
| Y.177 | H | Me | H | B1 | Me | H | NHCOMe | H | Me |
| Y.178 | H | Me | H | B1 | Me | H | p-Cl-phenyl | H | Me |
| Y.179 | H | Me | H | B1 | Me | H | H | H | CHO |
| Y.180 | H | Me | H | B1 | Me | H | Cl | H | CHO |
| Y.181 | H | Me | H | B1 | Me | H | Br | H | CHO |
| Y.182 | H | Me | H | B1 | i-Pr | H | H | H | i-Pr |
| Y.183 | H | Me | H | B1 | i-Pr | H | Cl | H | i-Pr |
| Y.184 | H | Me | H | B1 | i-Pr | H | Br | H | i-Pr |
| Y.185 | H | Me | H | B1 | t-Bu | H | H | H | t-Bu |

TABLE Y-continued

| Cpd No. | R₂ | R₁ | R₃ | B | R₁₀ | R₁₁ | R₁₂ | R₁₃ | R₁₄ |
|---|---|---|---|---|---|---|---|---|---|
| Y.186 | H | Me | H | B1 | t-Bu | H | Cl | H | t-Bu |
| Y.187 | H | Me | H | B1 | t-Bu | H | Me | H | t-Bu |
| Y.188 | H | Me | H | B1 | t-Bu | H | t-Bu | H | t-Bu |
| Y.189 | H | Me | H | B1 | t-Bu | H | p-Cl-phenyl | H | t-Bu |
| Y.190 | H | Me | H | B1 | H | H | CF₃ | H | H |
| Y.191 | H | Me | H | B1 | H | H | Br | H | H |
| Y.192 | H | Me | H | B1 | Br | H | H | H | Br |
| Y.193 | H | Me | H | B1 | Br | H | Br | H | Br |
| Y.194 | H | Me | H | B1 | F | H | H | H | F |
| Y.195 | H | Me | H | B1 | F | H | Cl | H | F |
| Y.196 | H | Me | H | B1 | F | H | Br | H | F |
| Y.197 | H | Me | H | B1 | I | H | H | H | I |
| Y.198 | H | Me | H | B1 | I | H | Cl | H | I |
| Y.199 | H | Me | H | B1 | I | H | Br | H | I |
| Y.200 | H | Me | H | B1 | I | H | I | H | I |
| Y.201 | H | Me | Me | B1 | Cl | H | H | H | Cl |
| Y.202 | H | Me | Me | B1 | Cl | H | Cl | H | Cl |
| Y.203 | H | Me | Me | B1 | Br | H | H | H | Br |
| Y.204 | H | Me | Me | B1 | Br | H | Br | H | Br |
| Y.205 | H | Me | Me | B1 | Me | H | H | H | Me |
| Y.206 | H | Me | Me | B1 | Me | H | Cl | H | Me |
| Y.207 | H | Me | Me | B1 | Me | H | Br | H | Me |
| Y.208 | H | Me | H | B1 | Cl | H | H | H | Cl |
| Y.209 | Me | Me | H | B1 | Cl | H | Cl | H | Cl |
| Y.210 | Me | Me | H | B1 | Br | H | H | H | Br |
| Y.211 | Me | Me | H | B1 | Br | H | Br | H | Br |
| Y.212 | Me | Me | H | B1 | Me | H | Cl | H | Me |
| Y.213 | Me | Me | H | B1 | Me | H | Br | H | Me |
| Y.214 | i-Pr | Me | H | B1 | Me | H | H | H | Me |
| Y.215 | c-Pr | Me | H | B1 | Me | H | H | H | Me |
| Y.216 | Et | Et | H | B1 | Me | H | H | H | Me |
| Y.217 | Et | Et | H | B1 | Me | H | Br | H | Me |
| Y.218 | CH₂CH₂ | | H | B1 | Cl | H | H | H | H |
| Y.219 | CH₂CH₂ | | H | B1 | Me | H | H | H | Me |
| Y.220 | CH₂CH₂ | | H | B1 | Me | H | Br | H | Me |
| Y.221 | CH₂CH₂ | | H | B1 | H | H | Cl | H | H |
| Y.222 | CH₂CH₂ | | H | B1 | Cl | H | Cl | H | H |
| Y.223 | CH₂CH₂ | | H | B1 | Cl | H | H | H | Cl |
| Y.224 | CH₂CH₂ | | H | B1 | Cl | H | Cl | H | Cl |
| Y.225 | CH₂CH₂ | | H | B1 | Br | H | H | H | Br |
| Y.226 | CH₂CH₂ | | H | B1 | Br | H | Br | H | Br |
| Y.227 | H | CH₂ | | B1 | Me | H | H | H | Me |
| Y.228 | H | CH₂ | | B1 | Me | H | Br | H | Me |
| Y.229 | H | CH₂ | | B1 | H | H | Cl | H | H |
| Y.230 | H | CH₂ | | B1 | Cl | H | Cl | H | H |
| Y.231 | H | CH₂ | | B1 | Cl | H | H | H | Cl |
| Y.232 | H | CH₂ | | B1 | Cl | H | Cl | H | Cl |
| Y.233 | H | CH₂ | | B1 | Br | H | H | H | Br |
| Y.234 | H | CH₂ | | B1 | Br | H | Br | H | Br |
| Y.235 | H | H | H | B2 | Cl | H | Cl | H | — |
| Y.236 | H | H | H | B2 | Cl | H | Br | H | — |
| Y.237 | H | H | H | B2 | Br | H | Br | H | — |
| Y.238 | H | H | H | B2 | Cl | H | CF₃ | H | — |
| Y.239 | H | Me | H | B2 | Cl | H | CF₃ | H | — |
| Y.240 | H | Et | H | B2 | Cl | H | CF₃ | H | — |
| Y.241 | Me | Me | H | B2 | Cl | H | CF₃ | H | — |
| Y.242 | H | H | Me | B2 | Cl | H | CF₃ | H | — |
| Y.243 | H | Et | H | B2 | Cl | H | CF₃ | H | — |
| Y.244 | CH₂CH₂ | | H | B2 | Cl | H | CF₃ | H | — |
| Y.245 | H | CH₂ | | B2 | Cl | H | CF₃ | H | — |
| Y.246 | H | H | H | B3 | Cl | H | H | Cl | — |
| Y.247 | H | H | H | B3 | Cl | H | H | Br | — |
| Y.248 | H | H | H | B3 | Cl | H | H | I | — |
| Y.249 | H | H | H | B3 | Cl | H | H | Me | — |
| Y.250 | H | H | H | B3 | Me | H | H | Cl | — |
| Y.251 | H | H | H | B3 | Me | H | H | Br | — |
| Y.252 | H | H | H | B3 | Me | H | H | Me | — |
| Y.253 | H | Me | H | B3 | Cl | H | H | Cl | — |
| Y.254 | H | Me | H | B3 | Me | H | H | Cl | — |
| Y.255 | H | H | H | B4 | Cl | H | H | Cl | — |
| Y.256 | H | H | H | B4 | Br | H | H | Br | — |
| Y.247 | H | H | H | B4 | Me | H | H | Me | — |
| Y.258 | H | Me | H | B4 | Cl | H | H | Cl | — |
| Y.259 | H | Me | H | B4 | Br | H | H | Br | — |
| Y.260 | H | Me | H | B4 | Me | H | H | Me | — |
| Y.261 | H | H | H | B5 | Me | H | Me | — | — |
| Y.262 | H | H | H | B5 | Me | H | Me | — | — |
| Y.263 | H | H | H | B5 | H | Me | H | — | — |

TABLE Y-continued

| Cpd No. | R₂ | R₁ | R₃ | B | R₁₀ | R₁₁ | R₁₂ | R₁₃ | R₁₄ |
|---|---|---|---|---|---|---|---|---|---|
| Y.264 | H | H | H | B5 | H | Cl | H | — | — |
| Y.265 | H | H | H | B5 | H | Br | H | — | — |
| Y.266 | H | H | H | B5 | H | CF₃ | H | — | — |
| Y.267 | H | Me | H | B5 | Me | H | Me | — | — |
| Y.268 | H | Me | H | B5 | Me | H | Me | — | — |
| Y.269 | H | Me | H | B5 | H | Me | H | — | — |
| Y.270 | H | Me | H | B5 | H | Cl | H | — | — |
| Y.271 | H | Me | H | B5 | H | Br | H | — | — |
| Y.272 | H | Me | H | B5 | H | CF₃ | H | — | — |
| Y.273 | H | H | H | B6 | Cl | H | Cl | — | — |
| Y.274 | H | H | H | B6 | Cl | Cl | Cl | — | — |
| Y.275 | H | H | H | B6 | Cl | Me | Cl | — | — |
| Y.276 | H | Me | H | B6 | Cl | H | Cl | — | — |
| Y.277 | H | Me | H | B6 | Cl | Cl | Cl | — | — |
| Y.278 | H | Me | H | B6 | Cl | Me | Cl | — | — |
| Y.279 | H | H | H | B7 | Cl | H | — | — | — |
| Y.280 | H | H | H | B7 | Cl | Cl | — | — | — |
| Y.281 | H | H | H | B7 | Me | Me | — | — | — |
| Y.282 | H | H | H | B7 | OMe | Me | — | — | — |
| Y.283 | H | H | H | B7 | OMe | Cl | — | — | — |
| Y.284 | H | H | H | B7 | NHMe | Cl | — | — | — |
| Y.285 | H | Me | H | B7 | Cl | H | — | — | — |
| Y.286 | H | Me | H | B7 | Cl | Cl | — | — | — |
| Y.287 | H | Me | H | B7 | Me | Me | — | — | — |
| Y.288 | H | Me | H | B7 | OMe | Me | — | — | — |
| Y.289 | H | Me | H | B7 | OMe | Cl | — | — | — |
| Y.290 | H | Me | H | B7 | NHMe | Cl | — | — | — |
| Y.291 | H | H | H | B8 | Cl | H | H | — | — |
| Y.292 | H | H | H | B8 | Cl | Cl | H | — | — |
| Y.293 | H | H | H | B8 | Cl | Cl | Cl | — | — |
| Y.294 | H | H | H | B8 | Cl | H | Cl | — | — |
| Y.295 | H | H | H | B8 | Me | H | H | — | — |
| Y.296 | H | H | H | B8 | Me | Cl | H | — | — |
| Y.297 | H | H | H | B8 | Me | Cl | Cl | — | — |
| Y.298 | H | H | H | B8 | Me | Me | H | — | — |
| Y.299 | H | H | H | B8 | Me | H | Me | — | — |
| Y.300 | H | H | H | B8 | Me | Me | Cl | — | — |
| Y.301 | H | H | H | B8 | Me | Me | Me | — | — |
| Y.302 | H | Me | H | B8 | Cl | H | H | — | — |
| Y.303 | H | Me | H | B8 | Cl | Cl | H | — | — |
| Y.304 | H | Me | H | B8 | Cl | Cl | Cl | — | — |
| Y.305 | H | Me | H | B8 | Cl | H | Cl | — | — |
| Y.306 | H | Me | H | B8 | Me | H | H | — | — |
| Y.307 | H | Me | H | B8 | Me | Cl | H | — | — |
| Y.308 | H | Me | H | B8 | Me | Cl | Cl | — | — |
| Y.309 | H | Me | H | B8 | Me | Me | H | — | — |
| Y.310 | H | Me | H | B8 | Me | H | Me | — | — |
| Y.311 | H | Me | H | B8 | Me | Me | Cl | — | — |
| Y.312 | H | Me | H | B8 | Me | Me | Me | — | — |
| Y.313 | H | H | H | B9 | Cl | Cl | H | — | — |
| Y.314 | H | H | H | B9 | Cl | Cl | H | — | — |
| Y.315 | H | H | H | B9 | Cl | Cl | Cl | — | — |
| Y.316 | H | H | H | B9 | Cl | Me | H | — | — |
| Y.317 | H | H | H | B9 | Cl | Me | Cl | — | — |
| Y.318 | H | H | H | B9 | Cl | Me | Me | — | — |
| Y.319 | H | H | H | B9 | Cl | Cl | Me | — | — |
| Y.320 | H | H | H | B9 | Me | Cl | H | — | — |
| Y.321 | H | H | H | B9 | Me | Cl | Cl | — | — |
| Y.322 | H | H | H | B9 | Me | Cl | Me | — | — |
| Y.323 | H | H | H | B9 | Me | Me | H | — | — |
| Y.324 | H | H | H | B9 | Me | Me | Cl | — | — |
| Y.325 | H | H | H | B9 | Me | Me | Me | — | — |
| Y.326 | H | Me | H | B9 | Cl | Cl | H | — | — |
| Y.327 | H | Me | H | B9 | Cl | Cl | Cl | — | — |
| Y.328 | H | Me | H | B9 | Cl | Me | H | — | — |
| Y.329 | H | Me | H | B9 | Cl | Me | Cl | — | — |
| Y.330 | H | Me | H | B9 | Cl | Me | Me | — | — |
| Y.331 | H | Me | H | B9 | Cl | Cl | Me | — | — |
| Y.332 | H | Me | H | B9 | Me | Cl | H | — | — |
| Y.333 | H | Me | H | B9 | Me | Cl | Cl | — | — |
| Y.334 | H | Me | H | B9 | Me | Cl | Me | — | — |
| Y.335 | H | Me | H | B9 | Me | Me | H | — | — |
| Y.336 | H | Me | H | B9 | Me | Me | Cl | — | — |
| Y.337 | H | Me | H | B9 | Me | Me | Me | — | — |
| Y.338 | H | H | H | B10 | Cl | H | H | — | — |
| Y.339 | H | H | B | B10 | Cl | Cl | H | — | — |
| Y.340 | H | H | H | B10 | Cl | Cl | Cl | — | — |
| Y.341 | H | H | H | B10 | Cl | H | Cl | — | — |

TABLE Y-continued

| Cpd No. | R₂ | R₁ | R₃ | B | R₁₀ | R₁₁ | R₁₂ | R₁₃ | R₁₄ |
|---|---|---|---|---|---|---|---|---|---|
| Y.342 | H | H | H | B10 | Me | H | H | — | — |
| Y.343 | H | H | H | B10 | Me | Cl | H | — | — |
| Y.344 | H | H | H | B10 | Me | Cl | Cl | — | — |
| Y.345 | H | H | H | B10 | Me | Me | H | — | — |
| Y.346 | H | H | H | B10 | Me | H | Me | — | — |
| Y.347 | H | H | H | B10 | Me | Me | Cl | — | — |
| Y.348 | H | H | H | B10 | Me | Me | Me | — | — |
| Y.349 | H | Me | H | B10 | Cl | H | H | — | — |
| Y.350 | H | Me | H | B10 | Cl | Cl | H | — | — |
| Y.351 | H | Me | H | B10 | Cl | Cl | Cl | — | — |
| Y.352 | H | Me | H | B10 | Cl | H | Cl | — | — |
| Y.353 | H | Me | H | B10 | Me | H | H | — | — |
| Y.354 | H | Me | H | B10 | Me | Cl | H | — | — |
| Y.355 | H | Me | H | B10 | Me | Cl | Cl | — | — |
| Y.356 | H | Me | H | B10 | Me | Me | H | — | — |
| Y.347 | H | Me | H | B10 | Me | H | Me | — | — |
| Y.358 | H | Me | H | B10 | Me | Me | Cl | — | — |
| Y.359 | H | Me | H | B10 | Me | Me | Me | — | — |
| Y.360 | H | H | H | B11 | Cl | Cl | H | — | — |
| Y.361 | H | H | H | B11 | Cl | Cl | H | — | — |
| Y.362 | H | H | H | B11 | Cl | Cl | Cl | — | — |
| Y.363 | H | H | H | B11 | Cl | Me | H | — | — |
| Y.364 | H | H | H | B11 | Cl | Me | Cl | — | — |
| Y.365 | H | H | H | B11 | Cl | Me | Me | — | — |
| Y.366 | H | H | H | B11 | Cl | Cl | Me | — | — |
| Y.367 | H | H | H | B11 | Me | Cl | H | — | — |
| Y.368 | H | H | H | B11 | Me | Cl | Cl | — | — |
| Y.369 | H | H | H | B11 | Me | Cl | Me | — | — |
| Y.370 | H | H | H | B11 | Me | Me | H | — | — |
| Y.371 | H | H | H | B11 | Me | Me | Cl | — | — |
| Y.372 | H | H | H | B11 | Me | Me | Me | — | — |
| Y.373 | H | Me | H | B11 | Cl | Cl | H | — | — |
| Y.374 | H | Me | H | B11 | Cl | Cl | Cl | — | — |
| Y.375 | H | Me | H | B11 | Cl | Me | H | — | — |
| Y.376 | H | Me | H | B11 | Cl | Me | Cl | — | — |
| Y.377 | H | Me | H | B11 | Cl | Me | Me | — | — |
| Y.378 | H | Me | H | B11 | Cl | Cl | Me | — | — |
| Y.379 | H | Me | H | B11 | Me | Cl | H | — | — |
| Y.380 | H | Me | H | B11 | Me | Cl | Cl | — | — |
| Y.381 | H | Me | H | B11 | Me | Cl | Me | — | — |
| Y.382 | H | Me | H | B11 | Me | Me | H | — | — |
| Y.383 | H | Me | H | B11 | Me | Me | Cl | — | — |
| Y.384 | H | Me | H | B11 | Me | Me | Me | — | — |
| Y.385 | H | H | H | B12 | Cl | H | H | — | — |
| Y.386 | H | H | H | B12 | Cl | Cl | H | — | — |
| Y.387 | H | H | H | B12 | Cl | Cl | Cl | — | — |
| Y.388 | H | H | H | B12 | Cl | H | Cl | — | — |
| Y.389 | H | H | H | B12 | Me | H | H | — | — |
| Y.390 | H | H | H | B12 | Me | Cl | H | — | — |
| Y.391 | H | H | H | B12 | Me | Cl | Cl | — | — |
| Y.392 | H | H | H | B12 | Me | Me | H | — | — |
| Y.393 | H | H | H | B12 | Me | H | Me | — | — |
| Y.394 | H | H | H | B12 | Me | Me | Cl | — | — |
| Y.395 | H | H | H | B12 | Me | Me | Me | — | — |
| Y.396 | H | Me | H | B12 | Cl | H | H | — | — |
| Y.397 | H | Me | H | B12 | Cl | Cl | H | — | — |
| Y.398 | H | Me | H | B12 | Cl | Cl | Cl | — | — |
| Y.399 | H | Me | H | B12 | Cl | H | Cl | — | — |
| Y.400 | H | Me | H | B12 | Me | H | H | — | — |
| Y.401 | H | Me | H | B12 | Me | Cl | H | — | — |
| Y.402 | H | Me | H | B12 | Me | Cl | Cl | — | — |
| Y.403 | H | Me | H | B12 | Me | Me | H | — | — |
| Y.404 | H | Me | H | B12 | Me | H | Me | — | — |
| Y.405 | H | Me | H | B12 | Me | Me | Cl | — | — |
| Y.406 | H | Me | H | B12 | Me | Me | Me | — | — |
| Y.407 | H | H | H | B13 | Cl | Cl | H | — | — |
| Y.408 | H | H | H | B13 | Cl | Cl | H | — | — |
| Y.409 | H | H | H | B13 | Cl | Cl | Cl | — | — |
| Y.410 | H | H | H | B13 | Cl | Me | H | — | — |
| Y.411 | H | H | H | B13 | Cl | Me | Cl | — | — |
| Y.412 | H | H | H | B13 | Cl | Me | Me | — | — |
| Y.413 | H | H | H | B13 | Cl | Cl | Me | — | — |
| Y.414 | H | H | H | B13 | Me | Cl | H | — | — |
| Y.415 | H | H | H | B13 | Me | Cl | Cl | — | — |
| Y.416 | H | H | H | B13 | Me | Cl | Me | — | — |
| Y.417 | H | H | H | B13 | Me | Me | H | — | — |
| Y.418 | H | H | H | B13 | Me | Me | Cl | — | — |
| Y.419 | H | H | H | B13 | Me | Me | Me | — | — |

TABLE Y-continued

| Cpd No. | R₂ | R₁ | R₃ | B | R₁₀ | R₁₁ | R₁₂ | R₁₃ | R₁₄ |
|---|---|---|---|---|---|---|---|---|---|
| Y.420 | H | Me | H | B13 | Cl | Cl | H | — | — |
| Y.421 | H | Me | H | B13 | Cl | Cl | Cl | — | — |
| Y.422 | H | Me | H | B13 | Cl | Me | H | — | — |
| Y.423 | H | Me | H | B13 | Cl | Me | Cl | — | — |
| Y.424 | H | Me | H | B13 | Cl | Me | Me | — | — |
| Y.425 | H | Me | H | B13 | Cl | Cl | Me | — | — |
| Y.426 | H | Me | H | B13 | Me | Cl | H | — | — |
| Y.427 | H | Me | H | B13 | Me | Cl | Cl | — | — |
| Y.428 | H | Me | H | B13 | Me | Cl | Me | — | — |
| Y.429 | H | Me | H | B13 | Me | Me | H | — | — |
| Y.430 | H | Me | H | B13 | Me | Me | Cl | — | — |
| Y.431 | H | Me | H | B13 | Me | Me | Me | — | — |
| Y.432 | H | H | H | B14 | Cl | H | — | — | — |
| Y.433 | H | H | H | B14 | Cl | Me | — | — | — |
| Y.434 | H | H | H | B14 | Br | H | — | — | — |
| Y.435 | H | H | H | B14 | Br | Me | — | — | — |
| Y.436 | H | H | H | B14 | Me | H | — | — | — |
| Y.437 | H | H | H | B14 | Me | Me | — | — | — |
| Y.438 | H | H | H | B14 | CF₃ | H | — | — | — |
| Y.439 | H | H | H | B14 | CF₃ | Me | — | — | — |
| Y.440 | H | H | H | B14 | OMe | H | — | — | — |
| Y.441 | H | H | H | B14 | OMe | Me | — | — | — |
| Y.442 | H | Me | H | B14 | Cl | H | — | — | — |
| Y.443 | H | Me | H | B14 | Cl | Me | — | — | — |
| Y.444 | H | Me | H | B14 | Br | H | — | — | — |
| Y.445 | H | Me | H | B14 | Br | Me | — | — | — |
| Y.446 | H | Me | H | B14 | Me | H | — | — | — |
| Y.447 | H | Me | H | B14 | Me | Me | — | — | — |
| Y.448 | H | Me | H | B14 | CF₃ | H | — | — | — |
| Y.449 | H | Me | H | B14 | CF₃ | Me | — | — | — |
| Y.450 | H | Me | H | B14 | OMe | H | — | — | — |
| Y.451 | H | Me | H | B14 | OMe | Me | — | — | — |
| Y.452 | H | H | H | B15 | Cl | Cl | — | — | — |
| Y.453 | H | H | H | B15 | Me | Me | — | — | — |
| Y.454 | H | H | H | B15 | Br | Br | — | — | — |
| Y.455 | H | H | H | B15 | CF₃ | CF₃ | — | — | — |
| Y.456 | H | H | H | B15 | OMe | Cl | — | — | — |
| Y.457 | H | Me | H | B15 | Cl | Cl | — | — | — |
| Y.458 | H | Me | H | B15 | Me | Me | — | — | — |
| Y.459 | H | Me | H | B15 | Br | Br | — | — | — |
| Y.460 | H | Me | H | B15 | CF₃ | CF₃ | — | — | — |
| Y.461 | H | Me | H | B15 | OMe | Cl | — | — | — |
| Y.462 | H | H | H | B16 | Cl | H | — | — | — |
| Y.463 | H | H | H | B16 | Cl | Cl | — | — | — |
| Y.464 | H | H | H | B16 | Br | H | — | — | — |
| Y.465 | H | H | H | B16 | Br | Br | — | — | — |
| Y.466 | H | H | H | B16 | Me | H | — | — | — |
| Y.467 | H | H | H | B16 | Me | Me | — | — | — |
| Y.468 | H | H | H | B16 | CF₃ | H | — | — | — |
| Y.469 | H | H | H | B16 | CF₃ | CF₃ | — | — | — |
| Y.470 | H | Me | H | B16 | Cl | H | — | — | — |
| Y.471 | H | Me | H | B16 | Cl | Cl | — | — | — |
| Y.472 | H | Me | H | B16 | Br | H | — | — | — |
| Y.473 | H | Me | H | B16 | Br | Br | — | — | — |
| Y.474 | H | Me | H | B16 | Me | H | — | — | — |
| Y.475 | H | Me | H | B16 | Me | Me | — | — | — |
| Y.476 | H | Me | H | B16 | CF₃ | H | — | — | — |
| Y.477 | H | Me | H | B16 | CF₃ | CF₃ | — | — | — |
| Y.478 | H | H | H | B17 | Cl | — | — | — | — |
| Y.479 | H | H | H | B17 | Br | — | — | — | — |
| Y.480 | H | H | H | B17 | Me | — | — | — | — |
| Y.481 | H | H | H | B17 | CF₃ | — | — | — | — |
| Y.482 | H | Me | H | B17 | Cl | — | — | — | — |
| Y.483 | H | Me | H | B17 | Br | — | — | — | — |
| Y.484 | H | Me | H | B17 | Me | — | — | — | — |
| Y.485 | H | Me | H | B17 | CF₃ | — | — | — | — |
| Y.486 | H | H | H | B18 | Cl | H | — | — | — |
| Y.487 | H | H | H | B18 | Br | H | — | — | — |
| Y.488 | H | H | H | B18 | Me | H | — | — | — |
| Y.489 | H | H | H | B18 | CF₃ | H | — | — | — |
| Y.490 | H | H | H | B18 | Cl | Me | — | — | — |
| Y.491 | H | H | H | B18 | Br | Me | — | — | — |
| Y.492 | H | H | H | B18 | Me | Me | — | — | — |
| Y.493 | H | H | H | B18 | CF₃ | Me | — | — | — |
| Y.494 | H | Me | H | B18 | Cl | H | — | — | — |
| Y.495 | H | Me | H | B18 | Br | H | — | — | — |
| Y.496 | H | Me | H | B18 | Me | H | — | — | — |
| Y.497 | H | Me | H | B18 | CF₃ | H | — | — | — |

TABLE Y-continued

| Cpd No. | $R_2$ | $R_1$ | $R_3$ | B | $R_{10}$ | $R_{11}$ | $R_{12}$ | $R_{13}$ | $R_{14}$ |
|---|---|---|---|---|---|---|---|---|---|
| Y.498 | H | Me | H | B18 | Cl | Me | — | — | — |
| Y.499 | H | Me | H | B18 | Br | Me | — | — | — |
| Y.500 | H | Me | H | B18 | Me | Me | — | — | — |
| Y.501 | H | Me | H | B18 | $CF_3$ | Me | — | — | — |
| Y.502 | H | H | H | B19 | Cl | H | — | — | — |
| Y.503 | H | H | H | B19 | Br | H | — | — | — |
| Y.504 | H | H | H | B19 | Me | H | — | — | — |
| Y.505 | H | H | H | B19 | $CF_3$ | H | — | — | — |
| Y.506 | H | H | H | B19 | Cl | Me | — | — | — |
| Y.507 | H | H | H | B19 | Br | Me | — | — | — |
| Y.508 | H | H | H | B19 | Me | Me | — | — | — |
| Y.509 | H | H | H | B19 | $CF_3$ | Me | — | — | — |
| Y.510 | H | Me | H | B19 | Cl | H | — | — | — |
| Y.511 | H | Me | H | B19 | Br | H | — | — | — |
| Y.512 | H | Me | H | B19 | Me | H | — | — | — |
| Y.513 | H | Me | H | B19 | $CF_3$ | H | — | — | — |
| Y.514 | H | Me | H | B19 | Cl | Me | — | — | — |
| Y.515 | H | Me | H | B19 | Br | Me | — | — | — |
| Y.516 | H | Me | H | B19 | Me | Me | — | — | — |
| Y.517 | H | Me | H | B19 | $CF_3$ | Me | — | — | — |
| Y.518 | H | H | H | B20 | Cl | H | H | H | H |
| Y.519 | H | H | H | B20 | Cl | H | Cl | H | H |
| Y.520 | H | H | H | B20 | Br | H | H | H | H |
| Y.521 | H | H | H | B20 | Br | H | Br | H | H |
| Y.522 | H | H | H | B20 | Me | H | H | H | H |
| Y.523 | H | H | H | B20 | $CF_3$ | H | H | H | H |
| Y.524 | H | H | H | B20 | COMe | H | H | H | H |
| Y.525 | H | H | H | B20 | Cl | H | H | Cl | H |
| Y.526 | H | Me | H | B20 | Cl | H | H | H | H |
| Y.527 | H | Me | H | B20 | Cl | H | Cl | H | H |
| Y.528 | H | Me | H | B20 | Br | H | H | H | H |
| Y.529 | H | Me | H | B20 | Br | H | Br | H | H |
| Y.530 | H | Me | H | B20 | Me | H | H | H | H |
| Y.531 | H | Me | H | B20 | $CF_3$ | H | H | H | H |
| Y.532 | H | Me | H | B20 | COMe | H | H | H | H |
| Y.533 | H | Me | H | B20 | Cl | H | H | Cl | H |
| Y.534 | H | H | H | B21 | Cl | H | H | H | H |
| Y.535 | H | H | H | B21 | H | Cl | H | H | H |
| Y.536 | H | H | H | B21 | Cl | Cl | H | H | H |
| Y.537 | H | H | H | B21 | H | H | H | Cl | H |
| Y.538 | H | H | H | B21 | Cl | H | H | Cl | H |
| Y.539 | H | H | H | B21 | H | Cl | H | Cl | H |
| Y.540 | H | H | H | B21 | Cl | Cl | H | Cl | H |
| Y.541 | H | H | H | B21 | Br | H | H | H | H |
| Y.542 | H | H | H | B21 | $CF_3$ | H | H | H | H |
| Y.543 | H | H | H | B21 | Me | H | H | H | H |
| Y.544 | H | H | H | B21 | Cl | H | H | H | H |
| Y.545 | H | H | H | B21 | Br | H | H | Cl | H |
| Y.546 | H | H | H | B21 | $CF_3$ | H | H | Cl | H |
| Y.547 | H | H | H | B21 | Me | H | H | Cl | H |
| Y.548 | H | H | H | B21 | Cl | H | H | Cl | H |
| Y.549 | H | Me | H | B21 | Cl | H | H | H | H |
| Y.550 | H | Me | H | B21 | H | Cl | H | H | H |
| Y.551 | H | Me | H | B21 | Cl | Cl | H | H | H |
| Y.552 | H | Me | H | B21 | H | H | H | Cl | H |
| Y.553 | H | Me | H | B21 | Cl | H | H | Cl | H |
| Y.554 | H | Me | H | B21 | H | Cl | H | Cl | H |
| Y.555 | H | Me | H | B21 | Cl | Cl | H | Cl | H |
| Y.556 | H | Me | H | B21 | Br | H | H | H | H |
| Y.557 | H | Me | H | B21 | $CF_3$ | H | H | H | H |
| Y.558 | H | Me | H | B21 | Me | H | H | H | H |
| Y.559 | H | Me | H | B21 | Cl | H | H | H | H |
| Y.560 | H | Me | H | B21 | Br | H | H | Cl | H |
| Y.561 | H | Me | H | B21 | $CF_3$ | H | H | Cl | H |
| Y.562 | H | Me | H | B21 | Me | H | H | Cl | H |
| Y.563 | H | Me | H | B21 | Cl | H | H | Cl | H |
| Y.564 | H | Me | H | B21 | Cl | Cl | H | Br | H |
| Y.565 | H | Me | H | B21 | Br | Br | H | H | H |
| Y.566 | H | Me | H | B21 | Br | Br | H | Br | H |
| Y.567 | H | Me | H | B21 | Me | Me | H | H | H |
| Y.568 | H | Me | H | B21 | Me | Me | H | Cl | H |
| Y.569 | H | Me | H | B21 | Me | Me | H | Br | H |
| Y.570 | H | H | H | B22 | Me | H | H | H | Cl |
| Y.571 | H | H | H | B22 | H | H | H | H | Cl |
| Y.572 | H | H | H | B22 | Me | H | H | H | Cl |
| Y.573 | H | H | H | B22 | H | H | H | Cl | Cl |
| Y.574 | H | H | H | B22 | H | H | H | $NO_2$ | Cl |
| Y.575 | H | H | H | B22 | H | H | H | Me | Cl |

TABLE Y-continued

| Cpd No. | R₂ | R₁ | R₃ | B | R₁₀ | R₁₁ | R₁₂ | R₁₃ | R₁₄ |
|---|---|---|---|---|---|---|---|---|---|
| Y.576 | H | H | H | B22 | H | H | H | H | Br |
| Y.577 | H | H | H | B22 | H | H | H | Cl | Br |
| Y.578 | H | H | H | B22 | H | H | H | Me | Br |
| Y.579 | H | H | H | B22 | H | H | H | Br | Br |
| Y.580 | H | Me | H | B22 | Me | H | H | H | H |
| Y.581 | H | Me | H | B22 | H | H | H | H | Cl |
| Y.582 | H | Me | H | B22 | Me | H | H | H | Cl |
| Y.583 | H | Me | H | B22 | H | H | H | Cl | Cl |
| Y.584 | H | Me | H | B22 | H | H | H | NO₂ | Cl |
| Y.585 | H | Me | H | B22 | H | H | H | Me | Cl |
| Y.586 | H | Me | H | B22 | H | H | H | H | Br |
| Y.587 | H | Me | H | B22 | H | H | H | Cl | Br |
| Y.588 | H | Me | H | B22 | H | H | H | Me | Br |
| Y.589 | H | Me | H | B22 | H | H | H | Br | Br |
| Y.590 | H | H | H | B23 | Cl | H | H | H | H |
| Y.591 | H | H | H | B23 | Cl | Cl | H | H | H |
| Y.592 | H | H | H | B23 | Cl | Me | H | H | H |
| Y.593 | H | H | H | B23 | Me | H | H | H | H |
| Y.594 | H | H | H | B23 | Me | Cl | H | H | H |
| Y.595 | H | H | H | B23 | Me | Me | H | H | H |
| Y.596 | H | H | H | B23 | H | H | H | H | Me |
| Y.597 | H | H | H | B23 | Cl | H | H | H | Me |
| Y.598 | H | H | H | B23 | Me | H | H | H | Me |
| Y.599 | H | Me | H | B23 | Cl | H | H | H | H |
| Y.600 | H | Me | H | B23 | Cl | Cl | H | H | H |
| Y.601 | H | Me | H | B23 | Cl | Me | H | H | H |
| Y.602 | H | Me | H | B23 | Me | H | H | H | H |
| Y.603 | H | Me | H | B23 | Me | Cl | H | H | H |
| Y.604 | H | Me | H | B23 | Me | Me | H | H | H |
| Y.605 | H | Me | H | B23 | H | H | H | H | Me |
| Y.606 | H | Me | H | B23 | Cl | H | H | H | Me |
| Y.607 | H | Me | H | B23 | Me | H | H | H | Me |
| Y.608 | H | H | H | B24 | Cl | H | H | H | H |
| Y.609 | H | H | H | B24 | Br | H | H | H | H |
| Y.610 | H | H | H | B24 | CN | H | H | H | H |
| Y.611 | H | H | H | B24 | Me | H | H | H | H |
| Y.612 | H | H | H | B24 | OMe | H | H | H | H |
| Y.613 | H | H | H | B24 | Cl | H | Cl | H | H |
| Y.614 | H | H | H | B24 | Br | H | Cl | H | H |
| Y.615 | H | H | H | B24 | CN | H | Cl | H | H |
| Y.616 | H | H | H | B24 | Me | H | Cl | H | H |
| Y.617 | H | H | H | B24 | OMe | H | Cl | H | H |
| Y.618 | H | H | H | B24 | Cl | H | F | H | H |
| Y.619 | H | H | H | B24 | Br | H | F | H | H |
| Y.620 | H | H | H | B24 | CN | H | F | H | H |
| Y.621 | H | H | H | B24 | Me | H | F | H | H |
| Y.622 | H | H | H | B24 | OMe | H | F | H | H |
| Y.623 | H | H | H | B24 | Cl | H | H | H | F |
| Y.624 | H | Me | H | B24 | Cl | H | H | H | H |
| Y.625 | H | Me | H | B24 | Br | H | H | H | H |
| Y.626 | H | Me | H | B24 | CN | H | H | H | H |
| Y.627 | H | Me | H | B24 | Me | H | H | H | H |
| Y.628 | H | Me | H | B24 | OMe | H | H | H | H |
| Y.629 | H | Me | H | B24 | Cl | H | Cl | H | H |
| Y.630 | H | Me | H | B24 | Br | H | Cl | H | H |
| Y.631 | H | Me | H | B24 | CN | H | Cl | H | H |
| Y.632 | H | Me | H | B24 | Me | H | Cl | H | H |
| Y.633 | H | Me | H | B24 | OMe | H | Cl | H | H |
| Y.634 | H | Me | H | B24 | Cl | H | F | H | H |
| Y.635 | H | Me | H | B24 | Br | H | F | H | H |
| Y.636 | H | Me | H | B24 | CN | H | F | H | H |
| Y.637 | H | Me | H | B24 | Me | H | F | H | H |
| Y.638 | H | Me | H | B24 | OMe | H | F | H | H |
| Y.639 | H | Me | H | B24 | Cl | H | H | H | F |
| Y.640 | H | Me | H | B25 | Me | H | H | H | H |
| Y.641 | H | Me | H | B25 | Cl | H | H | H | H |
| Y.642 | H | Me | H | B25 | OMe | H | H | H | H |
| Y.643 | H | Me | H | B26 | Me | H | H | H | H |
| Y.644 | H | Me | H | B26 | Cl | H | H | H | H |
| Y.645 | H | Me | H | B26 | OMe | H | H | H | H |
| Y.646 | H | Me | H | B28 | H | H | Me | Me | H |
| Y.647 | H | Me | H | B28 | Me | Me | Me | Me | H |
| Y.648 | H | Me | H | B28 | H | H | Cl | Cl | H |
| Y.649 | H | Me | H | B28 | H | H | Br | Br | H |
| Y.650 | H | Me | H | B28 | H | H | Cl | Br | H |

TABLE Y-continued

| Cpd No. | R₂ | R₁ | R₃ | B | R₁₀ | R₁₁ | R₁₂ | R₁₃ | R₁₄ |
|---|---|---|---|---|---|---|---|---|---|
| Y.651 | H | Me | H | B28 | H | H | Cl | H | H |
| Y.652 | H | Me | H | B29 | H | H | H | Me | Me |
| Y.653 | H | Me | H | B29 | Me | Me | H | Me | Me |

Table 1 provides 653 compounds of formula (IA), wherein A is

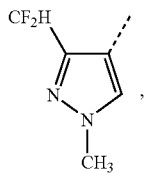

wherein the dashed lines indicate the point of attachment of the group A to the amide group, and $R_1$, $R_2$, $R_3$, B, $R_{10}$, $R_{11}$, $R_{12}$, $R_{13}$ and $R_{14}$ are as defined in Table Y. For example, compound 1.001 has the following structure:

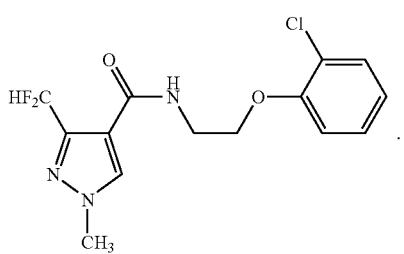

(1.001)

Table 2 provides 653 compounds of formula (IA) wherein A is

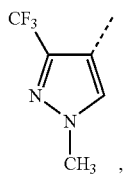

wherein the dashed lines indicate the point of attachment of the group A to the amide group, and $R_1$, $R_2$, $R_3$, B, $R_{10}$, $R_{11}$, $R_{12}$, $R_{13}$ and $R_{14}$ are as defined in Table Y.

Table 3 provides 653 compounds of formula (IA) wherein A is

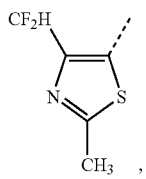

wherein the dashed lines indicate the point of attachment of the group A to the amide group, and $R_1$, $R_2$, $R_3$, B, $R_{10}$, $R_{11}$, $R_{12}$, $R_{13}$ and $R_{14}$ are as defined in Table Y.

Table 4 provides 653 compounds of formula (IA) wherein A is

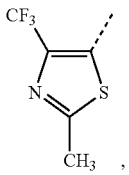

wherein the dashed lines indicate the point of attachment of the group A to the amide group, and $R_1$, $R_2$, $R_3$, B, $R_{10}$, $R_{11}$, $R_{12}$, $R_{13}$ and $R_{14}$ are as defined in Table Y.

Table 5 provides 653 compounds of formula (IA) wherein A is

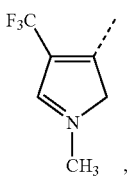

wherein the dashed lines indicate the point of attachment of the group A to the amide group, and $R_1$, $R_2$, $R_3$, B, $R_{10}$, $R_{11}$, $R_{12}$, $R_{13}$ and $R_{14}$ are as defined in Table Y.

Table 6 provides 653 compounds of formula (IA) wherein A is

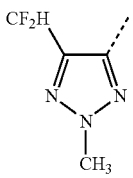

wherein the broken lines indicate the point of attachment of the group A to the amide group, and $R_1$, $R_2$, $R_3$, B, $R_{10}$, $R_{11}$, $R_{12}$, $R_{13}$ and $R_{14}$ are as defined in Table Y.

Table 7 provides 653 compounds of formula (IA) wherein A is

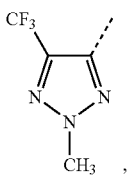

wherein the dashed lines indicate the point of attachment of the group A to the amide group, and $R_1$, $R_2$, $R_3$, B, $R_{10}$, $R_{11}$, $R_{12}$, $R_{13}$ and $R_{14}$ are as defined in Table Y.

Tables 1a to 7a: Compounds of Formula IB
The invention is further illustrated by the preferred individual compounds of formula (IB) listed below in Tables 1a to 7a.
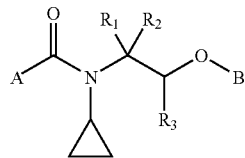
(IB)
wherein
B is one of the preferred groups B1 to B26, B28 or B29:
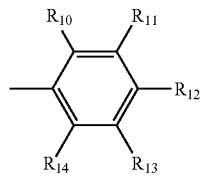
B1
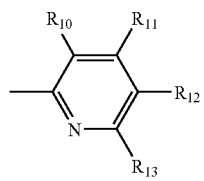
B2
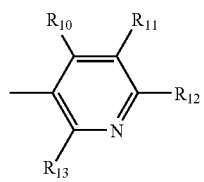
B3
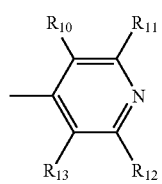
B4
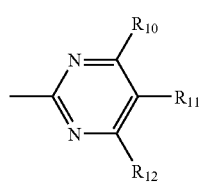
B5
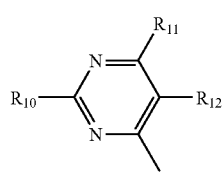
B6
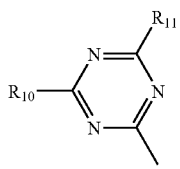
B7
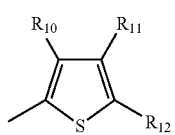
B8
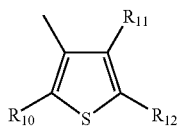
B9
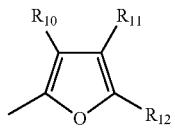
B10
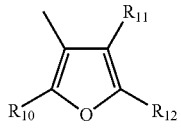
B11
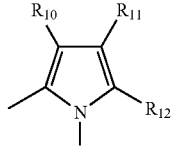
B12
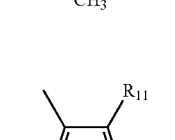
B13
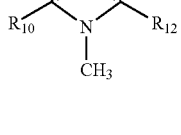
B14
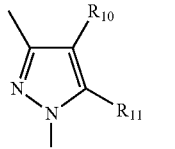
B15

-continued

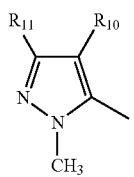
B16

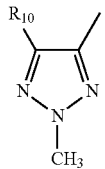
B17

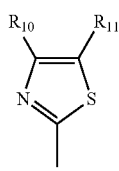
B18

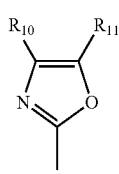
B19

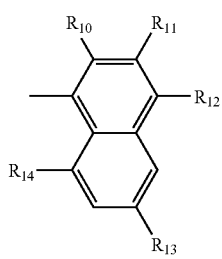
B20

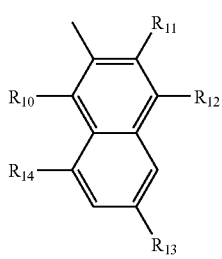
B21

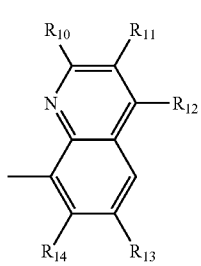
B22

-continued

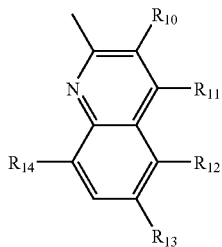
B23

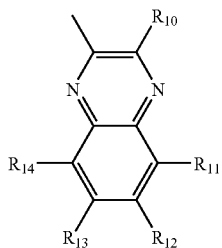
B24

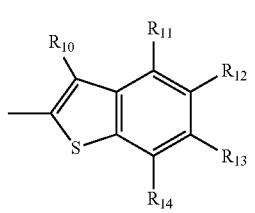
B25

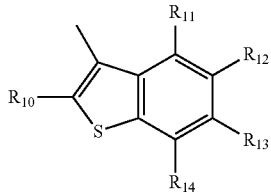
B26

B28

B29

Each of Tables 1a to 7a, which follow the Table Y above, comprises 653 compounds of the formula (IB) in which $R_1$, $R_2$, $R_3$, B, $R_{10}$, $R_{11}$, $R_{12}$, $R_{13}$ and $R_{14}$ and have the values given in Table Y and A has the value given in the relevant Table 1a to 7a. Thus Table 1a corresponds to Table Y when Y is 1a and A has the value given under the Table 1a heading, Table 2a corresponds to Table Y when Y is 2a and A has the value given under the Table 2a heading, and so on for Tables 3a to 7a.

Table 1a provides 653 compounds of formula (IB), wherein A is

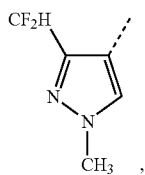

wherein the broken lines indicate the point of attachment of the group A to the amide group, and $R_1$, $R_2$, $R_3$, B, $R_{10}$, $R_{11}$, $R_{12}$, $R_{13}$ and $R_{14}$ are as defined in Table Y. For example, compound 1a.001 has the following structure:

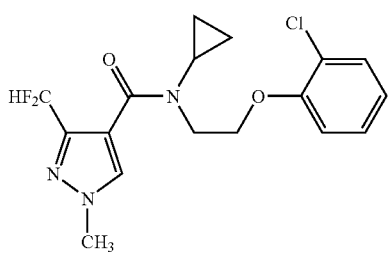

(1a.001)

Table 2a provides 653 compounds of formula (IB) wherein A is

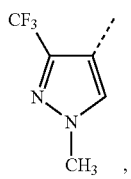

wherein the broken lines indicate the point of attachment of the group A to the amide group, and $R_1$, $R_2$, $R_3$, B, $R_{10}$, $R_{11}$, $R_{12}$, $R_{13}$ and $R_{14}$ are as defined in Table Y.

Table 3a provides 653 compounds of formula (IB) wherein A is

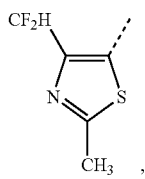

wherein the broken lines indicate the point of attachment of the group A to the amide group, and $R_1$, $R_2$, $R_3$, B, $R_{10}$, $R_{11}$, $R_{12}$, $R_{13}$ and $R_{14}$ are as defined in Table Y.

Table 4a provides 653 compounds of formula (IB) wherein A is

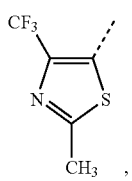

wherein the broken lines indicate the point of attachment of the group A to the amide group, and $R_1$, $R_2$, $R_3$, B, $R_{10}$, $R_{11}$, $R_{12}$, $R_{13}$ and $R_{14}$ are as defined in Table Y.

Table 5a provides 653 compounds of formula (IB) wherein A is

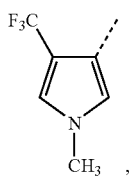

wherein the broken lines indicate the point of attachment of the group A to the amide group, and $R_1$, $R_2$, $R_3$, B, $R_{10}$, $R_{11}$, $R_{12}$, $R_{13}$ and $R_{14}$ are as defined in Table Y.

Table 6a provides 653 compounds of formula (IB) wherein A is

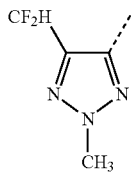

wherein the broken lines indicate the point of attachment of the group A to the amide group, and $R_1$, $R_2$, $R_3$, B, $R_{10}$, $R_{11}$, $R_{12}$, $R_{13}$ and $R_{14}$ are as defined in Table Y.

Table 7a provides 653 compounds of formula (IB) wherein A is

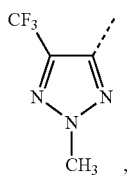

wherein the broken lines indicate the point of attachment of the group A to the amide group, and $R_1$, $R_2$, $R_3$, B, $R_{10}$, $R_{11}$, $R_{12}$, $R_{13}$ and $R_{14}$ are as defined in Table Y.

Table 8: Compounds of Formula IIA
The invention is further illustrated by the preferred individual compounds of formula (IIA)
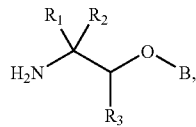
(IIA)
wherein B is one of the preferred groups B1 to B5 or B20 to B26, B28 or B29
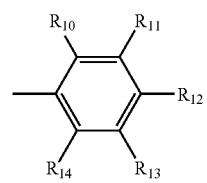
B₁
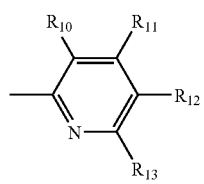
B₂
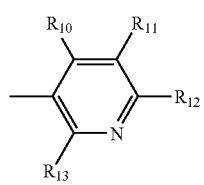
B₃
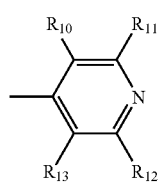
B₄
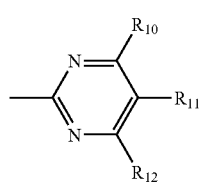
B₅
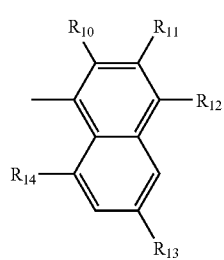
B₂₀
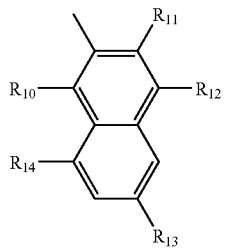
B₂₁
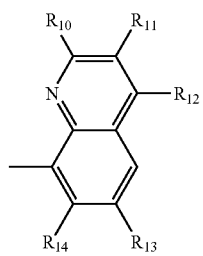
B₂₂
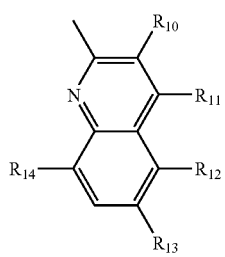
B₂₃
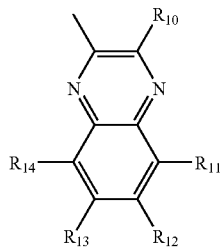
B₂₄
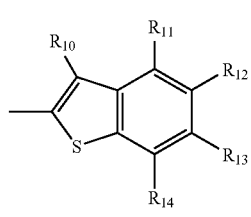
B₂₅
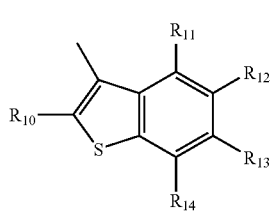
B₂₆

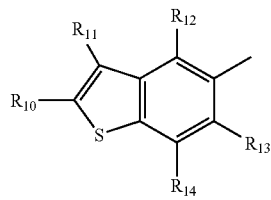

B28

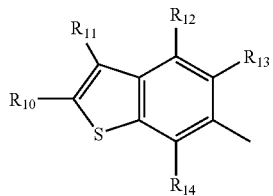

B29

The compound of formula (IIA) are listed below in Table 8. Characterising data is given in Table 12.

TABLE 8

| Cpd No. | $R_2$ | $R_1$ | $R_3$ | B | $R_{10}$ | $R_{11}$ | $R_{12}$ | $R_{13}$ | $R_{14}$ |
|---|---|---|---|---|---|---|---|---|---|
| Z1.001 | H | H | H | B1 | Cl | H | H | H | H |
| Z1.002 | H | H | H | B1 | Cl | Cl | H | H | H |
| Z1.003 | H | H | H | B1 | Cl | H | Cl | H | H |
| Z1.004 | H | H | H | B1 | Cl | H | H | Cl | H |
| Z1.005 | H | H | H | B1 | Cl | H | H | H | Cl |
| Z1.006 | H | H | H | B1 | H | Cl | Cl | H | H |
| Z1.007 | H | H | H | B1 | H | Cl | H | Cl | H |
| Z1.008 | H | H | H | B1 | Cl | H | Cl | H | Cl |
| Z1.009 | H | H | H | B1 | Cl | H | Br | H | Cl |
| Z1.010 | H | H | H | B1 | Cl | H | I | H | Cl |
| Z1.011 | H | H | H | B1 | Cl | H | $CHF_2$ | H | Cl |
| Z1.012 | H | H | H | B1 | Cl | H | $CF_3$ | H | Cl |
| Z1.013 | H | H | H | B1 | Cl | H | C≡C—H | H | Cl |
| Z1.014 | H | H | H | B1 | Cl | H | C≡C—Me | H | Cl |
| Z1.015 | H | H | H | B1 | Cl | H | C≡C—Si(Me)$_3$ | H | Cl |
| Z1.016 | H | H | H | B1 | Cl | H | C≡C-t-Bu | H | Cl |
| Z1.017 | H | H | H | B1 | Cl | H | C≡C-i-Pr | H | Cl |
| Z1.018 | H | H | H | B1 | Cl | H | C≡C—$CH_2$OMe | H | Cl |
| Z1.019 | H | H | H | B1 | Cl | H | C≡C-p-Cl-phenyl | H | Cl |
| Z1.020 | H | H | H | B1 | Cl | H | p-Cl-phenyl | H | Cl |
| Z1.021 | H | H | H | B1 | Cl | H | CHO | H | Cl |
| Z1.022 | H | H | H | B1 | Cl | H | CH=NOMe | H | Cl |
| Z1.023 | H | H | H | B1 | Cl | H | COMe | H | Cl |
| Z1.024 | H | H | H | B1 | Cl | H | C(Me)=NOMe | H | Cl |
| Z1.025 | H | H | H | B1 | Cl | H | $NO_2$ | H | Cl |
| Z1.026 | H | H | H | B1 | Cl | H | $NH_2$ | H | Cl |
| Z1.027 | H | H | H | B1 | Cl | H | NHMe | H | Cl |
| Z1.028 | H | H | H | B1 | Cl | H | N(Me)$_2$ | H | Cl |
| Z1.029 | H | H | H | B1 | Cl | H | NHCOMe | H | Cl |
| Z1.030 | H | H | H | B1 | Cl | H | N=CHNEt(Me) | H | Cl |
| Z1.031 | H | H | H | B1 | Cl | H | $OCF_3$ | H | Cl |
| Z1.032 | H | H | H | B1 | Cl | H | $OCH_2$CH=$CHCl_2$ | H | Cl |
| Z1.033 | H | H | H | B1 | Cl | H | p-Cl-phenoxy | H | Cl |
| Z1.034 | H | H | H | B1 | Cl | Me | Cl | H | Cl |
| Z1.035 | H | H | H | B1 | Cl | Cl | Cl | H | Cl |
| Z1.036 | H | H | H | B1 | Cl | H | Cl | Cl | Cl |
| Z1.037 | H | H | H | B1 | Cl | Cl | Cl | Cl | Cl |
| Z1.038 | H | H | H | B1 | Cl | H | H | H | Me |
| Z1.039 | H | H | H | B1 | Cl | H | Cl | H | Me |
| Z1.040 | H | H | H | B1 | Cl | H | Br | H | Me |
| Z1.041 | H | H | H | B1 | Cl | H | $CF_3$ | H | Me |
| Z1.042 | H | H | H | B1 | Cl | H | C≡C—H | H | Me |
| Z1.043 | H | H | H | B1 | Cl | H | C≡C—$CH_2$OMe | H | Me |
| Z1.044 | H | H | H | B1 | Cl | H | C(Me)=NOMe | H | Me |
| Z1.045 | H | H | H | B1 | Cl | H | H | H | CHO |
| Z1.046 | H | H | H | B1 | Cl | H | Cl | H | CHO |
| Z1.047 | H | H | H | B1 | Cl | H | Br | H | CHO |
| Z1.048 | H | H | H | B1 | Cl | H | $CF_3$ | H | CHO |
| Z1.049 | H | H | H | B1 | Cl | H | C≡C—H | H | CHO |
| Z1.050 | H | H | H | B1 | Cl | H | C≡C—$CH_2$OMe | H | CHO |
| Z1.051 | H | H | H | B1 | Cl | H | C(Me)=NOMe | H | CHO |
| Z1.052 | H | H | H | B1 | Cl | H | H | H | OMe |
| Z1.053 | H | H | H | B1 | Cl | H | Cl | H | OMe |
| Z1.054 | H | H | H | B1 | Cl | H | Br | H | OMe |
| Z1.055 | H | H | H | B1 | Cl | H | $CF_3$ | H | OMe |
| Z1.056 | H | H | H | B1 | Cl | H | C≡C—H | H | OMe |
| Z1.057 | H | H | H | B1 | Cl | H | C≡C—$CH_2$OMe | H | OMe |
| Z1.058 | H | H | H | B1 | Cl | H | C(Me)=NOMe | H | OMe |
| Z1.059 | H | H | H | B1 | OMe | H | H | H | OMe |
| Z1.060 | H | H | H | B1 | OMe | H | Cl | H | OMe |

TABLE 8-continued

| Cpd No. | R$_2$ | R$_1$ | R$_3$ | B | R$_{10}$ | R$_{11}$ | R$_{12}$ | R$_{13}$ | R$_{14}$ |
|---|---|---|---|---|---|---|---|---|---|
| Z1.061 | H | H | H | B1 | OMe | H | Br | H | OMe |
| Z1.062 | H | H | H | B1 | OMe | H | CF$_3$ | H | OMe |
| Z1.063 | H | H | H | B1 | OMe | H | C≡C—H | H | OMe |
| Z1.064 | H | H | H | B1 | OMe | H | C≡C—CH$_2$OMe | H | OMe |
| Z1.065 | H | H | H | B1 | OMe | H | C(Me)=NOMe | H | OMe |
| Z1.066 | H | H | H | B1 | Me | H | H | H | Me |
| Z1.067 | H | H | H | B1 | Me | H | Cl | H | Me |
| Z1.068 | H | H | H | B1 | Me | H | Br | H | Me |
| Z1.069 | H | H | H | B1 | Me | H | I | H | Me |
| Z1.070 | H | H | H | B1 | Me | H | CF$_3$ | H | Me |
| Z1.071 | H | H | H | B1 | Me | H | C≡C—H | H | Me |
| Z1.072 | H | H | H | B1 | Me | H | Me | H | Me |
| Z1.073 | H | H | H | B1 | Me | H | C≡C—CH$_2$OMe | H | Me |
| Z1.074 | H | H | H | B1 | Me | H | C(Me)=NOMe | H | Me |
| Z1.075 | H | H | H | B1 | Me | H | NO$_2$ | H | Me |
| Z1.076 | H | H | H | B1 | Me | H | NH$_2$ | H | Me |
| Z1.077 | H | H | H | B1 | Me | H | NHCOMe | H | Me |
| Z1.078 | H | H | H | B1 | Me | H | p-Cl-phenyl | H | Me |
| Z1.079 | H | H | H | B1 | Me | H | H | H | CHO |
| Z1.080 | H | H | H | B1 | Me | H | Cl | H | CHO |
| Z1.081 | H | H | H | B1 | Me | H | Br | H | CHO |
| Z1.082 | H | H | H | B1 | i-Pr | H | H | H | i-Pr |
| Z1.083 | H | H | H | B1 | i-Pr | H | Cl | H | i-Pr |
| Z1.084 | H | H | H | B1 | i-Pr | H | Br | H | i-Pr |
| Z1.085 | H | H | H | B1 | t-Bu | H | H | H | t-Bu |
| Z1.086 | H | H | H | B1 | t-Bu | H | Cl | H | t-Bu |
| Z1.087 | H | H | H | B1 | t-Bu | H | Br | H | t-Bu |
| Z1.088 | H | H | H | B1 | t-Bu | H | Me | H | t-Bu |
| Z1.089 | H | H | H | B1 | t-Bu | H | t-Bu | H | t-Bu |
| Z1.090 | H | H | H | B1 | t-Bu | H | OMe | H | t-Bu |
| Z1.091 | H | H | H | B1 | Br | H | H | H | Br |
| Z1.092 | H | H | H | B1 | Br | H | Br | H | Br |
| Z1.093 | H | H | H | B1 | F | H | H | H | F |
| Z1.094 | H | H | H | B1 | F | H | Cl | H | F |
| Z1.095 | H | H | H | B1 | F | H | Br | H | F |
| Z1.096 | H | H | H | B1 | I | H | H | H | I |
| Z1.097 | H | H | H | B1 | I | H | Cl | H | I |
| Z1.098 | H | Me | H | B1 | H | H | COMe | H | H |
| Z1.099 | H | Me | H | B1 | H | F | H | F | H |
| Z1.100 | H | Me | H | B1 | Me | H | Cl | H | H |
| Z1.101 | H | Me | H | B1 | H | Cl | Cl | H | H |
| Z1.102 | H | Me | H | B1 | H | t-Bu | H | t-Bu | H |
| Z1.103 | H | Me | H | B1 | Cl | H | Cl | H | H |
| Z1.104 | H | Me | H | B1 | Cl | H | H | Cl | H |
| Z1.105 | H | Me | H | B1 | Cl | H | H | H | Cl |
| Z1.106 | H | Me | H | B1 | H | Cl | Cl | H | H |
| Z1.107 | H | Me | H | B1 | H | Cl | H | Cl | H |
| Z1.108 | H | Me | H | B1 | Cl | H | Cl | H | Cl |
| Z1.109 | H | Me | H | B1 | Cl | H | Br | H | Cl |
| Z1.110 | H | Me | H | B1 | Cl | H | I | H | Cl |
| Z1.111 | H | Me | H | B1 | Cl | H | CHF$_2$ | H | Cl |
| Z1.112 | H | Me | H | B1 | Cl | H | CF$_3$ | H | Cl |
| Z1.113 | H | Me | H | B1 | Cl | H | C≡C—H | H | Cl |
| Z1.114 | H | Me | H | B1 | Cl | H | C≡C—Me | H | Cl |
| Z1.115 | H | Me | H | B1 | Cl | H | C≡C—Si(Me)$_3$ | H | Cl |
| Z1.116 | H | Me | H | B1 | Cl | H | C≡C-t-Bu | H | Cl |
| Z1.117 | H | Me | H | B1 | Cl | H | C≡C—C-i-Pr | H | Cl |
| Z1.118 | H | Me | H | B1 | Cl | H | C≡C—CH$_2$OMe | H | Cl |
| Z1.119 | H | Me | H | B1 | Cl | H | C≡C-p-Cl-phenyl | H | Cl |
| Z1.120 | H | Me | H | B1 | Cl | H | p-Cl-phenyl | H | Cl |
| Z1.121 | H | Me | H | B1 | Cl | H | CHO | H | Cl |
| Z1.122 | H | Me | H | B1 | Cl | H | CH=NOMe | H | Cl |
| Z1.123 | H | Me | H | B1 | Cl | H | COMe | H | Cl |
| Z1.124 | H | Me | H | B1 | Cl | H | C(Me)=NOMe | H | Cl |
| Z1.125 | H | Me | H | B1 | Cl | H | NO$_2$ | H | Cl |
| Z1.126 | H | Me | H | B1 | Cl | H | NH$_2$ | H | Cl |
| Z1.127 | H | Me | H | B1 | Cl | H | NHMe | H | Cl |
| Z1.128 | H | Me | H | B1 | Cl | H | N(Me)$_2$ | H | Cl |
| Z1.129 | H | Me | H | B1 | Cl | H | NHCOMe | H | Cl |
| Z1.130 | H | Me | H | B1 | Cl | H | N=CHNEt(Me) | H | Cl |
| Z1.131 | H | Me | H | B1 | Cl | H | OCF$_3$ | H | Cl |
| Z1.132 | H | Me | H | B1 | Cl | H | OCH$_2$CH=CHCl$_2$ | H | Cl |
| Z1.133 | H | Me | H | B1 | Cl | H | p-Cl-phenoxy | H | Cl |
| Z1.134 | H | Me | H | B1 | Cl | Me | Cl | H | Cl |
| Z1.135 | H | Me | H | B1 | Cl | Cl | Cl | H | Cl |
| Z1.136 | H | Me | H | B1 | Cl | H | Cl | Cl | Cl |
| Z1.137 | H | Me | H | B1 | Cl | Cl | Cl | Cl | Cl |

TABLE 8-continued

| Cpd No. | R$_2$ | R$_1$ | R$_3$ | B | R$_{10}$ | R$_{11}$ | R$_{12}$ | R$_{13}$ | R$_{14}$ |
|---|---|---|---|---|---|---|---|---|---|
| Z1.138 | H | Me | H | B1 | Cl | H | H | H | Me |
| Z1.139 | H | Me | H | B1 | Cl | H | Cl | H | Me |
| Z1.140 | H | Me | H | B1 | Cl | H | Br | H | Me |
| Z1.141 | H | Me | H | B1 | Cl | H | CF$_3$ | H | Me |
| Z1.142 | H | Me | H | B1 | Cl | H | C≡C—H | H | Me |
| Z1.143 | H | Me | H | B1 | Cl | H | C≡C—CH$_2$OMe | H | Me |
| Z1.144 | H | Me | H | B1 | Cl | H | C(Me)=NOMe | H | Me |
| Z1.145 | H | Me | H | B1 | Cl | H | H | H | CHO |
| Z1.146 | H | Me | H | B1 | Cl | H | Cl | H | CHO |
| Z1.147 | H | Me | H | B1 | Cl | H | Br | H | CHO |
| Z1.148 | H | Me | H | B1 | Cl | H | CF$_3$ | H | CHO |
| Z1.149 | H | Me | H | B1 | Cl | H | C≡C—H | H | CHO |
| Z1.150 | H | Me | H | B1 | Cl | H | C≡C—CH$_2$OMe | H | CHO |
| Z1.151 | H | Me | H | B1 | Cl | H | C(Me)=NOMe | H | CHO |
| Z1.152 | H | Me | H | B1 | Cl | H | H | H | OMe |
| Z1.153 | H | Me | H | B1 | Cl | H | Cl | H | OMe |
| Z1.154 | H | Me | H | B1 | Cl | H | Br | H | OMe |
| Z1.155 | H | Me | H | B1 | Cl | H | CF$_3$ | H | OMe |
| Z1.156 | H | Me | H | B1 | Cl | H | C≡C—H | H | OMe |
| Z1.157 | H | Me | H | B1 | Cl | H | C≡C—CH$_2$OMe | H | OMe |
| Z1.158 | H | Me | H | B1 | Cl | H | C(Me)=NOMe | H | OMe |
| Z1.159 | H | Me | H | B1 | OMe | H | H | H | OMe |
| Z1.160 | H | Me | H | B1 | OMe | H | Cl | H | OMe |
| Z1.161 | H | Me | H | B1 | OMe | H | Br | H | OMe |
| Z1.162 | H | Me | H | B1 | OMe | H | CF$_3$ | H | OMe |
| Z1.163 | H | Me | H | B1 | OMe | H | C≡C—H | H | OMe |
| Z1.164 | H | Me | H | B1 | OMe | H | C≡C—CH$_2$OMe | H | OMe |
| Z1.165 | H | Me | H | B1 | OMe | H | C(Me)=NOMe | H | OMe |
| Z1.166 | H | Me | H | B1 | Me | H | H | H | Me |
| Z1.167 | H | Me | H | B1 | Me | H | Cl | H | Me |
| Z1.168 | H | Me | H | B1 | Me | H | Br | H | Me |
| Z1.169 | H | Me | H | B1 | Me | H | I | H | Me |
| Z1.170 | H | Me | H | B1 | Me | H | CF$_3$ | H | Me |
| Z1.171 | H | Me | H | B1 | Me | H | C≡C—H | H | Me |
| Z1.172 | H | Me | H | B1 | Me | H | Me | H | Me |
| Z1.173 | H | Me | H | B1 | Me | H | C≡C—CH$_2$OMe | H | Me |
| Z1.174 | H | Me | H | B1 | Me | H | C(Me)=NOMe | H | Me |
| Z1.175 | H | Me | H | B1 | Me | H | NO$_2$ | H | Me |
| Z1.176 | H | Me | H | B1 | Me | H | NH$_2$ | H | Me |
| Z1.177 | H | Me | H | B1 | Me | H | NHCOMe | H | Me |
| Z1.178 | H | Me | H | B1 | Me | H | p-Cl-phenyl | H | Me |
| Z1.179 | H | Me | H | B1 | Me | H | H | H | CHO |
| Z1.180 | H | Me | H | B1 | Me | H | Cl | H | CHO |
| Z1.181 | H | Me | H | B1 | Me | H | Br | H | CHO |
| Z1.182 | H | Me | H | B1 | i-Pr | H | H | H | i-Pr |
| Z1.183 | H | Me | H | B1 | i-Pr | H | Cl | H | i-Pr |
| Z1.184 | H | Me | H | B1 | i-Pr | H | Br | H | i-Pr |
| Z1.185 | H | Me | H | B1 | t-Bu | H | H | H | t-Bu |
| Z1.186 | H | Me | H | B1 | t-Bu | H | Cl | H | t-Bu |
| Z1.187 | H | Me | H | B1 | t-Bu | H | Me | H | t-Bu |
| Z1.188 | H | Me | H | B1 | t-Bu | H | t-Bu | H | t-Bu |
| Z1.189 | H | Me | H | B1 | t-Bu | H | p-Cl-phenyl | H | t-Bu |
| Z1.190 | H | Me | H | B1 | H | H | CF$_3$ | H | H |
| Z1.191 | H | Me | H | B1 | H | H | Br | H | H |
| Z1.192 | H | Me | H | B1 | Br | H | H | H | Br |
| Z1.193 | H | Me | H | B1 | Br | H | Br | H | Br |
| Z1.194 | H | Me | H | B1 | F | H | H | H | F |
| Z1.195 | H | Me | H | B1 | F | H | Cl | H | F |
| Z1.196 | H | Me | H | B1 | F | H | Br | H | F |
| Z1.197 | H | Me | H | B1 | I | H | H | H | I |
| Z1.198 | H | Me | H | B1 | I | H | Cl | H | I |
| Z1.199 | H | Me | H | B1 | I | H | Br | H | I |
| Z1.200 | H | Me | H | B1 | I | H | I | H | I |
| Z1.201 | H | Me | Me | B1 | Cl | H | H | H | Cl |
| Z1.202 | H | Me | Me | B1 | Cl | H | Cl | H | Cl |
| Z1.203 | H | Me | Me | B1 | Br | H | H | H | Br |
| Z1.204 | H | Me | Me | B1 | Br | H | Br | H | Br |
| Z1.205 | H | Me | Me | B1 | Me | H | H | H | Me |
| Z1.206 | H | Me | Me | B1 | Me | H | Cl | H | Me |
| Z1.207 | H | Me | Me | B1 | Me | H | Br | H | Me |
| Z1.208 | H | Me | H | B1 | Cl | H | H | H | Cl |
| Z1.209 | Me | Me | H | B1 | Cl | H | Cl | H | Cl |
| Z1.210 | Me | Me | H | B1 | Br | H | H | H | Br |
| Z1.211 | Me | Me | H | B1 | Br | H | Br | H | Br |
| Z1.212 | Me | Me | H | B1 | Me | H | Cl | H | Me |
| Z1.213 | Me | Me | H | B1 | Me | H | Br | H | Me |
| Z1.214 | i-Pr | Me | H | B1 | Me | H | H | H | Me |

TABLE 8-continued

| Cpd No. | $R_2$ | $R_1$ | $R_3$ | B | $R_{10}$ | $R_{11}$ | $R_{12}$ | $R_{13}$ | $R_{14}$ |
|---|---|---|---|---|---|---|---|---|---|
| Z1.215 | c-Pr | Me | H | B1 | Me | H | H | H | Me |
| Z1.216 | Et | Et | H | B1 | Me | H | H | H | Me |
| Z1.217 | Et | Et | H | B1 | Me | H | Br | H | Me |
| Z1.218 | CH$_2$CH$_2$ | | H | B1 | Cl | H | H | H | H |
| Z1.219 | CH$_2$CH$_2$ | | H | B1 | Me | H | H | H | Me |
| Z1.220 | CH$_2$CH$_2$ | | H | B1 | Me | H | Br | H | Me |
| Z1.221 | CH$_2$CH$_2$ | | H | B1 | H | H | Cl | H | H |
| Z1.222 | CH$_2$CH$_2$ | | H | B1 | Cl | H | Cl | H | H |
| Z1.223 | CH$_2$CH$_2$ | | H | B1 | Cl | H | H | H | Cl |
| Z1.224 | CH$_2$CH$_2$ | | H | B1 | Cl | H | Cl | H | Cl |
| Z1.225 | CH$_2$CH$_2$ | | H | B1 | Br | H | H | H | Br |
| Z1.226 | CH$_2$CH$_2$ | | H | B1 | Br | H | Br | H | Br |
| Z1.227 | H | CH$_2$ | | B1 | Me | H | H | H | Me |
| Z1.228 | H | CH$_2$ | | B1 | Me | H | Br | H | Me |
| Z1.229 | H | CH$_2$ | | B1 | H | H | Cl | H | H |
| Z1.230 | H | CH$_2$ | | B1 | Cl | H | Cl | H | H |
| Z1.231 | H | CH$_2$ | | B1 | Cl | H | H | H | Cl |
| Z1.232 | H | CH$_2$ | | B1 | Cl | H | Cl | H | Cl |
| Z1.233 | H | CH$_2$ | | B1 | Br | H | H | H | Br |
| Z1.234 | H | CH$_2$ | | B1 | Br | H | Br | H | Br |
| Z1.235 | H | H | H | B2 | Cl | H | Cl | H | — |
| Z1.236 | H | H | H | B2 | Cl | H | Br | H | — |
| Z1.237 | H | H | H | B2 | Br | H | Br | H | — |
| Z1.238 | H | H | H | B2 | Cl | H | CF$_3$ | H | — |
| Z1.239 | H | Me | H | B2 | Cl | H | CF$_3$ | H | — |
| Z1.240 | H | Et | H | B2 | Cl | H | CF$_3$ | H | — |
| Z1.241 | Me | Me | H | B2 | Cl | H | CF$_3$ | H | — |
| Z1.242 | H | H | Me | B2 | Cl | H | CF$_3$ | H | — |
| Z1.243 | H | Et | H | B2 | Cl | H | CF$_3$ | H | — |
| Z1.244 | CH$_2$CH$_2$ | | H | B2 | Cl | H | CF$_3$ | H | — |
| Z1.245 | H | CH$_2$ | | B2 | Cl | H | CF$_3$ | H | — |
| Z1.246 | H | H | H | B3 | Cl | H | H | Cl | — |
| Z1.247 | H | H | H | B3 | Cl | H | H | Br | — |
| Z1.248 | H | H | H | B3 | Cl | H | H | I | — |
| Z1.249 | H | H | H | B3 | Cl | H | H | Me | — |
| Z1.250 | H | H | H | B3 | Me | H | H | Cl | — |
| Z1.251 | H | H | H | B3 | Me | H | H | Br | — |
| Z1.252 | H | H | H | B3 | Me | H | H | Me | — |
| Z1.253 | H | Me | H | B3 | Cl | H | H | Cl | — |
| Z1.254 | H | Me | H | B3 | Me | H | H | Cl | — |
| Z1.255 | H | H | H | B4 | Cl | H | H | Cl | — |
| Z1.256 | H | H | H | B4 | Br | H | H | Br | — |
| Z1.247 | H | H | H | B4 | Me | H | H | Me | — |
| Z1.258 | H | Me | H | B4 | Cl | H | H | Cl | — |
| Z1.259 | H | Me | H | B4 | Br | H | H | Br | — |
| Z1.260 | H | Me | H | B4 | Me | H | H | Me | — |
| Z1.261 | H | H | H | B5 | Me | H | Me | — | — |
| Z1.262 | H | H | H | B5 | Me | H | Me | — | — |
| Z1.263 | H | H | H | B5 | H | Me | H | — | — |
| Z1.264 | H | H | H | B5 | H | Cl | H | — | — |
| Z1.265 | H | H | H | B5 | H | Br | H | — | — |
| Z1.266 | H | H | H | B5 | H | CF$_3$ | H | — | — |
| Z1.267 | H | Me | H | B5 | Me | H | Me | — | — |
| Z1.268 | H | Me | H | B5 | Me | H | Me | — | — |
| Z1.269 | H | Me | H | B5 | H | Me | H | — | — |
| Z1.270 | H | Me | H | B5 | H | Cl | H | — | — |
| Z1.271 | H | Me | H | B5 | H | Br | H | — | — |
| Z1.272 | H | Me | H | B5 | H | CF$_3$ | H | — | — |
| Z1.273 | H | H | H | B20 | Cl | H | H | H | H |
| Z1.274 | H | H | H | B20 | Cl | H | Cl | H | H |
| Z1.275 | H | H | H | B20 | Br | H | H | H | H |
| Z1.276 | H | H | H | B20 | Br | H | Br | H | H |
| Z1.277 | H | H | H | B20 | Me | H | H | H | H |
| Z1.278 | H | H | H | B20 | CF$_3$ | H | H | H | H |
| Z1.279 | H | H | H | B20 | COMe | H | H | H | H |
| Z1.280 | H | H | H | B20 | Cl | H | H | Cl | H |
| Z1.281 | H | Me | H | B20 | Cl | H | H | H | H |
| Z1.282 | H | Me | H | B20 | Cl | H | Cl | H | H |
| Z1.283 | H | Me | H | B20 | Br | H | H | H | H |
| Z1.284 | H | Me | H | B20 | Br | H | Br | H | H |
| Z1.285 | H | Me | H | B20 | Me | H | H | H | H |
| Z1.286 | H | Me | H | B20 | CF$_3$ | H | H | H | H |
| Z1.287 | H | Me | H | B20 | COMe | H | H | H | H |
| Z1.288 | H | Me | H | B20 | Cl | H | H | Cl | H |
| Z1.289 | H | H | H | B21 | Cl | H | H | H | H |
| Z1.290 | H | H | H | B21 | H | Cl | H | H | H |
| Z1.291 | H | H | H | B21 | Cl | Cl | H | H | H |

TABLE 8-continued

| Cpd No. | R₂ | R₁ | R₃ | B | R₁₀ | R₁₁ | R₁₂ | R₁₃ | R₁₄ |
|---|---|---|---|---|---|---|---|---|---|
| Z1.292 | H | H | H | B21 | H | H | H | Cl | H |
| Z1.293 | H | H | H | B21 | Cl | H | H | Cl | H |
| Z1.294 | H | H | H | B21 | H | Cl | H | Cl | H |
| Z1.295 | H | H | H | B21 | Cl | Cl | H | Cl | H |
| Z1.296 | H | H | H | B21 | Br | H | H | H | H |
| Z1.297 | H | H | H | B21 | CF₃ | H | H | H | H |
| Z1.298 | H | H | H | B21 | Me | H | H | H | H |
| Z1.299 | H | H | H | B21 | Cl | H | H | H | H |
| Z1.300 | H | H | H | B21 | Br | H | H | Cl | H |
| Z1.301 | H | H | H | B21 | CF₃ | H | H | Cl | H |
| Z1.302 | H | H | H | B21 | Me | H | H | Cl | H |
| Z1.303 | H | H | H | B21 | Cl | H | H | Cl | H |
| Z1.304 | H | Me | H | B21 | Cl | H | H | H | H |
| Z1.305 | H | Me | H | B21 | H | Cl | H | H | H |
| Z1.306 | H | Me | H | B21 | Cl | Cl | H | H | H |
| Z1.307 | H | Me | H | B21 | H | H | H | Cl | H |
| Z1.308 | H | Me | H | B21 | Cl | H | H | Cl | H |
| Z1.309 | H | Me | H | B21 | H | Cl | H | Cl | H |
| Z1.310 | H | Me | H | B21 | Cl | Cl | H | Cl | H |
| Z1.311 | H | Me | H | B21 | Br | H | H | H | H |
| Z1.312 | H | Me | H | B21 | CF₃ | H | H | H | H |
| Z1.313 | H | Me | H | B21 | Me | H | H | H | H |
| Z1.314 | H | Me | H | B21 | Cl | H | H | H | H |
| Z1.315 | H | Me | H | B21 | Br | H | H | Cl | H |
| Z1.316 | H | Me | H | B21 | CF₃ | H | H | Cl | H |
| Z1.317 | H | Me | H | B21 | Me | H | H | Cl | H |
| Z1.318 | H | Me | H | B21 | Cl | H | H | Cl | H |
| Z1.319 | H | H | H | B22 | Me | H | H | H | H |
| Z1.320 | H | H | H | B22 | H | H | H | H | Cl |
| Z1.321 | H | H | H | B22 | Me | H | H | H | Cl |
| Z1.322 | H | H | H | B22 | H | H | H | Cl | Cl |
| Z1.323 | H | H | H | B22 | H | H | H | NO₂ | Cl |
| Z1.324 | H | H | H | B22 | H | H | H | Me | Cl |
| Z1.325 | H | H | H | B22 | H | H | H | H | Br |
| Z1.326 | H | H | H | B22 | H | H | H | Cl | Br |
| Z1.327 | H | H | H | B22 | H | H | H | Me | Br |
| Z1.328 | H | H | H | B22 | H | H | H | Br | Br |
| Z1.329 | H | Me | H | B22 | Me | H | H | H | H |
| Z1.330 | H | Me | H | B22 | H | H | H | H | Cl |
| Z1.331 | H | Me | H | B22 | Me | H | H | H | Cl |
| Z1.332 | H | Me | H | B22 | H | H | H | Cl | Cl |
| Z1.333 | H | Me | H | B22 | H | H | H | NO₂ | Cl |
| Z1.334 | H | Me | H | B22 | H | H | H | Me | Cl |
| Z1.335 | H | Me | H | B22 | H | H | H | H | Br |
| Z1.336 | H | Me | H | B22 | H | H | H | Cl | Br |
| Z1.337 | H | Me | H | B22 | H | H | H | Me | Br |
| Z1.338 | H | Me | H | B22 | H | H | H | Br | Br |
| Z1.339 | H | H | H | B23 | Cl | H | H | H | H |
| Z1.340 | H | H | H | B23 | Cl | Cl | H | H | H |
| Z1.341 | H | H | H | B23 | Cl | Me | H | H | H |
| Z1.342 | H | H | H | B23 | Me | H | H | H | H |
| Z1.343 | H | H | H | B23 | Me | Cl | H | H | H |
| Z1.344 | H | H | H | B23 | Me | Me | H | H | H |
| Z1.345 | H | H | H | B23 | H | H | H | H | Me |
| Z1.346 | H | H | H | B23 | Cl | H | H | H | Me |
| Z1.347 | H | H | H | B23 | Me | H | H | H | Me |
| Z1.348 | H | Me | H | B23 | Cl | H | H | H | H |
| Z1.349 | H | Me | H | B23 | Cl | Cl | H | H | H |
| Z1.350 | H | Me | H | B23 | Cl | Me | H | H | H |
| Z1.351 | H | Me | H | B23 | Me | H | H | H | H |
| Z1.352 | H | Me | H | B23 | Me | Cl | H | H | H |
| Z1.353 | H | Me | H | B23 | Me | Me | H | H | H |
| Z1.354 | H | Me | H | B23 | H | H | H | H | Me |
| Z1.355 | H | Me | H | B23 | Cl | H | H | H | Me |
| Z1.356 | H | Me | H | B23 | Me | H | H | H | Me |
| Z1.357 | H | H | H | B24 | Cl | H | H | H | H |
| Z1.358 | H | H | H | B24 | Br | H | H | H | H |
| Z1.359 | H | H | H | B24 | CN | H | H | H | H |
| Z1.360 | H | H | H | B24 | Me | H | H | H | H |
| Z1.361 | H | H | H | B24 | OMe | H | H | H | H |
| Z1.362 | H | H | H | B24 | Cl | H | Cl | H | H |
| Z1.363 | H | H | H | B24 | Br | H | Cl | H | H |
| Z1.364 | H | H | H | B24 | CN | H | Cl | H | H |
| Z1.365 | H | H | H | B24 | Me | H | Cl | H | H |
| Z1.366 | H | H | H | B24 | OMe | H | Cl | H | H |
| Z1.367 | H | H | H | B24 | Cl | H | F | H | H |
| Z1.368 | H | H | H | B24 | Br | H | F | H | H |

TABLE 8-continued

| Cpd No. | $R_2$ | $R_1$ | $R_3$ | B | $R_{10}$ | $R_{11}$ | $R_{12}$ | $R_{13}$ | $R_{14}$ |
|---|---|---|---|---|---|---|---|---|---|
| Z1.369 | H | H | H | B24 | CN | H | F | H | H |
| Z1.370 | H | H | H | B24 | Me | H | F | H | H |
| Z1.371 | H | H | H | B24 | OMe | H | F | H | H |
| Z1.372 | H | H | H | B24 | Cl | H | H | H | F |
| Z1.373 | H | Me | H | B24 | Cl | H | H | H | H |
| Z1.374 | H | Me | H | B24 | Br | H | H | H | H |
| Z1.375 | H | Me | H | B24 | CN | H | H | H | H |
| Z1.376 | H | Me | H | B24 | Me | H | H | H | H |
| Z1.377 | H | Me | H | B24 | OMe | H | H | H | H |
| Z1.378 | H | Me | H | B24 | Cl | H | Cl | H | H |
| Z1.379 | H | Me | H | B24 | Br | H | Cl | H | H |
| Z1.380 | H | Me | H | B24 | CN | H | Cl | H | H |
| Z1.381 | H | Me | H | B24 | Me | H | Cl | H | H |
| Z1.382 | H | Me | H | B24 | OMe | H | Cl | H | H |
| Z1.383 | H | Me | H | B24 | Cl | H | F | H | H |
| Z1.384 | H | Me | H | B24 | Br | H | F | H | H |
| Z1.385 | H | Me | H | B24 | CN | H | F | H | H |
| Z1.386 | H | Me | H | B24 | Me | H | F | H | H |
| Z1.387 | H | Me | H | B24 | OMe | H | F | H | H |
| Z1.388 | H | Me | H | B24 | Cl | H | H | H | F |
| Z1.389 | H | Me | H | B25 | Me | H | H | H | H |
| Z1.390 | H | Me | H | B25 | Cl | H | H | H | H |
| Z1.391 | H | Me | H | B25 | OMe | H | H | H | H |
| Z1.392 | H | Me | H | B26 | Me | H | H | H | H |
| Z1.393 | H | Me | H | B26 | Cl | H | H | H | H |
| Z1.394 | H | Me | H | B26 | OMe | H | H | H | H |
| Z1.395 | H | Me | H | B28 | H | H | Me | Me | H |
| Z1.396 | H | Me | H | B28 | Me | Me | Me | Me | H |
| Z1.397 | H | Me | H | B29 | H | H | H | Me | Me |
| Z1.398 | H | Me | H | B29 | Me | Me | H | Me | Me |

Table 8a: Compounds of Formula IIB

The invention is further illustrated by the preferred individual compounds of formula (IIB)

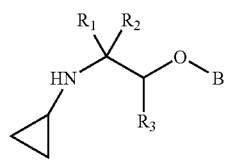

(IIB)

wherein B is one of the preferred groups B1 to B5 or B20 to B26, B28 or B29

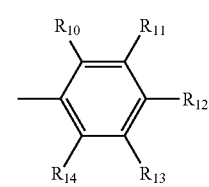

B1

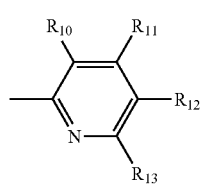

B2

-continued

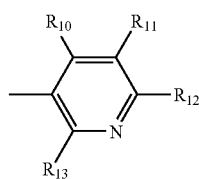

B3

B4

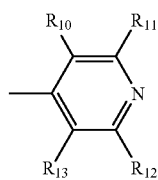

B5

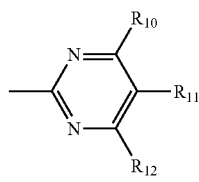

B20

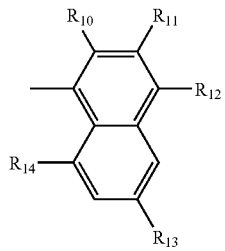

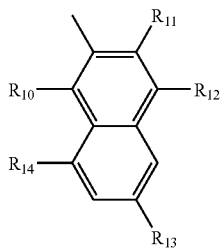
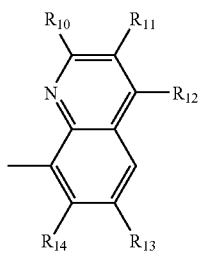
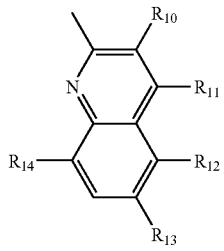
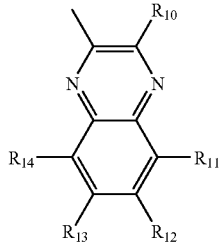

B21 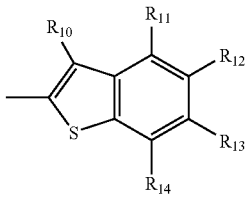

B22 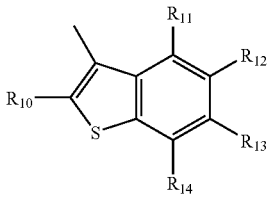

B23 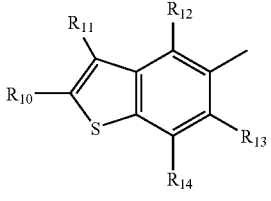

B24 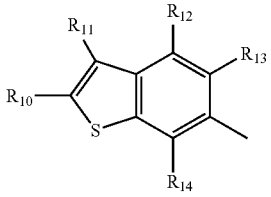

B25

B26

B28

B29

The compound of formula (IIB) are listed below in Table 8a.

TABLE 8a

| Cpd No. | $R_2$ | $R_1$ | $R_3$ | B | $R_{10}$ | $R_{11}$ | $R_{12}$ | $R_{13}$ | $R_{14}$ |
|---|---|---|---|---|---|---|---|---|---|
| Z1a.001 | H | H | H | B1 | Cl | H | H | H | H |
| Z1a.002 | H | H | H | B1 | Cl | Cl | H | H | H |
| Z1a.003 | H | H | H | B1 | Cl | H | Cl | H | H |
| Z1a.004 | H | H | H | B1 | Cl | H | H | Cl | H |
| Z1a.005 | H | H | H | B1 | Cl | H | H | H | Cl |
| Z1a.006 | H | H | H | B1 | H | Cl | Cl | H | H |
| Z1a.007 | H | H | H | B1 | H | Cl | H | Cl | H |
| Z1a.008 | H | H | H | B1 | Cl | H | Cl | H | Cl |
| Z1a.009 | H | H | H | B1 | Cl | H | Br | H | Cl |
| Z1a.010 | H | H | H | B1 | Cl | H | I | H | Cl |
| Z1a.011 | H | H | H | B1 | Cl | H | $CHF_2$ | H | Cl |
| Z1a.012 | H | H | H | B1 | Cl | H | $CF_3$ | H | Cl |
| Z1a.013 | H | H | H | B1 | Cl | H | C≡C—H | H | Cl |
| Z1a.014 | H | H | H | B1 | Cl | H | C≡C-Me | H | Cl |
| Z1a.015 | H | H | H | B1 | Cl | H | C≡C—Si(Me)$_3$ | H | Cl |
| Z1a.016 | H | H | H | B1 | Cl | H | C≡C-t-Bu | H | Cl |
| Z1a.017 | H | H | H | B1 | Cl | H | C≡C-i-Pr | H | Cl |
| Z1a.018 | H | H | H | B1 | Cl | H | C≡C—$CH_2$OMe | H | Cl |
| Z1a.019 | H | H | H | B1 | Cl | H | C≡C-p-Cl-phenyl | H | Cl |
| Z1a.020 | H | H | H | B1 | Cl | H | p-Cl-phenyl | H | Cl |
| Z1a.021 | H | H | H | B1 | Cl | H | CHO | H | Cl |
| Z1a.022 | H | H | H | B1 | Cl | H | CH=NOMe | H | Cl |
| Z1a.023 | H | H | H | B1 | Cl | H | COMe | H | Cl |
| Z1a.024 | H | H | H | B1 | Cl | H | C(Me)=NOMe | H | Cl |

TABLE 8a-continued

| Cpd No. | $R_2$ | $R_1$ | $R_3$ | B | $R_{10}$ | $R_{11}$ | $R_{12}$ | $R_{13}$ | $R_{14}$ |
|---|---|---|---|---|---|---|---|---|---|
| Z1a.025 | H | H | H | B1 | Cl | H | $NO_2$ | H | Cl |
| Z1a.026 | H | H | H | B1 | Cl | H | $NH_2$ | H | Cl |
| Z1a.027 | H | H | H | B1 | Cl | H | NHMe | H | Cl |
| Z1a.028 | H | H | H | B1 | Cl | H | $N(Me)_2$ | H | Cl |
| Z1a.029 | H | H | H | B1 | Cl | H | NHCOMe | H | Cl |
| Z1a.030 | H | H | H | B1 | Cl | H | N=CHNEt(Me) | H | Cl |
| Z1a.031 | H | H | H | B1 | Cl | H | $OCF_3$ | H | Cl |
| Z1a.032 | H | H | H | B1 | Cl | H | $OCH_2CH=CHCl_2$ | H | Cl |
| Z1a.033 | H | H | H | B1 | Cl | H | p-Cl-phenoxy | H | Cl |
| Z1a.034 | H | H | H | B1 | Cl | Me | Cl | H | Cl |
| Z1a.035 | H | H | H | B1 | Cl | Cl | Cl | H | Cl |
| Z1a.036 | H | H | H | B1 | Cl | H | Cl | Cl | Cl |
| Z1a.037 | H | H | H | B1 | Cl | Cl | Cl | Cl | Cl |
| Z1a.038 | H | H | H | B1 | Cl | H | H | H | Me |
| Z1a.039 | H | H | H | B1 | Cl | H | Cl | H | Me |
| Z1a.040 | H | H | H | B1 | Cl | H | Br | H | Me |
| Z1a.041 | H | H | H | B1 | Cl | H | $CF_3$ | H | Me |
| Z1a.042 | H | H | H | B1 | Cl | H | C≡C—H | H | Me |
| Z1a.043 | H | H | H | B1 | Cl | H | C≡C—$CH_2$OMe | H | Me |
| Z1a.044 | H | H | H | B1 | Cl | H | C(Me)=NOMe | H | Me |
| Z1a.045 | H | H | H | B1 | Cl | H | H | H | CHO |
| Z1a.046 | H | H | H | B1 | Cl | H | Cl | H | CHO |
| Z1a.047 | H | H | H | B1 | Cl | H | Br | H | CHO |
| Z1a.048 | H | H | H | B1 | Cl | H | $CF_3$ | H | CHO |
| Z1a.049 | H | H | H | B1 | Cl | H | C≡C—H | H | CHO |
| Z1a.050 | H | H | H | B1 | Cl | H | C≡C—$CH_2$OMe | H | CHO |
| Z1a.051 | H | H | H | B1 | Cl | H | C(Me)=NOMe | H | CHO |
| Z1a.052 | H | H | H | B1 | Cl | H | H | H | OMe |
| Z1a.053 | H | H | H | B1 | Cl | H | Cl | H | OMe |
| Z1a.054 | H | H | H | B1 | Cl | H | Br | H | OMe |
| Z1a.055 | H | H | H | B1 | Cl | H | $CF_3$ | H | OMe |
| Z1a.056 | H | H | H | B1 | Cl | H | C≡C—H | H | OMe |
| Z1a.057 | H | H | H | B1 | Cl | H | C≡C—$CH_2$OMe | H | OMe |
| Z1a.058 | H | H | H | B1 | Cl | H | C(Me)=NOMe | H | OMe |
| Z1a.059 | H | H | H | B1 | OMe | H | H | H | OMe |
| Z1a.060 | H | H | H | B1 | OMe | H | Cl | H | OMe |
| Z1a.061 | H | H | H | B1 | OMe | H | Br | H | OMe |
| Z1a.062 | H | H | H | B1 | OMe | H | $CF_3$ | H | OMe |
| Z1a.063 | H | H | H | B1 | OMe | H | C≡C—H | H | OMe |
| Z1a.064 | H | H | H | B1 | OMe | H | C≡C—$CH_2$OMe | H | OMe |
| Z1a.065 | H | H | H | B1 | OMe | H | C(Me)=NOMe | H | OMe |
| Z1a.066 | H | H | H | B1 | Me | H | H | H | Me |
| Z1a.067 | H | H | H | B1 | Me | H | Cl | H | Me |
| Z1a.068 | H | H | H | B1 | Me | H | Br | H | Me |
| Z1a.069 | H | H | H | B1 | Me | H | I | H | Me |
| Z1a.070 | H | H | H | B1 | Me | H | $CF_3$ | H | Me |
| Z1a.071 | H | H | H | B1 | Me | H | C≡C—H | H | Me |
| Z1a.072 | H | H | H | B1 | Me | H | Me | H | Me |
| Z1a.073 | H | H | H | B1 | Me | H | C≡C—$CH_2$OMe | H | Me |
| Z1a.074 | H | H | H | B1 | Me | H | C(Me)=NOMe | H | Me |
| Z1a.075 | H | H | H | B1 | Me | H | $NO_2$ | H | Me |
| Z1a.076 | H | H | H | B1 | Me | H | $NH_2$ | H | Me |
| Z1a.077 | H | H | H | B1 | Me | H | NHCOMe | H | Me |
| Z1a.078 | H | H | H | B1 | Me | H | p-Cl-phenyl | H | Me |
| Z1a.079 | H | H | H | B1 | Me | H | H | H | CHO |
| Z1a.080 | H | H | H | B1 | Me | H | Cl | H | CHO |
| Z1a.081 | H | H | H | B1 | Me | H | Br | H | CHO |
| Z1a.082 | H | H | H | B1 | i-Pr | H | H | H | i-Pr |
| Z1a.083 | H | H | H | B1 | i-Pr | H | Cl | H | i-Pr |
| Z1a.084 | H | H | H | B1 | i-Pr | H | Br | H | i-Pr |
| Z1a.085 | H | H | H | B1 | t-Bu | H | H | H | t-Bu |
| Z1a.086 | H | H | H | B1 | t-Bu | H | Cl | H | t-Bu |
| Z1a.087 | H | H | H | B1 | t-Bu | H | Br | H | t-Bu |
| Z1a.088 | H | H | H | B1 | t-Bu | H | Me | H | t-Bu |
| Z1a.089 | H | H | H | B1 | t-Bu | H | t-Bu | H | t-Bu |
| Z1a.090 | H | H | H | B1 | t-Bu | H | OMe | H | t-Bu |
| Z1a.091 | H | H | H | B1 | Br | H | H | H | Br |
| Z1a.092 | H | H | H | B1 | Br | H | Br | H | Br |
| Z1a.093 | H | H | H | B1 | F | H | H | H | F |
| Z1a.094 | H | H | H | B1 | F | H | Cl | H | F |
| Z1a.095 | H | H | H | B1 | F | H | Br | H | F |
| Z1a.096 | H | H | H | B1 | I | H | H | H | I |
| Z1a.097 | H | H | H | B1 | I | H | Cl | H | I |
| Z1a.098 | H | Me | H | B1 | H | H | COMe | H | H |
| Z1a.099 | H | Me | H | B1 | H | F | H | F | H |
| Z1a.100 | H | Me | H | B1 | Me | H | Cl | H | H |
| Z1a.101 | H | Me | H | B1 | H | Cl | Cl | H | H |
| Z1a.102 | H | Me | H | B1 | H | t-Bu | H | t-Bu | H |

TABLE 8a-continued

| Cpd No. | R$_2$ | R$_1$ | R$_3$ | B | R$_{10}$ | R$_{11}$ | R$_{12}$ | R$_{13}$ | R$_{14}$ |
|---|---|---|---|---|---|---|---|---|---|
| Z1a.103 | H | Me | H | B1 | Cl | H | Cl | H | H |
| Z1a.104 | H | Me | H | B1 | Cl | H | H | Cl | H |
| Z1a.105 | H | Me | H | B1 | Cl | H | H | H | Cl |
| Z1a.106 | H | Me | H | B1 | H | Cl | Cl | H | H |
| Z1a.107 | H | Me | H | B1 | H | Cl | H | Cl | H |
| Z1a.108 | H | Me | H | B1 | Cl | H | Cl | H | Cl |
| Z1a.109 | H | Me | H | B1 | Cl | H | Br | H | Cl |
| Z1a.110 | H | Me | H | B1 | Cl | H | I | H | Cl |
| Z1a.111 | H | Me | H | B1 | Cl | H | CHF$_2$ | H | Cl |
| Z1a.112 | H | Me | H | B1 | Cl | H | CF$_3$ | H | Cl |
| Z1a.113 | H | Me | H | B1 | Cl | H | C≡C—H | H | Cl |
| Z1a.114 | H | Me | H | B1 | Cl | H | C≡C-Me | H | Cl |
| Z1a.115 | H | Me | H | B1 | Cl | H | C≡C—Si(Me)$_3$ | H | Cl |
| Z1a.116 | H | Me | H | B1 | Cl | H | C≡C-t-Bu | H | Cl |
| Z1a.117 | H | Me | H | B1 | Cl | H | C≡C—C-i-Pr | H | Cl |
| Z1a.118 | H | Me | H | B1 | Cl | H | C≡C—CH$_2$OMe | H | Cl |
| Z1a.119 | H | Me | H | B1 | Cl | H | C≡C-p-Cl-phenyl | H | Cl |
| Z1a.120 | H | Me | H | B1 | Cl | H | p-Cl-phenyl | H | Cl |
| Z1a.121 | H | Me | H | B1 | Cl | H | CHO | H | Cl |
| Z1a.122 | H | Me | H | B1 | Cl | H | CH=NOMe | H | Cl |
| Z1a.123 | H | Me | H | B1 | Cl | H | COMe | H | Cl |
| Z1a.124 | H | Me | H | B1 | Cl | H | C(Me)=NOMe | H | Cl |
| Z1a.125 | H | Me | H | B1 | Cl | H | NO$_2$ | H | Cl |
| Z1a.126 | H | Me | H | B1 | Cl | H | NH$_2$ | H | Cl |
| Z1a.127 | H | Me | H | B1 | Cl | H | NHMe | H | Cl |
| Z1a.128 | H | Me | H | B1 | Cl | H | N(Me)$_2$ | H | Cl |
| Z1a.129 | H | Me | H | B1 | Cl | H | NHCOMe | H | Cl |
| Z1a.130 | H | Me | H | B1 | Cl | H | N=CHNEt(Me) | H | Cl |
| Z1a.131 | H | Me | H | B1 | Cl | H | OCF$_3$ | H | Cl |
| Z1a.132 | H | Me | H | B1 | Cl | H | OCH$_2$CH=CHCl$_2$ | H | Cl |
| Z1a.133 | H | Me | H | B1 | Cl | H | p-Cl-phenoxy | H | Cl |
| Z1a.134 | H | Me | H | B1 | Cl | Me | Cl | H | Cl |
| Z1a.135 | H | Me | H | B1 | Cl | Cl | Cl | H | Cl |
| Z1a.136 | H | Me | H | B1 | Cl | H | Cl | Cl | Cl |
| Z1a.137 | H | Me | H | B1 | Cl | Cl | Cl | Cl | Cl |
| Z1a.138 | H | Me | H | B1 | Cl | H | H | H | Me |
| Z1a.139 | H | Me | H | B1 | Cl | H | Cl | H | Me |
| Z1a.140 | H | Me | H | B1 | Cl | H | Br | H | Me |
| Z1a.141 | H | Me | H | B1 | Cl | H | CF$_3$ | H | Me |
| Z1a.142 | H | Me | H | B1 | Cl | H | C≡C—H | H | Me |
| Z1a.143 | H | Me | H | B1 | Cl | H | C≡C—CH$_2$OMe | H | Me |
| Z1a.144 | H | Me | H | B1 | Cl | H | C(Me)=NOMe | H | Me |
| Z1a.145 | H | Me | H | B1 | Cl | H | H | H | CHO |
| Z1a.146 | H | Me | H | B1 | Cl | H | Cl | H | CHO |
| Z1a.147 | H | Me | H | B1 | Cl | H | Br | H | CHO |
| Z1a.148 | H | Me | H | B1 | Cl | H | CF$_3$ | H | CHO |
| Z1a.149 | H | Me | H | B1 | Cl | H | C≡C—H | H | CHO |
| Z1a.150 | H | Me | H | B1 | Cl | H | C≡C—CH$_2$OMe | H | CHO |
| Z1a.151 | H | Me | H | B1 | Cl | H | C(Me)=NOMe | H | CHO |
| Z1a.152 | H | Me | H | B1 | Cl | H | H | H | OMe |
| Z1a.153 | H | Me | H | B1 | Cl | H | Cl | H | OMe |
| Z1a.154 | H | Me | H | B1 | Cl | H | Br | H | OMe |
| Z1a.155 | H | Me | H | B1 | Cl | H | CF$_3$ | H | OMe |
| Z1a.156 | H | Me | H | B1 | Cl | H | C≡C—H | H | OMe |
| Z1a.157 | H | Me | H | B1 | Cl | H | C≡C—CH$_2$OMe | H | OMe |
| Z1a.158 | H | Me | H | B1 | Cl | H | C(Me)=NOMe | H | OMe |
| Z1a.159 | H | Me | H | B1 | OMe | H | H | H | OMe |
| Z1a.160 | H | Me | H | B1 | OMe | H | Cl | H | OMe |
| Z1a.161 | H | Me | H | B1 | OMe | H | Br | H | OMe |
| Z1a.162 | H | Me | H | B1 | OMe | H | CF$_3$ | H | OMe |
| Z1a.163 | H | Me | H | B1 | OMe | H | C≡C—H | H | OMe |
| Z1a.164 | H | Me | H | B1 | OMe | H | C≡C—CH$_2$OMe | H | OMe |
| Z1a.165 | H | Me | H | B1 | OMe | H | C(Me)=NOMe | H | OMe |
| Z1a.166 | H | Me | H | B1 | Me | H | H | H | Me |
| Z1a.167 | H | Me | H | B1 | Me | H | Cl | H | Me |
| Z1a.168 | H | Me | H | B1 | Me | H | Br | H | Me |
| Z1a.169 | H | Me | H | B1 | Me | H | I | H | Me |
| Z1a.170 | H | Me | H | B1 | Me | H | CF$_3$ | H | Me |
| Z1a.171 | H | Me | H | B1 | Me | H | C≡C—H | H | Me |
| Z1a.172 | H | Me | H | B1 | Me | H | Me | H | Me |
| Z1a.173 | H | Me | H | B1 | Me | H | C≡C—CH$_2$OMe | H | Me |
| Z1a.174 | H | Me | H | B1 | Me | H | C(Me)=NOMe | H | Me |
| Z1a.175 | H | Me | H | B1 | Me | H | NO$_2$ | H | Me |
| Z1a.176 | H | Me | H | B1 | Me | H | NH$_2$ | H | Me |
| Z1a.177 | H | Me | H | B1 | Me | H | NHCOMe | H | Me |
| Z1a.178 | H | Me | H | B1 | Me | H | p-Cl-phenyl | H | Me |
| Z1a.179 | H | Me | H | B1 | Me | H | H | H | CHO |
| Z1a.180 | H | Me | H | B1 | Me | H | Cl | H | CHO |

TABLE 8a-continued

| Cpd No. | $R_2$ | $R_1$ | $R_3$ | B | $R_{10}$ | $R_{11}$ | $R_{12}$ | $R_{13}$ | $R_{14}$ |
|---|---|---|---|---|---|---|---|---|---|
| Z1a.181 | H | Me | H | B1 | Me | H | Br | H | CHO |
| Z1a.182 | H | Me | H | B1 | i-Pr | H | H | H | i-Pr |
| Z1a.183 | H | Me | H | B1 | i-Pr | H | Cl | H | i-Pr |
| Z1a.184 | H | Me | H | B1 | i-Pr | H | Br | H | i-Pr |
| Z1a.185 | H | Me | H | B1 | t-Bu | H | H | H | t-Bu |
| Z1a.186 | H | Me | H | B1 | t-Bu | H | Cl | H | t-Bu |
| Z1a.187 | H | Me | H | B1 | t-Bu | H | Me | H | t-Bu |
| Z1a.188 | H | Me | H | B1 | t-Bu | H | t-Bu | H | t-Bu |
| Z1a.189 | H | Me | H | B1 | t-Bu | H | p-Cl-phenyl | H | t-Bu |
| Z1a.190 | H | Me | H | B1 | H | H | $CF_3$ | H | H |
| Z1a.191 | H | Me | H | B1 | H | H | Br | H | H |
| Z1a.192 | H | Me | H | B1 | Br | H | H | H | Br |
| Z1a.193 | H | Me | H | B1 | Br | H | Br | H | Br |
| Z1a.194 | H | Me | H | B1 | F | H | H | H | F |
| Z1a.195 | H | Me | H | B1 | F | H | Cl | H | F |
| Z1a.196 | H | Me | H | B1 | F | H | Br | H | F |
| Z1a.197 | H | Me | H | B1 | I | H | H | H | I |
| Z1a.198 | H | Me | H | B1 | I | H | Cl | H | I |
| Z1a.199 | H | Me | H | B1 | I | H | Br | H | I |
| Z1a.200 | H | Me | H | B1 | I | H | I | H | I |
| Z1a.201 | H | Me | Me | B1 | Cl | H | H | H | Cl |
| Z1a.202 | H | Me | Me | B1 | Cl | H | Cl | H | Cl |
| Z1a.203 | H | Me | Me | B1 | Br | H | H | H | Br |
| Z1a.204 | H | Me | Me | B1 | Br | H | Br | H | Br |
| Z1a.205 | H | Me | Me | B1 | Me | H | H | H | Me |
| Z1a.206 | H | Me | Me | B1 | Me | H | Cl | H | Me |
| Z1a.207 | H | Me | Me | B1 | Me | H | Br | H | Me |
| Z1a.208 | H | Me | H | B1 | Cl | H | H | H | Cl |
| Z1a.209 | Me | Me | H | B1 | Cl | H | Cl | H | Cl |
| Z1a.210 | Me | Me | H | B1 | Br | H | H | H | Br |
| Z1a.211 | Me | Me | H | B1 | Br | H | H | H | Br |
| Z1a.212 | Me | Me | H | B1 | Me | H | Cl | H | Me |
| Z1a.213 | Me | Me | H | B1 | Me | H | Br | H | Me |
| Z1a.214 | i-Pr | Me | H | B1 | Me | H | H | H | Me |
| Z1a.215 | c-Pr | Me | H | B1 | Me | H | H | H | Me |
| Z1a.216 | Et | Et | H | B1 | Me | H | H | H | Me |
| Z1a.217 | Et | Et | H | B1 | Me | H | Br | H | Me |
| Z1a.218 | $CH_2CH_2$ | | H | B1 | Cl | H | H | H | H |
| Z1a.219 | $CH_2CH_2$ | | H | B1 | Me | H | H | H | Me |
| Z1a.220 | $CH_2CH_2$ | | H | B1 | Me | H | Br | H | Me |
| Z1a.221 | $CH_2CH_2$ | | H | B1 | H | H | Cl | H | H |
| Z1a.222 | $CH_2CH_2$ | | H | B1 | Cl | H | Cl | H | H |
| Z1a.223 | $CH_2CH_2$ | | H | B1 | Cl | H | H | H | Cl |
| Z1a.224 | $CH_2CH_2$ | | H | B1 | Cl | H | Cl | H | Cl |
| Z1a.225 | $CH_2CH_2$ | | H | B1 | Br | H | H | H | Br |
| Z1a.226 | $CH_2CH_2$ | | H | B1 | Br | H | Br | H | Br |
| Z1a.227 | H | | $CH_2$ | B1 | Me | H | H | H | Me |
| Z1a.228 | H | | $CH_2$ | B1 | Me | H | Br | H | Me |
| Z1a.229 | H | | $CH_2$ | B1 | H | H | Cl | H | H |
| Z1a.230 | H | | $CH_2$ | B1 | Cl | H | Cl | H | H |
| Z1a.231 | H | | $CH_2$ | B1 | Cl | H | H | H | Cl |
| Z1a.232 | H | | $CH_2$ | B1 | Cl | H | Cl | H | Cl |
| Z1a.233 | H | | $CH_2$ | B1 | Br | H | H | H | Br |
| Z1a.234 | H | | $CH_2$ | B1 | Br | H | Br | H | Br |
| Z1a.235 | H | H | H | B2 | Cl | H | Cl | H | — |
| Z1a.236 | H | H | H | B2 | Cl | H | Br | H | — |
| Z1a.237 | H | H | H | B2 | Br | H | Br | H | — |
| Z1a.238 | H | H | H | B2 | Cl | H | $CF_3$ | H | — |
| Z1a.239 | H | Me | H | B2 | Cl | H | $CF_3$ | H | — |
| Z1a.240 | H | Et | H | B2 | Cl | H | $CF_3$ | H | — |
| Z1a.241 | Me | Me | H | B2 | Cl | H | $CF_3$ | H | — |
| Z1a.242 | H | H | Me | B2 | Cl | H | $CF_3$ | H | — |
| Z1a.243 | H | Et | H | B2 | Cl | H | $CF_3$ | H | — |
| Z1a.244 | $CH_2CH_2$ | | H | B2 | Cl | H | $CF_3$ | H | — |
| Z1a.245 | H | | $CH_2$ | B2 | Cl | H | $CF_3$ | H | — |
| Z1a.246 | H | H | H | B3 | Cl | H | H | Cl | — |
| Z1a.247 | H | H | H | B3 | Cl | H | H | Br | — |
| Z1a.248 | H | H | H | B3 | Cl | H | H | I | — |
| Z1a.249 | H | H | H | B3 | Cl | H | H | Me | — |
| Z1a.250 | H | H | H | B3 | Me | H | H | Cl | — |
| Z1a.251 | H | H | H | B3 | Me | H | H | Br | — |
| Z1a.252 | H | H | H | B3 | Me | H | H | Me | — |
| Z1a.253 | H | Me | H | B3 | Cl | H | H | Cl | — |
| Z1a.254 | H | Me | H | B3 | Me | H | H | Cl | — |
| Z1a.255 | H | H | H | B4 | Cl | H | H | Cl | — |
| Z1a.256 | H | H | H | B4 | Br | H | H | Br | — |
| Z1a.247 | H | H | H | B4 | Me | H | H | Me | — |
| Z1a.258 | H | Me | H | B4 | Cl | H | H | Cl | — |

TABLE 8a-continued

| Cpd No. | R₂ | R₁ | R₃ | B | R₁₀ | R₁₁ | R₁₂ | R₁₃ | R₁₄ |
|---|---|---|---|---|---|---|---|---|---|
| Z1a.259 | H | Me | H | B4 | Br | H | H | Br | — |
| Z1a.260 | H | Me | H | B4 | Me | H | H | Me | — |
| Z1a.261 | H | H | H | B5 | Me | H | Me | — | — |
| Z1a.262 | H | H | H | B5 | Me | H | Me | — | — |
| Z1a.263 | H | H | H | B5 | H | Me | H | — | — |
| Z1a.264 | H | H | H | B5 | H | Cl | H | — | — |
| Z1a.265 | H | H | H | B5 | H | Br | H | — | — |
| Z1a.266 | H | H | H | B5 | H | CF₃ | H | — | — |
| Z1a.267 | H | Me | H | B5 | Me | H | Me | — | — |
| Z1a.268 | H | Me | H | B5 | Me | H | Me | — | — |
| Z1a.269 | H | Me | H | B5 | H | Me | H | — | — |
| Z1a.270 | H | Me | H | B5 | H | Cl | H | — | — |
| Z1a.271 | H | Me | H | B5 | H | Br | H | — | — |
| Z1a.272 | H | Me | H | B5 | H | CF₃ | H | — | — |
| Z1a.273 | H | H | H | B20 | Cl | H | H | H | H |
| Z1a.274 | H | H | H | B20 | Cl | H | Cl | H | H |
| Z1a.275 | H | H | H | B20 | Br | H | H | H | H |
| Z1a.276 | H | H | H | B20 | Br | H | Br | H | H |
| Z1a.277 | H | H | H | B20 | Me | H | H | H | H |
| Z1a.278 | H | H | H | B20 | CF₃ | H | H | H | H |
| Z1a.279 | H | H | H | B20 | COMe | H | H | H | H |
| Z1a.280 | H | H | H | B20 | Cl | H | H | Cl | H |
| Z1a.281 | H | Me | H | B20 | Cl | H | H | H | H |
| Z1a.282 | H | Me | H | B20 | Cl | H | Cl | H | H |
| Z1a.283 | H | Me | H | B20 | Br | H | H | H | H |
| Z1a.284 | H | Me | H | B20 | Br | H | Br | H | H |
| Z1a.285 | H | Me | H | B20 | Me | H | H | H | H |
| Z1a.286 | H | Me | H | B20 | CF₃ | H | H | H | H |
| Z1a.287 | H | Me | H | B20 | COMe | H | H | H | H |
| Z1a.288 | H | Me | H | B20 | Cl | H | H | Cl | H |
| Z1a.289 | H | H | H | B21 | Cl | H | H | H | H |
| Z1a.290 | H | H | H | B21 | H | Cl | H | H | H |
| Z1a.291 | H | H | H | B21 | Cl | Cl | H | H | H |
| Z1a.292 | H | H | H | B21 | H | H | H | Cl | H |
| Z1a.293 | H | H | H | B21 | Cl | H | H | Cl | H |
| Z1a.294 | H | H | H | B21 | H | Cl | H | Cl | H |
| Z1a.295 | H | H | H | B21 | Cl | Cl | H | Cl | H |
| Z1a.296 | H | H | H | B21 | Br | H | H | H | H |
| Z1a.297 | H | H | H | B21 | CF₃ | H | H | H | H |
| Z1a.298 | H | H | H | B21 | Me | H | H | H | H |
| Z1a.299 | H | H | H | B21 | Cl | H | H | H | H |
| Z1a.300 | H | H | H | B21 | Br | H | H | Cl | H |
| Z1a.301 | H | H | H | B21 | CF₃ | H | H | Cl | H |
| Z1a.302 | H | H | H | B21 | Me | H | H | Cl | H |
| Z1a.303 | H | H | H | B21 | Cl | H | H | Cl | H |
| Z1a.304 | H | Me | H | B21 | Cl | H | H | H | H |
| Z1a.305 | H | Me | H | B21 | H | Cl | H | H | H |
| Z1a.306 | H | Me | H | B21 | Cl | Cl | H | H | H |
| Z1a.307 | H | Me | H | B21 | H | H | H | Cl | H |
| Z1a.308 | H | Me | H | B21 | Cl | H | H | Cl | H |
| Z1a.309 | H | Me | H | B21 | H | Cl | H | Cl | H |
| Z1a.310 | H | Me | H | B21 | Cl | Cl | H | Cl | H |
| Z1a.311 | H | Me | H | B21 | Br | H | H | H | H |
| Z1a.312 | H | Me | H | B21 | CF₃ | H | H | H | H |
| Z1a.313 | H | Me | H | B21 | Me | H | H | H | H |
| Z1a.314 | H | Me | H | B21 | Cl | H | H | H | H |
| Z1a.315 | H | Me | H | B21 | Br | H | H | Cl | H |
| Z1a.316 | H | Me | H | B21 | CF₃ | H | H | Cl | H |
| Z1a.317 | H | Me | H | B21 | Me | H | H | Cl | H |
| Z1a.318 | H | Me | H | B21 | Cl | H | H | Cl | H |
| Z1a.319 | H | H | H | B22 | Me | H | H | H | H |
| Z1a.320 | H | H | H | B22 | H | H | H | H | Cl |
| Z1a.321 | H | H | H | B22 | Me | H | H | H | Cl |
| Z1a.322 | H | H | H | B22 | H | H | H | Cl | Cl |
| Z1a.323 | H | H | H | B22 | H | H | H | NO₂ | Cl |
| Z1a.324 | H | H | H | B22 | H | H | H | Me | Cl |
| Z1a.325 | H | H | H | B22 | H | H | H | H | Br |
| Z1a.326 | H | H | H | B22 | H | H | H | Cl | Br |
| Z1a.327 | H | H | H | B22 | H | H | H | Me | Br |
| Z1a.328 | H | H | H | B22 | H | H | H | Br | Br |
| Z1a.329 | H | Me | H | B22 | Me | H | H | H | H |
| Z1a.330 | H | Me | H | B22 | H | H | H | H | Cl |
| Z1a.331 | H | Me | H | B22 | Me | H | H | H | Cl |
| Z1a.332 | H | Me | H | B22 | H | H | H | Cl | Cl |
| Z1a.333 | H | Me | H | B22 | H | H | H | NO₂ | Cl |
| Z1a.334 | H | Me | H | B22 | H | H | H | Me | Cl |
| Z1a.335 | H | Me | H | B22 | H | H | H | H | Br |
| Z1a.336 | H | Me | H | B22 | H | H | H | Cl | Br |

TABLE 8a-continued

| Cpd No. | R$_2$ | R$_1$ | R$_3$ | B | R$_{10}$ | R$_{11}$ | R$_{12}$ | R$_{13}$ | R$_{14}$ |
|---|---|---|---|---|---|---|---|---|---|
| Z1a.337 | H | Me | H | B22 | H | H | H | Me | Br |
| Z1a.338 | H | Me | H | B22 | H | H | H | Br | Br |
| Z1a.339 | H | H | H | B23 | Cl | H | H | H | H |
| Z1a.340 | H | H | H | B23 | Cl | Cl | H | H | H |
| Z1a.341 | H | H | H | B23 | Cl | Me | H | H | H |
| Z1a.342 | H | H | H | B23 | Me | H | H | H | H |
| Z1a.343 | H | H | H | B23 | Me | Cl | H | H | H |
| Z1a.344 | H | H | H | B23 | Me | Me | H | H | H |
| Z1a.345 | H | H | H | B23 | H | H | H | H | Me |
| Z1a.346 | H | H | H | B23 | Cl | H | H | H | Me |
| Z1a.347 | H | H | H | B23 | Me | H | H | H | Me |
| Z1a.348 | H | Me | H | B23 | Cl | H | H | H | H |
| Z1a.349 | H | Me | H | B23 | Cl | Cl | H | H | H |
| Z1a.350 | H | Me | H | B23 | Cl | Me | H | H | H |
| Z1a.351 | H | Me | H | B23 | Me | H | H | H | H |
| Z1a.352 | H | Me | H | B23 | Me | Cl | H | H | H |
| Z1a.353 | H | Me | H | B23 | Me | Me | H | H | H |
| Z1a.354 | H | Me | H | B23 | H | H | H | H | Me |
| Z1a.355 | H | Me | H | B23 | Cl | H | H | H | Me |
| Z1a.356 | H | Me | H | B23 | Me | H | H | H | Me |
| Z1a.357 | H | H | H | B24 | Cl | H | H | H | H |
| Z1a.358 | H | H | H | B24 | Br | H | H | H | H |
| Z1a.359 | H | H | H | B24 | CN | H | H | H | H |
| Z1a.360 | H | H | H | B24 | Me | H | H | H | H |
| Z1a.361 | H | H | H | B24 | OMe | H | H | H | H |
| Z1a.362 | H | H | H | B24 | Cl | H | Cl | H | H |
| Z1a.363 | H | H | H | B24 | Br | H | Cl | H | H |
| Z1a.364 | H | H | H | B24 | CN | H | Cl | H | H |
| Z1a.365 | H | H | H | B24 | Me | H | Cl | H | H |
| Z1a.366 | H | H | H | B24 | OMe | H | Cl | H | H |
| Z1a.367 | H | H | H | B24 | Cl | H | F | H | H |
| Z1a.368 | H | H | H | B24 | Br | H | F | H | H |
| Z1a.369 | H | H | H | B24 | CN | H | F | H | H |
| Z1a.370 | H | H | H | B24 | Me | H | F | H | H |
| Z1a.371 | H | H | H | B24 | OMe | H | F | H | H |
| Z1a.372 | H | H | H | B24 | Cl | H | H | H | F |
| Z1a.373 | H | Me | H | B24 | Cl | H | H | H | H |
| Z1a.374 | H | Me | H | B24 | Br | H | H | H | H |
| Z1a.375 | H | Me | H | B24 | CN | H | H | H | H |
| Z1a.376 | H | Me | H | B24 | Me | H | H | H | H |
| Z1a.377 | H | Me | H | B24 | OMe | H | H | H | H |
| Z1a.378 | H | Me | H | B24 | Cl | H | Cl | H | H |
| Z1a.379 | H | Me | H | B24 | Br | H | Cl | H | H |
| Z1a.380 | H | Me | H | B24 | CN | H | Cl | H | H |
| Z1a.381 | H | Me | H | B24 | Me | H | Cl | H | H |
| Z1a.382 | H | Me | H | B24 | OMe | H | Cl | H | H |
| Z1a.383 | H | Me | H | B24 | Cl | H | F | H | H |
| Z1a.384 | H | Me | H | B24 | Br | H | F | H | H |
| Z1a.385 | H | Me | H | B24 | CN | H | F | H | H |
| Z1a.386 | H | Me | H | B24 | Me | H | F | H | H |
| Z1a.387 | H | Me | H | B24 | OMe | H | F | H | H |
| Z1a.388 | H | Me | H | B24 | Cl | H | H | H | F |
| Z1a.389 | H | Me | H | B25 | Me | H | H | H | H |
| Z1a.390 | H | Me | H | B25 | Cl | H | H | H | H |
| Z1a.391 | H | Me | H | B25 | OMe | H | H | H | H |
| Z1a.392 | H | Me | H | B26 | Me | H | H | H | H |
| Z1a.393 | H | Me | H | B26 | Cl | H | H | H | H |
| Z1a.394 | H | Me | H | B26 | OMe | H | H | H | H |
| Z1a.395 | H | Me | H | B28 | H | H | Me | Me | H |
| Z1a.396 | H | Me | H | B28 | Me | Me | Me | Me | H |
| Z1a.397 | H | Me | H | B29 | H | H | H | Me | Me |
| Z1a.398 | H | Me | H | B29 | Me | Me | H | Me | Me |

Table 9 Compounds of Formula IVA
The invention is further illustrated by the preferred individual compounds of formula (IVA)
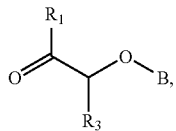
(IVA)
wherein B is one of the preferred groups B1 to B5 or B20 to B26, B28 or B29:
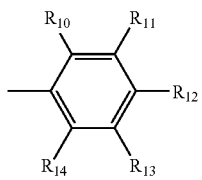
B₁
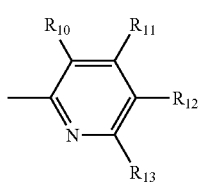
B₂
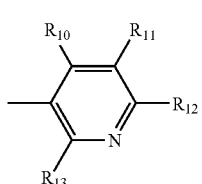
B₃
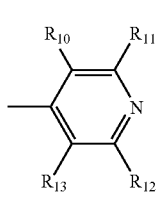
B₄
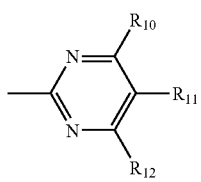
B₅
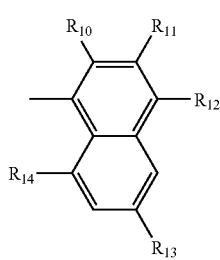
B₂₀
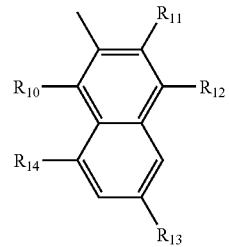
B₂₁
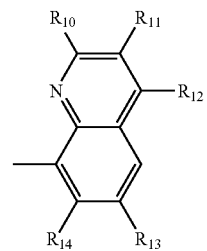
B₂₂
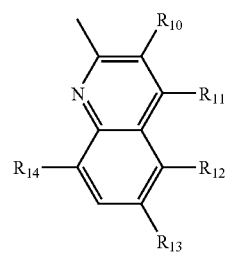
B₂₃
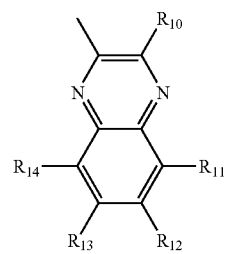
B₂₄
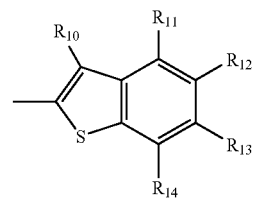
B₂₅
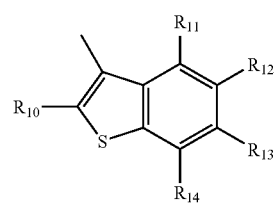
B₂₆

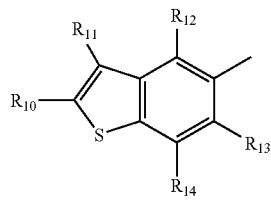

B28

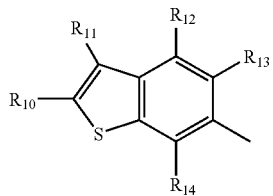

B29

The compound of formula IVA are listed below in Table 9. Characterising data is given in Table 12.

TABLE 9

| Cpd No. | $R_1$ | $R_3$ | B | $R_{10}$ | $R_{11}$ | $R_{12}$ | $R_{13}$ | $R_{14}$ |
|---|---|---|---|---|---|---|---|---|
| Z2.001 | H | H | B1 | Cl | H | H | H | H |
| Z2.002 | H | H | B1 | Cl | Cl | H | H | H |
| Z2.003 | H | H | B1 | Cl | H | Cl | H | H |
| Z2.004 | H | H | B1 | Cl | H | H | Cl | H |
| Z2.005 | H | H | B1 | Cl | H | H | H | Cl |
| Z2.006 | H | H | B1 | H | Cl | Cl | H | H |
| Z2.007 | H | H | B1 | H | Cl | H | Cl | H |
| Z2.008 | H | H | B1 | Cl | H | Cl | H | Cl |
| Z2.009 | H | H | B1 | Cl | H | Br | H | Cl |
| Z2.010 | H | H | B1 | Cl | H | I | H | Cl |
| Z2.011 | H | H | B1 | Cl | H | CHF$_2$ | H | Cl |
| Z2.012 | H | H | B1 | Cl | H | CF$_3$ | H | Cl |
| Z2.013 | H | H | B1 | Cl | H | C≡C—H | H | Cl |
| Z2.014 | H | H | B1 | Cl | H | C≡C—Me | H | Cl |
| Z2.015 | H | H | B1 | Cl | H | C≡C—Si(Me)$_3$ | H | Cl |
| Z2.016 | H | H | B1 | Cl | H | C≡C-t-Bu | H | Cl |
| Z2.017 | H | H | B1 | Cl | H | C≡C-i-Pr | H | Cl |
| Z2.018 | H | H | B1 | Cl | H | C≡C—CH$_2$OMe | H | Cl |
| Z2.019 | H | H | B1 | Cl | H | C≡C-p-Cl-phenyl | H | Cl |
| Z2.020 | H | H | B1 | Cl | H | p-Cl-phenyl | H | Cl |
| Z2.021 | H | H | B1 | Cl | H | CHO | H | Cl |
| Z2.022 | H | H | B1 | Cl | H | CH=NOMe | H | Cl |
| Z2.023 | H | H | B1 | Cl | H | COMe | H | Cl |
| Z2.024 | H | H | B1 | Cl | H | C(Me)=NOMe | H | Cl |
| Z2.025 | H | H | B1 | Cl | H | NO$_2$ | H | Cl |
| Z2.026 | H | H | B1 | Cl | H | NH$_2$ | H | Cl |
| Z2.027 | H | H | B1 | Cl | H | NHMe | H | Cl |
| Z2.028 | H | H | B1 | Cl | H | N(Me)$_2$ | H | Cl |
| Z2.029 | H | H | B1 | Cl | H | NHCOMe | H | Cl |
| Z2.030 | H | H | B1 | Cl | H | N=CHNEt(Me) | H | Cl |
| Z2.031 | H | H | B1 | Cl | H | OCF$_3$ | H | Cl |
| Z2.032 | H | H | B1 | Cl | H | OCH$_2$CH=CHCl$_2$ | H | Cl |
| Z2.033 | H | H | B1 | Cl | H | p-Cl-phenoxy | H | Cl |
| Z2.034 | H | H | B1 | Cl | Me | Cl | H | Cl |
| Z2.035 | H | H | B1 | Cl | Cl | Cl | H | Cl |
| Z2.036 | H | H | B1 | Cl | H | Cl | Cl | Cl |
| Z2.037 | H | H | B1 | Cl | Cl | Cl | Cl | Cl |
| Z2.038 | H | H | B1 | Cl | H | H | H | Me |
| Z2.039 | H | H | B1 | Cl | H | Cl | H | Me |
| Z2.040 | H | H | B1 | Cl | H | Br | H | Me |
| Z2.041 | H | H | B1 | Cl | H | CF$_3$ | H | Me |
| Z2.042 | H | H | B1 | Cl | H | C≡C—H | H | Me |
| Z2.043 | H | H | B1 | Cl | H | C≡C—CH$_2$OMe | H | Me |
| Z2.044 | H | H | B1 | Cl | H | C(Me)=NOMe | H | Me |
| Z2.045 | H | H | B1 | Cl | H | H | H | CHO |
| Z2.046 | H | H | B1 | Cl | H | Cl | H | CHO |
| Z2.047 | H | H | B1 | Cl | H | Br | H | CHO |
| Z2.048 | H | H | B1 | Cl | H | CF$_3$ | H | CHO |
| Z2.049 | H | H | B1 | Cl | H | C≡C—H | H | CHO |
| Z2.050 | H | H | B1 | Cl | H | C≡C—CH$_2$OMe | H | CHO |
| Z2.051 | H | H | B1 | Cl | H | C(Me)=NOMe | H | CHO |
| Z2.052 | H | H | B1 | Cl | H | H | H | OMe |
| Z2.053 | H | H | B1 | Cl | H | Cl | H | OMe |
| Z2.054 | H | H | B1 | Cl | H | Br | H | OMe |
| Z2.055 | H | H | B1 | Cl | H | CF$_3$ | H | OMe |
| Z2.056 | H | H | B1 | Cl | H | C≡C—H | H | OMe |
| Z2.057 | H | H | B1 | Cl | H | C≡C—CH$_2$OMe | H | OMe |
| Z2.058 | H | H | B1 | Cl | H | C(Me)=NOMe | H | OMe |
| Z2.059 | H | H | B1 | OMe | H | H | H | OMe |
| Z2.060 | H | H | B1 | OMe | H | Cl | H | OMe |
| Z2.061 | H | H | B1 | OMe | H | Br | H | OMe |

TABLE 9-continued

| Cpd No. | R$_1$ | R$_3$ | B | R$_{10}$ | R$_{11}$ | R$_{12}$ | R$_{13}$ | R$_{14}$ |
| --- | --- | --- | --- | --- | --- | --- | --- | --- |
| Z2.062 | H | H | B1 | OMe | H | CF$_3$ | H | OMe |
| Z2.063 | H | H | B1 | OMe | H | C≡C—H | H | OMe |
| Z2.064 | H | H | B1 | OMe | H | C≡C—CH$_2$OMe | H | OMe |
| Z2.065 | H | H | B1 | OMe | H | C(Me)=NOMe | H | OMe |
| Z2.066 | H | H | B1 | Me | H | H | H | Me |
| Z2.067 | H | H | B1 | Me | H | Cl | H | Me |
| Z2.068 | H | H | B1 | Me | H | Br | H | Me |
| Z2.069 | H | H | B1 | Me | H | I | H | Me |
| Z2.070 | H | H | B1 | Me | H | CF$_3$ | H | Me |
| Z2.071 | H | H | B1 | Me | H | C≡C—H | H | Me |
| Z2.072 | H | H | B1 | Me | H | Me | H | Me |
| Z2.073 | H | H | B1 | Me | H | C≡C—CH$_2$OMe | H | Me |
| Z2.074 | H | H | B1 | Me | H | C(Me)=NOMe | H | Me |
| Z2.075 | H | H | B1 | Me | H | NO$_2$ | H | Me |
| Z2.076 | H | H | B1 | Me | H | NH$_2$ | H | Me |
| Z2.077 | H | H | B1 | Me | H | NHCOMe | H | Me |
| Z2.078 | H | H | B1 | Me | H | p-Cl-phenyl | H | Me |
| Z2.079 | H | H | B1 | Me | H | H | H | CHO |
| Z2.080 | H | H | B1 | Me | H | Cl | H | CHO |
| Z2.081 | H | H | B1 | Me | H | Br | H | CHO |
| Z2.082 | H | H | B1 | i-Pr | H | H | H | i-Pr |
| Z2.083 | H | H | B1 | i-Pr | H | Cl | H | i-Pr |
| Z2.084 | H | H | B1 | i-Pr | H | Br | H | i-Pr |
| Z2.085 | H | H | B1 | t-Bu | H | H | H | t-Bu |
| Z2.086 | H | H | B1 | t-Bu | H | Cl | H | t-Bu |
| Z2.087 | H | H | B1 | t-Bu | H | Br | H | t-Bu |
| Z2.088 | H | H | B1 | t-Bu | H | Me | H | t-Bu |
| Z2.089 | H | H | 81 | t-Bu | H | t-Bu | H | t-Bu |
| Z2.090 | H | H | B1 | t-Bu | H | OMe | H | t-Bu |
| Z2.091 | H | H | B1 | Br | H | H | H | Br |
| Z2.092 | H | H | B1 | Br | H | Br | H | Br |
| Z2.093 | H | H | B1 | F | H | H | H | F |
| Z2.094 | H | H | B1 | F | H | Cl | H | F |
| Z2.095 | H | H | B1 | F | H | Br | H | F |
| Z2.096 | H | H | B1 | I | H | H | H | I |
| Z2.097 | H | H | B1 | I | H | Cl | H | I |
| Z2.098 | Me | H | B1 | H | H | COMe | H | H |
| Z2.099 | Me | H | B1 | H | F | H | F | H |
| Z2.100 | Me | H | B1 | Me | H | Cl | H | H |
| Z2.101 | Me | H | B1 | H | Cl | Cl | H | H |
| Z2.102 | Me | H | B1 | H | t-Bu | H | t-Bu | H |
| Z2.103 | Me | H | B1 | Cl | H | Cl | H | H |
| Z2.104 | Me | H | B1 | Cl | H | H | Cl | H |
| Z2.105 | Me | H | B1 | Cl | H | H | H | Cl |
| Z2.106 | Me | H | B1 | H | Cl | Cl | H | H |
| Z2.107 | Me | H | B1 | H | Cl | H | Cl | H |
| Z2.108 | Me | H | B1 | Cl | H | Cl | H | Cl |
| Z2.109 | Me | H | B1 | Cl | H | Br | H | Cl |
| Z2.110 | Me | H | B1 | Cl | H | I | H | Cl |
| Z2.111 | Me | H | B1 | Cl | H | CHF$_2$ | H | Cl |
| Z2.112 | Me | H | B1 | Cl | H | CF$_3$ | H | Cl |
| Z2.113 | Me | H | B1 | Cl | H | C≡C—H | H | Cl |
| Z2.114 | Me | H | B1 | Cl | H | C≡C—Me | H | Cl |
| Z2.115 | Me | H | B1 | Cl | H | C≡C—Si(Me)$_3$ | H | Cl |
| Z2.116 | Me | H | B1 | Cl | H | C≡C-t-Bu | H | Cl |
| Z2.117 | Me | H | B1 | Cl | H | C≡C-i-Pr | H | Cl |
| Z2.118 | Me | H | B1 | Cl | H | C≡C—CH$_2$OMe | H | Cl |
| Z2.119 | Me | H | B1 | Cl | H | C≡C-p-Cl-phenyl | H | Cl |
| Z2.120 | Me | H | B1 | Cl | H | p-Cl-phenyl | H | Cl |
| Z2.121 | Me | H | B1 | Cl | H | CHO | H | Cl |
| Z2.122 | Me | H | B1 | Cl | H | CH=NOMe | H | Cl |
| Z2.123 | Me | H | B1 | Cl | H | COMe | H | Cl |
| Z2.124 | Me | H | B1 | Cl | H | C(Me)=NOMe | H | Cl |
| Z2.125 | Me | H | B1 | Cl | H | NO$_2$ | H | Cl |
| Z2.126 | Me | H | B1 | Cl | H | NH$_2$ | H | Cl |
| Z2.127 | Me | H | B1 | Cl | H | NHMe | H | Cl |
| Z2.128 | Me | H | B1 | Cl | H | N(Me)$_2$ | H | Cl |
| Z2.129 | Me | H | B1 | Cl | H | NHCOMe | H | Cl |
| Z2.130 | Me | H | B1 | Cl | H | N=CHNEt(Me) | H | Cl |
| Z2.131 | Me | H | B1 | Cl | H | OCF$_3$ | H | Cl |
| Z2.132 | Me | H | B1 | Cl | H | OCH$_2$CH=CHCl$_2$ | H | Cl |
| Z2.133 | Me | H | B1 | Cl | H | p-Cl-phenoxy | H | Cl |
| Z2.134 | Me | H | B1 | Cl | Me | Cl | H | Cl |
| Z2.135 | Me | H | B1 | Cl | Cl | Cl | H | Cl |
| Z2.136 | Me | H | B1 | Cl | H | Cl | Cl | Cl |
| Z2.137 | Me | H | B1 | Cl | Cl | Cl | Cl | Cl |
| Z2.138 | Me | H | B1 | Cl | H | H | H | Me |
| Z2.139 | Me | H | B1 | Cl | H | Cl | H | Me |

TABLE 9-continued

| Cpd No. | R₁ | R₃ | B | R₁₀ | R₁₁ | R₁₂ | R₁₃ | R₁₄ |
|---|---|---|---|---|---|---|---|---|
| Z2.140 | Me | H | B1 | Cl | H | Br | H | Me |
| Z2.141 | Me | H | B1 | Cl | H | CF₃ | H | Me |
| Z2.142 | Me | H | B1 | Cl | H | C≡C—H | H | Me |
| Z2.143 | Me | H | B1 | Cl | H | C≡C—CH₂OMe | H | Me |
| Z2.144 | Me | H | B1 | Cl | H | C(Me)=NOMe | H | Me |
| Z2.145 | Me | H | B1 | Cl | H | H | H | CHO |
| Z2.146 | Me | H | B1 | Cl | H | Cl | H | CHO |
| Z2.147 | Me | H | B1 | Cl | H | Br | H | CHO |
| Z2.148 | Me | H | B1 | Cl | H | CF₃ | H | CHO |
| Z2.149 | Me | H | B1 | Cl | H | C≡C—H | H | CHO |
| Z2.150 | Me | H | B1 | Cl | H | C≡C—CH₂OMe | H | CHO |
| Z2.151 | Me | H | B1 | Cl | H | C(Me)=NOMe | H | CHO |
| Z2.152 | Me | H | B1 | Cl | H | H | H | OMe |
| Z2.153 | Me | H | B1 | Cl | H | Cl | H | OMe |
| Z2.154 | Me | H | B1 | Cl | H | Br | H | OMe |
| Z2.155 | Me | H | B1 | Cl | H | CF₃ | H | OMe |
| Z2.156 | Me | H | B1 | Cl | H | C≡C—H | H | OMe |
| Z2.157 | Me | H | B1 | Cl | H | C≡C—CH₂OMe | H | OMe |
| Z2.158 | Me | H | B1 | Cl | H | C(Me)=NOMe | H | OMe |
| Z2.159 | Me | H | B1 | OMe | H | H | H | OMe |
| Z2.160 | Me | H | B1 | OMe | H | Cl | H | OMe |
| Z2.161 | Me | H | B1 | OMe | H | Br | H | OMe |
| Z2.162 | Me | H | B1 | OMe | H | CF₃ | H | OMe |
| Z2.163 | Me | H | B1 | OMe | H | C≡C—H | H | OMe |
| Z2.164 | Me | H | B1 | OMe | H | C≡C—CH₂OMe | H | OMe |
| Z2.165 | Me | H | B1 | OMe | H | C(Me)=NOMe | H | OMe |
| Z2.166 | Me | H | B1 | Me | H | H | H | Me |
| Z2.167 | Me | H | B1 | Me | H | Cl | H | Me |
| Z2.168 | Me | H | B1 | Me | H | Br | H | Me |
| Z2.169 | Me | H | B1 | Me | H | I | H | Me |
| Z2.170 | Me | H | B1 | Me | H | CF₃ | H | Me |
| Z2.171 | Me | H | B1 | Me | H | C≡C—H | H | Me |
| Z2.172 | Me | H | B1 | Me | H | Me | H | Me |
| Z2.173 | Me | H | B1 | Me | H | C≡C—CH₂OMe | H | Me |
| Z2.174 | Me | H | B1 | Me | H | C(Me)=NOMe | H | Me |
| Z2.175 | Me | H | B1 | Me | H | NO₂ | H | Me |
| Z2.176 | Me | H | B1 | Me | H | NH₂ | H | Me |
| Z2.177 | Me | H | B1 | Me | H | NHCOMe | H | Me |
| Z2.178 | Me | H | B1 | Me | H | p-Cl-phenyl | H | Me |
| Z2.179 | Me | H | B1 | Me | H | H | H | CHO |
| Z2.180 | Me | H | B1 | Me | H | Cl | H | CHO |
| Z2.181 | Me | H | B1 | Me | H | Br | H | CHO |
| Z2.182 | Me | H | B1 | i-Pr | H | H | H | i-Pr |
| Z2.183 | Me | H | B1 | i-Pr | H | Cl | H | i-Pr |
| Z2.184 | Me | H | B1 | i-Pr | H | Br | H | i-Pr |
| Z2.185 | Me | H | B1 | t-Bu | H | H | H | t-Bu |
| Z2.186 | Me | H | B1 | t-Bu | H | Cl | H | t-Bu |
| Z2.187 | Me | H | B1 | t-Bu | H | Me | H | t-Bu |
| Z2.188 | Me | H | B1 | t-Bu | H | t-Bu | H | t-Bu |
| Z2.189 | Me | H | B1 | t-Bu | H | p-Cl-phenyl | H | t-Bu |
| Z2.190 | Me | H | B1 | H | H | CF₃ | H | H |
| Z2.191 | Me | H | B1 | H | H | Br | H | H |
| Z2.192 | Me | H | B1 | Br | H | H | H | Br |
| Z2.193 | Me | H | B1 | Br | H | Br | H | Br |
| Z2.194 | Me | H | B1 | F | H | H | H | F |
| Z2.195 | Me | H | B1 | F | H | Cl | H | F |
| Z2.196 | Me | H | B1 | F | H | Br | H | F |
| Z2.197 | Me | H | B1 | I | H | H | H | I |
| Z2.198 | Me | H | B1 | I | H | Cl | H | I |
| Z2.199 | Me | H | B1 | I | H | Br | H | I |
| Z2.200 | Me | H | B1 | I | H | I | H | I |
| Z2.201 | Me | Me | B1 | Cl | H | H | H | Cl |
| Z2.202 | Me | Me | B1 | Cl | H | Cl | H | Cl |
| Z2.203 | Me | Me | B1 | Br | H | H | H | Br |
| Z2.204 | Me | Me | B1 | Br | H | Br | H | Br |
| Z2.205 | Me | Me | B1 | Me | H | H | H | Me |
| Z2.206 | Me | Me | B1 | Me | H | Cl | H | Me |
| Z2.207 | Me | Me | B1 | Me | H | Br | H | Me |
| Z2.208 | Me | H | B1 | Cl | H | H | H | Cl |
| Z2.209 | Et | H | B1 | Me | H | H | H | Me |
| Z2.210 | Et | H | B1 | Me | H | Br | H | Me |
| Z2.211 | H | H | B2 | Cl | H | Cl | H | — |
| Z2.212 | H | H | B2 | Cl | H | Br | H | — |
| Z2.213 | H | H | B2 | Br | H | Br | H | — |
| Z2.214 | H | H | B2 | Cl | H | CF₃ | H | — |
| Z2.215 | Me | H | B2 | Cl | H | CF₃ | H | — |
| Z2.216 | Et | H | B2 | Cl | H | CF₃ | H | — |
| Z2.217 | H | Me | B2 | Cl | H | CF₃ | H | — |

TABLE 9-continued

| Cpd No. | $R_1$ | $R_3$ | B | $R_{10}$ | $R_{11}$ | $R_{12}$ | $R_{13}$ | $R_{14}$ |
|---|---|---|---|---|---|---|---|---|
| Z2.218 | Et | H | B2 | Cl | H | $CF_3$ | H | — |
| Z2.219 | H | H | B3 | Cl | H | H | Cl | — |
| Z2.220 | H | H | B3 | Cl | H | H | Br | — |
| Z2.221 | H | H | B3 | Cl | H | H | I | — |
| Z2.222 | H | H | B3 | Cl | H | H | Me | — |
| Z2.223 | H | H | B3 | Me | H | H | Cl | — |
| Z2.224 | H | H | B3 | Me | H | H | Br | — |
| Z2.225 | H | H | B3 | Me | H | H | Me | — |
| Z2.226 | Me | H | B3 | Cl | H | H | Cl | — |
| Z2.227 | Me | H | B3 | Me | H | H | Cl | — |
| Z2.228 | H | H | B4 | Cl | H | H | Cl | — |
| Z2.229 | H | H | B4 | Br | H | H | Br | — |
| Z2.230 | H | H | B4 | Me | H | H | Me | — |
| Z2.231 | Me | H | B4 | Cl | H | H | Cl | — |
| Z2.232 | Me | H | B4 | Br | H | H | Br | — |
| Z2.233 | Me | H | B4 | Me | H | H | Me | — |
| Z2.234 | H | H | B5 | Me | H | Me | — | — |
| Z2.235 | H | H | B5 | Me | H | Me | — | — |
| Z2.236 | H | H | B5 | H | Me | H | — | — |
| Z2.237 | H | H | B5 | H | Cl | H | — | — |
| Z2.238 | H | H | B5 | H | Br | H | — | — |
| Z2.239 | H | H | B5 | H | $CF_3$ | H | — | — |
| Z2.240 | Me | H | B5 | Me | H | Me | — | — |
| Z2.241 | Me | H | B5 | Me | H | Me | — | — |
| Z2.242 | Me | H | B5 | H | Me | H | — | — |
| Z2.243 | Me | H | B5 | H | Cl | H | — | — |
| Z2.244 | Me | H | B5 | H | Br | H | — | — |
| Z2.245 | Me | H | B5 | H | $CF_3$ | H | — | — |
| Z2.246 | H | H | B20 | Cl | H | H | H | H |
| Z2.247 | H | H | B20 | Cl | H | Cl | H | H |
| Z2.248 | H | H | B20 | Br | H | H | H | H |
| Z2.249 | H | H | B20 | Br | H | Br | H | H |
| Z2.250 | H | H | B20 | Me | H | H | H | H |
| Z2.251 | H | H | B20 | $CF_3$ | H | H | H | H |
| Z2.252 | H | H | B20 | COMe | H | H | H | H |
| Z2.253 | H | H | B20 | Cl | H | H | Cl | H |
| Z2.254 | Me | H | B20 | Cl | H | H | H | H |
| Z2.255 | Me | H | B20 | Cl | H | Cl | H | H |
| Z2.256 | Me | H | B20 | Br | H | H | H | H |
| Z2.257 | Me | H | B20 | Br | H | Br | H | H |
| Z2.258 | Me | H | B20 | Me | H | H | H | H |
| Z2.259 | Me | H | B20 | $CF_3$ | H | H | H | H |
| Z2.260 | Me | H | B20 | COMe | H | H | H | H |
| Z2.261 | Me | H | B20 | Cl | H | H | Cl | H |
| Z2.262 | H | H | B21 | Cl | H | H | H | H |
| Z2.263 | H | H | B21 | H | Cl | H | H | H |
| Z2.264 | H | H | B21 | Cl | Cl | H | H | H |
| Z2.265 | H | H | B21 | H | H | H | Cl | H |
| Z2.266 | H | H | B21 | Cl | H | H | Cl | H |
| Z2.267 | H | H | B21 | H | Cl | H | Cl | H |
| Z2.268 | H | H | B21 | Cl | Cl | H | Cl | H |
| Z2.269 | H | H | B21 | Br | H | H | H | H |
| Z2.270 | H | H | B21 | $CF_3$ | H | H | H | H |
| Z2.271 | H | H | B21 | Me | H | H | H | H |
| Z2.272 | H | H | B21 | Cl | H | H | H | H |
| Z2.273 | H | H | B21 | Br | H | H | Cl | H |
| Z2.274 | H | H | B21 | $CF_3$ | H | H | Cl | H |
| Z2.275 | H | H | B21 | Me | H | H | Cl | H |
| Z2.276 | H | H | B21 | Cl | H | H | Cl | H |
| Z2.277 | Me | H | B21 | Cl | H | H | H | H |
| Z2.278 | Me | H | B21 | H | Cl | H | H | H |
| Z2.279 | Me | H | B21 | Cl | Cl | H | H | H |
| Z2.280 | Me | H | B21 | H | H | H | Cl | H |
| Z2.281 | Me | H | B21 | Cl | H | H | Cl | H |
| Z2.282 | Me | H | B21 | H | Cl | H | Cl | H |
| Z2.283 | Me | H | B21 | Cl | Cl | H | Cl | H |
| Z2.284 | Me | H | B21 | Br | H | H | H | H |
| Z2.285 | Me | H | B21 | $CF_3$ | H | H | H | H |
| Z2.286 | Me | H | B21 | Me | H | H | H | H |
| Z2.287 | Me | H | B21 | Cl | H | H | H | H |
| Z2.288 | Me | H | B21 | Br | H | H | Cl | H |
| Z2.289 | Me | H | B21 | $CF_3$ | H | H | Cl | H |
| Z2.290 | Me | H | B21 | Me | H | H | Cl | H |
| Z2.291 | Me | H | B21 | Cl | H | H | Cl | H |
| Z2.292 | H | H | B22 | Me | H | H | H | H |
| Z2.293 | H | H | B22 | H | H | H | H | Cl |
| Z2.294 | H | H | B22 | Me | H | H | H | Cl |
| Z2.295 | H | H | B22 | H | H | H | Cl | Cl |

TABLE 9-continued

| Cpd No. | R₁ | R₃ | B | R₁₀ | R₁₁ | R₁₂ | R₁₃ | R₁₄ |
|---|---|---|---|---|---|---|---|---|
| Z2.296 | H | H | B22 | H | H | H | NO₂ | Cl |
| Z2.297 | H | H | B22 | H | H | H | Me | Cl |
| Z2.298 | H | H | B22 | H | H | H | H | Br |
| Z2.299 | H | H | B22 | H | H | H | Cl | Br |
| Z2.300 | H | H | B22 | H | H | H | Me | Br |
| Z2.301 | H | H | B22 | H | H | H | Br | Br |
| Z2.302 | Me | H | B22 | Me | H | H | H | H |
| Z2.303 | Me | H | B22 | H | H | H | H | Cl |
| Z2.304 | Me | H | B22 | Me | H | H | H | Cl |
| Z2.305 | Me | H | B22 | H | H | H | Cl | Cl |
| Z2.306 | Me | H | B22 | H | H | H | NO₂ | Cl |
| Z2.307 | Me | H | B22 | H | H | H | Me | Cl |
| Z2.308 | Me | H | B22 | H | H | H | H | Br |
| Z2.309 | Me | H | B22 | H | H | H | Cl | Br |
| Z2.310 | Me | H | B22 | H | H | H | Me | Br |
| Z2.311 | Me | H | B22 | H | H | H | Br | Br |
| Z2.312 | H | H | B23 | Cl | H | H | H | H |
| Z2.313 | H | H | B23 | Cl | Cl | H | H | H |
| Z2.314 | H | H | B23 | Cl | Me | H | H | H |
| Z2.315 | H | H | B23 | Me | H | H | H | H |
| Z2.316 | H | H | B23 | Me | Cl | H | H | H |
| Z2.317 | H | H | B23 | Me | Me | H | H | H |
| Z2.318 | H | H | B23 | H | H | H | H | Me |
| Z2.319 | H | H | B23 | Cl | H | H | H | Me |
| Z2.320 | H | H | B23 | Me | H | H | H | Me |
| Z2.321 | Me | H | B23 | Cl | H | H | H | H |
| Z2.322 | Me | H | B23 | Cl | Cl | H | H | H |
| Z2.323 | Me | H | B23 | Cl | Me | H | H | H |
| Z2.324 | Me | H | B23 | Me | H | H | H | H |
| Z2.325 | Me | H | B23 | Me | Cl | H | H | H |
| Z2.326 | Me | H | B23 | Me | Me | H | H | H |
| Z2.327 | Me | H | B23 | H | H | H | H | Me |
| Z2.328 | Me | H | B23 | Cl | H | H | H | Me |
| Z2.329 | Me | H | B23 | Me | H | H | H | Me |
| Z2.330 | H | H | B24 | Cl | H | H | H | H |
| Z2.331 | H | H | B24 | Br | H | H | H | H |
| Z2.332 | H | H | B24 | CN | H | H | H | H |
| Z2.333 | H | H | B24 | Me | H | H | H | H |
| Z2.334 | H | H | B24 | OMe | H | H | H | H |
| Z2.335 | H | H | B24 | Cl | H | Cl | H | H |
| Z2.336 | H | H | B24 | Br | H | Cl | H | H |
| Z2.337 | H | H | B24 | CN | H | Cl | H | H |
| Z2.338 | H | H | B24 | Me | H | Cl | H | H |
| Z2.339 | H | H | B24 | OMe | H | Cl | H | H |
| Z2.340 | H | H | B24 | Cl | H | F | H | H |
| Z2.341 | H | H | B24 | Br | H | F | H | H |
| Z2.342 | H | H | B24 | CN | H | F | H | H |
| Z2.343 | H | H | B24 | Me | H | F | H | H |
| Z2.344 | H | H | B24 | OMe | H | F | H | H |
| Z2.345 | H | H | B24 | Cl | H | H | H | F |
| Z2.346 | Me | H | B24 | Cl | H | H | H | H |
| Z2.347 | Me | H | B24 | Br | H | H | H | H |
| Z2.348 | Me | H | B24 | CN | H | H | H | H |
| Z2.349 | Me | H | B24 | Me | H | H | H | H |
| Z2.350 | Me | H | B24 | OMe | H | H | H | H |
| Z2.351 | Me | H | B24 | Cl | H | Cl | H | H |
| Z2.352 | Me | H | B24 | Br | H | Cl | H | H |
| Z2.353 | Me | H | B24 | CN | H | Cl | H | H |
| Z2.354 | Me | H | B24 | Me | H | Cl | H | H |
| Z2.355 | Me | H | B24 | OMe | H | Cl | H | H |
| Z2.356 | Me | H | B24 | Cl | H | F | H | H |
| Z2.357 | Me | H | B24 | Br | H | F | H | H |
| Z2.358 | Me | H | B24 | CN | H | F | H | H |
| Z2.359 | Me | H | B24 | Me | H | F | H | H |
| Z2.360 | Me | H | B24 | OMe | H | F | H | H |
| Z2.361 | Me | H | B24 | Cl | H | H | H | F |
| Z2.361 | Me | H | B25 | Me | H | H | H | H |
| Z2.361 | Me | H | B25 | Cl | H | H | H | H |
| Z2.361 | Me | H | B25 | OMe | H | H | H | H |
| Z2.361 | Me | H | B26 | Me | H | H | H | H |
| Z2.361 | Me | H | B26 | Cl | H | H | H | H |
| Z2.361 | Me | H | B26 | OMe | H | H | H | H |
| Z2.361 | Me | H | B28 | H | H | Me | Me | H |
| Z2.361 | Me | H | B28 | Me | Me | Me | Me | H |
| Z2.361 | Me | H | B29 | H | H | H | Me | Me |
| Z2.361 | Me | H | B29 | Me | Me | H | Me | Me |

Table 10 Compounds of Formula XXIV:
The invention is further illustrated by the preferred individual compounds of formula (XXIV)

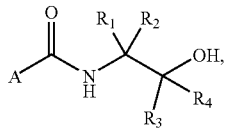

which are listed below in Table 10. Characterising data is given in Table 12.

TABLE 10

| Cpd No. | R₁ | R₂ | R₃ | R₄ | A |
|---|---|---|---|---|---|
| Z3.1 | H | H | H | H | 3-difluoromethyl-1-methyl-1H-pyrazol-4-yl |
| Z3.2 | Me | H | H | H | 3-difluoromethyl-1-methyl-1H-pyrazol-4-yl |
| Z3.3 | H | H | H | H | 3-trifluoromethyl-1-methyl-1H-pyrazol-4-yl |
| Z3.4 | Me | H | H | H | 3-trifluoromethyl-1-methyl-1H-pyrazol-4-yl |
| Z3.5 | H | H | H | H | 3-trifluoromethyl-1-methyl-pyrrol-4-yl |
| Z3.6 | Me | H | H | H | 3-trifluoromethyl-1-methyl-pyrrol-4-yl |
| Z3.7 | H | H | H | H | 3-difluoromethyl-1-methyl-1H-triazol-4-yl |
| Z3.8 | Me | H | H | H | 3-difluoromethyl-1-methyl-1H-triazol-4-yl |
| Z3.9 | H | H | H | H | 3-trifluoromethyl-1-methyl-1H-triazol-4-yl |
| Z3.10 | Me | H | H | H | 3-trifluoromethyl-1-methyl-1H-triazol-4-yl |
| Z3.11 | H | H | H | H | 4-difluoromethyl-2-methyl-thiazol-5-yl |
| Z3.12 | Me | H | H | H | 4-difluoromethyl-2-methyl-thiazol-5-yl |
| Z3.13 | H | H | H | H | 4-trifluoromethyl-2-methyl-thiazol-5-yl |
| Z3.14 | Me | H | H | H | 4-trifluoromethyl-2-methyl-thiazol-5-yl |

Table 11 Compounds of Formula XXIIB
The invention is further illustrated by the preferred individual compounds of formula (XXIIB)

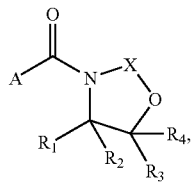

which are listed below in Table 11. Characterising data is given in Table 12.

TABLE 11

| Cpd No. | R₁ | R₂ | R₃ | R₄ | X | A |
|---|---|---|---|---|---|---|
| Z3.1 | H | H | H | H | —SO— | 3-difluoromethyl-1-methyl-1H-pyrazol-4-yl |
| Z3.2 | Me | H | H | H | —SO— | 3-difluoromethyl-1-methyl-1H-pyrazol-4-yl |
| Z3.3 | H | H | H | H | —SO— | 3-trifluoromethyl-1-methyl-1H-pyrazol-4-yl |
| Z3.4 | Me | H | H | H | —SO— | 3-trifluoromethyl-1-methyl-1H-pyrazol-4-yl |
| Z3.5 | H | H | H | H | —SO— | 3-trifluoromethyl-1-methyl-pyrrol-4-yl |
| Z3.6 | Me | H | H | H | —SO— | 3-trifluoromethyl-1-methyl-pyrrol-4-yl |
| Z3.7 | H | H | H | H | —SO— | 3-difluoromethyl-1-methyl-1H-triazol-4-yl |
| Z3.8 | Me | H | H | H | —SO— | 3-difluoromethyl-1-methyl-1H-triazol-4-yl |
| Z3.9 | H | H | H | H | —SO— | 3-trifluoromethyl-1-methyl-1H-triazol-4-yl |
| Z3.10 | Me | H | H | H | —SO— | 3-trifluoromethyl-1-methyl-1H-triazol-4-yl |
| Z3.11 | H | H | H | H | —SO— | 4-difluoromethyl-2-methyl-thiazol-5-yl |
| Z3.12 | Me | H | H | H | —SO— | 4-difluoromethyl-2-methyl-thiazol-5-yl |
| Z3.13 | H | H | H | H | —SO— | 4-trifluoromethyl-2-methyl-thiazol-5-yl |
| Z3.14 | Me | H | H | H | —SO— | 4-trifluoromethyl-2-methyl-thiazol-5-yl |
| Z3.15 | H | H | H | H | —SO₂— | 3-difluoromethyl-1-methyl-1H-pyrazol-4-yl |
| Z3.16 | Me | H | H | H | —SO₂— | 3-difluoromethyl-1-methyl-1H-pyrazol-4-yl |
| Z3.17 | H | H | H | H | —SO₂— | 3-trifluoromethyl-1-methyl-1H-pyrazol-4-yl |
| Z3.18 | Me | H | H | H | —SO₂— | 3-trifluoromethyl-1-methyl-1H-pyrazol-4-yl |
| Z3.19 | H | H | H | H | —SO₂— | 3-trifluoromethyl-1-methyl-pyrrol-4-yl |
| Z3.20 | Me | H | H | H | —SO₂— | 3-trifluoromethyl-1-methyl-pyrrol-4-yl |
| Z3.21 | H | H | H | H | —SO₂— | 3-difluoromethyl-1-methyl-1H-triazol-4-yl |
| Z3.22 | Me | H | H | H | —SO₂— | 3-difluoromethyl-1-methyl-1H-triazol-4-yl |
| Z3.23 | H | H | H | H | —SO₂— | 3-trifluoromethyl-1-methyl-1H-triazol-4-yl |
| Z3.24 | Me | H | H | H | —SO₂— | 3-trifluoromethyl-1-methyl-1H-triazol-4-yl |
| Z3.25 | H | H | H | H | —SO₂— | 4-difluoromethyl-2-methyl-thiazol-5-yl |
| Z3.26 | Me | H | H | H | —SO₂— | 4-difluoromethyl-2-methyl-thiazol-5-yl |
| Z3.27 | H | H | H | H | —SO₂— | 4-trifluoromethyl-2-methyl-thiazol-5-yl |
| Z3.28 | Me | H | H | H | —SO₂— | 4-trifluoromethyl-2-methyl-thiazol-5-yl |

Table 12: Characterising Data

Table 12 shows selected melting point and selected NMR data for compounds of Tables 1 to 11. CDCl$_3$ was used as the solvent for NMR measurements, unless otherwise stated. If a mixture of solvents was present, this is indicated as, for example: CDCl$_3$/d$_6$-DMSO). No attempt is made to list all characterising data in all cases. LCMS-data for physico-chemical characterization were obtained on an analytical Waters LC-MS instrument (W2790, ZMD-2000). Column was an Atlantis dC18, 3 um 3.0 mm×20 mm. Solvents were: A=0.1% formic acid in water, B=0.1% formic acid in aceto-nitrile. Gradient was 10% to 90% B in 2.9 min; flow rate was 1.7 ml/min. Physicochemical data are reported in the following format: retention time (min); M found in positive ionisation mode (m/z$^+$).

In Table 12 and throughout the description that follows, temperatures are given in degrees Celsius; "NMR" means nuclear magnetic resonance spectrum; MS stands for mass spectrum; "%" is percent by weight, unless corresponding concentrations are indicated in other units. The following abbreviations are used throughout this description:

| | |
|---|---|
| m.p. = melting point | b.p. = boiling point. |
| S = singlet | br = broad |
| d = doublet | dd = doublet of doublets |
| t = triplet | q = quartet |
| m = multiplet | ppm = parts per million |

TABLE 12

| Cpd No. | 1H-NMR data: ppm (multiplicity/number of Hs) | MS [M + H]$^+$ | m.p. (° C.) | LCMS data |
|---|---|---|---|---|
| 1.098 | 1.40(d, 3H, CH$_3$), 2.53(s, 3H, CH$_3$), 3.90(s, 3H, CH$_3$), 4.05-4.12(m, 2H, CH$_2$), 4.52-4.57(m, 1H, CH), 6.68(m$_{broad}$, 1H, NH), 6.71-6.98(t, 1H, CHF$_2$), 6.94-6.97(d, 2H, Ar—H), 7.90-7.94(m, 3H, 2H—Ar + 1H, pyrazole-H). | 352 | resin | — |
| 1.099 | — | — | — | 1.34 min; 346 |
| 1.100 | — | — | — | 1.57 min; 358 |
| 1.101 | — | — | — | 1.59 min; 378 |
| 1.102 | — | — | — | 2.13 min; 422 |
| 1.103 | — | — | — | 1.51 min; 378 |
| 1.104 (S)-enantiomere | | | | 1.42 min; 378 |
| 1.108 | 1.46-1.48(d, 3H), 3.93(s, 3H), 4.02-4.12(ddd, 2H), 4.49-4.55(m, 1H), 6.68(s, 1H) 6.76-7.03 (t, 1H), 7.31(s, 2H), 7.88(s, 1H). | 412.6/414.5/416.5 | 124-126 | — |
| 1.121 (S)-enantiomere | | | | 1.30 min; 406 |
| 1.125 (S)-enantiomere | | | | 1.72 min; 423 |
| 1.132 (S)-enantiomere | | | | 1.88 min; 502 |
| 1.137 (S)-enantiomere | | | | 1.87 min; 479 |
| 1.140 (S)-enantiomere | | | | 1.64 min; 436 |
| 1.166 | 1.46-1.48(d, 3H), 2.21(2s, 6H), 3.77-3.87(ddd, 2H), 3.94(s, 3H), 4.47-4.53(m, 1H), 6.76-7.03(t, 1H), 6.79(s, 1H), 6.91(d, 1H), 7.00(d, 2H), 7.93(s, 1H). | 338 | 149-146 | — |
| 1.168 | 1.44-1.46(d, 3H), 2.21(2s, 6H), 3.72-3.85(ddd, 2H), 3.89(s, 3H), 4.46-4.51(m, 1H), 6.76(s, 1H), 6.77-7.03(t, 1H), 7.11(s, 1H), 7.93(s, 1H). | 416/418 | 119-121 | — |
| 1.172 (S)-enantiomere | | | | 1.52 min; 352 |
| 1.180 (S)-enantiomere | | | | 1.39 min; 386 |
| 1.182 (S)-enantiomere | | | | 1.80 min; 394 |
| 1.185 (S)-enantiomere | | | | 2.02 min; 422 |
| 1.187 (S)-enantiomere | | | | 2.08 min; 436 |
| 1.188 (S)-enantiomere | | | | 2.31 min; 478 |
| 1.190 | 1.39-1.41(d, 3H), 3.91(s, 3H), 4.03-4.10(ddd, 2H), 4.51-4.57(m, 1H), 6.63(s, 1H) 6.66-7.93 (t, 1H), 6.98(d, 2H), 7.53-7.55(d, 2H) 7.91(s, 1H). | 378.6/379.7 | 99-102 | — |

TABLE 12-continued

| Cpd No. | 1H-NMR data: ppm (multiplicity/number of Hs) | MS [M + H]$^+$ | m.p. (° C.) | LCMS data |
|---|---|---|---|---|
| 1.191 | 1.30-1.32(d, 3H), 3.85(s, 3H), 3.89-3.95(ddd, 2H), 4.42-4.46(m, 1H), 6.59(s, 1H) 6.73-6.86 (t, 1H), 6.74(d, 2H), 7.29-7.31 (d, 2H), 7.84(s, 1H). | 388/390 | 106-108 | — |
| 1.193 | 1.48-1.50(d, 3H), 3.93(s, 3H), 4.02-4.10(ddd, 2H), 4.52-4.55(m, 1H), 6.67(s, 1H) 6.78-7.05 (t, 1H), 7.64(s, 2H), 7.88(s, 1H). | 543.8/545.7/549.8 | 122-124 | — |
| 1.194 (S)-enantiomere | — | — | — | 1.20 min; 346 |
| 1.221 | — | — | — | 1.32 min; 356 |
| 1.239 | 1.39-1.41(d, 3H, CH$_3$), 3.91(s, 3H, CH$_3$), 4.46-4.54(m, 2H, CH$_2$), 4.60-4.66(m, 1H, CH), 6.63(s, 1H, NH), 6.67-6.81(t, 1H, CHF$_2$), 7.85(d, 1H, Py-H), 7.90(s, 1H, pyrazole-H), 8.30(t, 1H, Py-H). | 413/415 | 115-118 | — |
| 1.565 | | | 88-90 | |
| 1.649 | | | 110-114 | |
| 1.650 | | | 113-116 | |
| 1.651 | | | 108-111 | |
| 2.218 | — | — | — | 2.00 min; 374 |
| 2.565 | | | 121-123 | |
| 2.649 | | | 130-132 | |
| 2.651 | | | resin | |
| 3.649 | | | 134-136 | |
| 4.565 | | | 109-110 | |
| 4.649 | | | 151-153 | |
| 5.565 | | 534 | resin | |
| 5.649 | | | 90-92 | |
| 5.651 | | | resin | |
| Z1.108 free base | — | 254.5/256.5/258.5 | waxy solid | — |
| Z1.166 (S)-enantiomere HCl salt | — | — | 190-193 | |
| Z1.190 free base | — | 220.1 | waxy solid | — |
| Z1.191 free base | — | 230/232 | waxy solid | — |
| Z1.193 free base | — | 389.8/391.8 | waxy solid | — |

Formulation Examples for Compounds of Formula I

Example F-1.1 to F-1.2

Emulsifiable Concentrates

| Components | F-1.1 | F-1.2 |
|---|---|---|
| compound of Tables 1 to 7 (1a to 7a) | 25% | 50% |
| calcium dodecylbenzenesulfonate | 5% | 6% |
| castor oil polyethylene glycol ether (36 mol ethylenoxy units) | 5% | — |
| tributylphenolpolyethylene glycol ether (30 mol ethylenoxy units) | — | 4% |
| cyclohexanone | — | 20% |
| xylene mixture | 65% | 20% |

Emulsions of any desired concentration can be prepared by diluting such concentrates with water.

Example F-2

Emulsifiable Concentrate

| Components | F-2 |
|---|---|
| compound of Tables 1 to 7 (1a to 7a) | 10% |
| octylphenolpolyethylene glycol ether (4 to 5 mol ethylenoxy units) | 3% |
| calcium dodecylbenzenesulfonate | 3% |
| castor oil polyglycol ether (36 mol ethylenoxy units) | 4% |
| cyclohexanone | 30% |
| xylene mixture | 50% |

Emulsions of any desired concentration can be prepared by diluting such concentrates with water.

Examples F-3.1 to F-3.4

Solutions

| Components | F-3.1 | F-3.2 | F-3.3 | F-3.4 |
|---|---|---|---|---|
| compound of Tables 1 to 7 (1a to 7a) | 80% | 10% | 5% | 95% |
| propylene glycol monomethyl ether | 20% | — | — | — |
| polyethylene glycol (relative molecular mass: 400 atomic mass units) | — | 70% | — | — |
| N-methylpyrrolid-2-one | — | 20% | — | — |
| epoxidised coconut oil | — | — | 1% | 5% |
| benzin (boiling range: 160-190°) | — | — | 94% | — |

The solutions are suitable for use in the form of microdrops.

Examples F-4.1 to F-4.4

Granulates

| Components | F-4.1 | F-4.2 | F-4.3 | F-4.4 |
|---|---|---|---|---|
| compound of Tables 1 to 7 (1a to 7a) | 5% | 10% | 8% | 21% |
| kaolin | 94% | — | 79% | 54% |
| highly dispersed silicic acid | 1% | — | 13% | 7% |
| attapulgite | — | 90% | — | 18% |

The novel compound is dissolved in dichloromethane, the solution is sprayed onto the carrier and the solvent is then removed by distillation under vacuum.

Examples F-5.1 and F-5.2

Dusts

| Components | F-5.1 | F-5.2 |
|---|---|---|
| compound of Tables 1 to 7 (1a to 7a) | 2% | 5% |
| highly dispersed silicic acid | 1% | 5% |
| talcum | 97% | — |
| kaolin | — | 90% |

Ready for use dusts are obtained by intimately mixing all components.

Examples F-6.1 to F-6.3

Wettable Powders

| Components | F-6.1 | F-6.2 | F-6.3 |
|---|---|---|---|
| compound of Tables 1 to 7 (1a to 7a) | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7 to 8 mol ethylenoxy units) | — | 2% | — |
| highly dispersed silicic acid | 5% | 10% | 10% |
| kaolin | 62% | 27% | — |

All components are mixed and the mixture is thoroughly ground in a suitable mill to give wettable powders which can be diluted with water to suspensions of any desired concentration.

Example F7

Flowable Concentrate for Seed Treatment

| | |
|---|---|
| compound of Tables 1 to 7 (1a to 7a) | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

BIOLOGICAL EXAMPLES

Fungicidal Actions

Example B-1

Action Against *Botrytis cinerea*—Fungal Growth Assay

Conidia of the fungus from cryogenic storage are directly mixed into nutrient broth (PDB potato dextrose broth). After placing a (DMSO) solution of the test compounds (0.002% active ingredient) into a microtiter plate (96-well format) the nutrient broth containing the fungal spores is added. The test plates are incubated at 24° C. and the inhibition of growth is measured photometrically after 3-4 days. The activity of a compound is expressed as fungal growth inhibition (0=no growth inhibition, ratings of 80% to 99% mean good to very good inhibition, 100%=complete inhibition).

Compounds 1.101, 1.166 and 1.193 show very good activity in this test ($\leqq$80% inhibition).

Compounds 1.221 and 1.239 show good activity in this test (50% inhibition).

Example B-2

Action Against *Mycosphaerella arachidis* (Early Leaf Spot of Groundnut; *Cercospora arachidicola* [Anamorph])—Fungal Growth Assay Conidia of the fungus from cryogenic storage are directly mixed into nutrient broth (PDB potato dextrose broth). After placing a (DMSO) solution of the test compounds (0.002% active ingredient) into a microtiter plate (96-well format) the nutrient broth containing the fungal spores is added. The test plates are incubated at 24° C. and the inhibition of growth is measured photometrically after 6-7 days. The activity of a compound is expressed as fungal growth inhibition (0=no growth inhibition, ratings of 80% to 99% mean good to very good inhibition, 100%=complete inhibition).

Compounds 1.101, 1.166 (S)-enantiomere, 1.166 (racemat), 1.193, 1.221 and 1.239 show very good activity in this test (≦30% inhibition).

Compounds 1.100, 1.102 and 1.103 show good activity in this test (≦50% inhibition).

Example B-3

Action Against *Septoria tritici*—Fungal Growth Assay

Conidia of the fungus from cryogenic storage are directly mixed into nutrient broth (PDB potato dextrose broth). After placing a (DMSO) solution of the test compounds (0.002% active ingredient) into a microtiter plate (96-well format) the nutrient broth containing the fungal spores is added. The test plates are incubated at 24° C. and the inhibition of growth is determined photometrically after 72 hrs. The activity of a compound is expressed as fungal growth inhibition (0=no growth inhibition, ratings of 80% to 99% mean good to very good inhibition, 100%=complete inhibition).

Compounds 1.099, 1.101, 1.103, 1.166 (S)-enantiomere, 1.166 (racemat), 1.193, 1.221 and 1.239 show very good activity in this test (≦80% inhibition).

Compound 1.102 shows good activity in this test (≦50% inhibition).

Example B-4

Action Against *Tapesia yallundae*—Fungal Growth Assay

Conidia of the fungus from cryogenic storage are directly mixed into nutrient broth (PDB potato dextrose broth). After placing a (DMSO) solution of the test compounds (0.002% active ingredient) into a microtiter plate (96-well format) the nutrient broth containing the fungal spores is added. The test plates are incubated at 24° C. and the inhibition of growth is measured photometrically after 6-7 days. The activity of a compound is expressed as fungal growth inhibition (0=no growth inhibition, ratings of 80% to 99% mean good to very good inhibition, 100%=complete inhibition).

Compounds 1.101 and 1.102 show very good activity in this test (≦80% inhibition).

Example B-5

Action Against *Monographella nivalis* (Anamorph: *Fusarium nivale, Microdochium nivale*; Snow Mould)—Fungal Growth Assay Conidia of the fungus from cryogenic storage are directly mixed into nutrient broth (PDB potato dextrose broth). After placing a DMSO-solution of the test compounds (0.002% active ingredient) into a microtiter plate (96-well format) the nutrient broth containing the fungal spores is added. The test plates are incubated at 24° C. and the inhibition of growth is measured photometrically after 72 hrs (0=no growth inhibition, ratings of 80% to 99% mean good to very good inhibition, 100%=complete inhibition).

Compounds 1.101, 1.102, 1.103, 1.166 (S)-enantiomere, 1.166 (racemat), 1.193 and 1.221 show very good activity in this test (≦30% inhibition).

Compounds 1.099 and 1.239 show good activity in this test (≦50% inhibition).

Example B-6

Action Against *Rhizoctonia solani*—Fungal Growth Assay

Mycelial fragments of a newly grown liquid culture of the fungus are directly mixed into nutrient broth (PDB potato dextrose broth). After placing a (DMSO) solution of the test compounds (0.002% active ingredient) into a microtiter plate (96-well format) the nutrient broth containing the fungal spores is added. The test plates are incubated at 24° C. and the inhibition of growth is measured photometrically after 3-4 days. The activity of a compound is expressed as fungal growth inhibition (0=no growth inhibition, ratings of 80% to 99% mean good to very good inhibition, 100%=complete inhibition).

Compounds 1.166 (S)-enantiomere, 1.166 (racemat) and 1.193 show very good activity in this test (≦80% inhibition).

Compound 1.101 shows good activity in this test (≦50% inhibition).

Example B-7

Action Against *Phythophthora infestans* (Late Blight) on Tomato

Tomato leaf disks are placed on water agar in multiwell plates (24-well format) and sprayed with test solutions (0.02% active ingredient). After drying, the leaf disks are inoculated with a spore suspension of the fungus. After appropriate incubation the activity of a compound is assessed 4 days after inoculation as preventive fungicidal activity.

Compounds 1.166 (S)-enantiomere and 1.166 (racemat) show good activity in this test (≦550% inhibition).

Example B-8

Action Against *Botrytis cinera* (Grey Mold) on Beans

Bean leaf disks are placed on agar in multiwell plates (24-well format) and sprayed with test solutions (0.02% active ingredient). After drying, the leaf disks are inoculated with a spore suspension of the fungus. After appropriate incubation the activity of a compound is assessed 3 days after inoculation as preventive fungicidal activity.

Compounds 1.099, 1.166 (S)-enantiomere, 1.166 (racemat), 1.193, 1.221 and 1.239 show very good activity in this test (≦80% inhibition).

Compound 1.101 shows good activity in this test (≦50% inhibition).

Example B-9

Action Against *Erysiphe graminis* F.Sp. Tritici (Wheat Powdery Mildew)

Wheat leaf segments are placed on agar in multiwell plates (24-well format) and sprayed with test solutions (0.02% active ingredient). After drying, the leaf disks are inoculated with a spore suspension of the fungus. After appropriate incubation the activity of a compound is assessed 7 days after inoculation as preventive fungicidal activity.

Compounds 1.166 (S)-enantiomere, 1.166 (racemat), 1.193, 1.221 and 1.239 show very good activity in this test (≦80% inhibition).

Compound 1.103 shows good activity in this test (≦50% inhibition).

Example B-10

Protective Action Against *Puccinia recondita* (Brown Rust) on Wheat

Wheat leaf segments are placed on agar in multiwell plates (24-well format) and sprayed with test solutions (0.02% active ingredient). After drying, the leaf disks are inoculated with a spore suspension of the fungus. After appropriate incubation the activity of a compound is assessed 8 days after inoculation as preventive fungicidal activity.

Compounds 1.166 (S)-enantiomere, 1.166 (racemat) and 1.193 show very good activity in this test (≦80% inhibition).

Compounds 1.101 and 1.221 show good activity in this test (≦50% inhibition).

Example B-11

Curative Action Against *Puccinia recondita* (Brown Rust) on Wheat

Wheat leaf segments are placed on agar in multiwell plates (24-well format) and inoculated with a spore suspension of the fungus. One day after inoculation the leaf segments are sprayed with test solutions (0.02% active ingredient). After appropriate incubation the activity of a compound is assessed 8 days after inoculation as curative fungicidal activity.

Compounds 1.166 (S)-enantiomere, 1.166 (racemat) and 1.193 show very good activity in this test (≦80% inhibition).

Example B-12

Action Against *Pyricularia oryzae* (Rice Blast) on Rice

Rice leaf segments are placed on agar in multiwell plates (24-well format) and sprayed with test solutions (0.02% active ingredient). After drying, the leaf disks are inoculated with a spore suspension of the fungus. After appropriate incubation the activity of a compound is assessed 5 days after inoculation as preventive fungicidal activity.

Compounds 1.166 (S)-enantiomere and 1.166 (racemat) show good activity in this test (≦50% inhibition).

Example B-13

Action Against *Leptosphaeria nodorum* (*Septoria nodorum*; Glume Blotch) on wheat Wheat leaf segments are placed on agar in multiwell plates (24-well format) and sprayed with test solutions (0.02% active ingredient). After drying, the leaf disks are inoculated with a spore suspension of the fungus. After appropriate incubation the activity of a compound is assessed 4 days after inoculation as preventive fungicidal activity.

Compounds 1.098, 1.101, 1.166 (S)-enantiomere, 1.166 (racemat), 1.193 and 1.221 show good activity in this test (≦50% inhibition).

Example B-14

Action Against *Pyrenophora teres* (Net Blotch) on Barley

Barley leaf segments are placed on agar in multiwell plates (24-well format) and sprayed with test solutions (0.02% active ingredient). After drying, the leaf disks are inoculated with a spore suspension of the fungus. After appropriate incubation the activity of a compound is assessed 4 days after inoculation as preventive fungicidal activity.

Compounds 1.100, 1.101, 1.103, 1.166 (S)-enantiomere, 1.166 (racemat), 1.193, 1.221 and 1.239 show very good activity in this test (≦80% inhibition).

Compounds 1.099 and 1.102 show good activity in this test (≦50% inhibition).

What is claimed is:

1. A compound of the formula I $$\underset{R_{15}}{\overset{O}{\underset{A}{\bigcup}}}\underset{N}{\overset{R_1}{\bigcup}}\underset{R_3}{\overset{R_2}{\bigcup}}\underset{R_4}{\overset{O}{\bigcup}}B, \qquad (I)$$

wherein
A is $A_1$ $$\underset{R_{17}}{\overset{R_{16}}{\underset{N}{\bigcup}}}\underset{N}{\overset{}{\bigcup}}R_{18}, \qquad (A_1)$$

in which
$R_{16}$ is $CF_2H$, $R_{17}$ is methyl, and $R_{18}$ is hydrogen;
$R_1$, $R_2$, $R_3$ and $R_4$ independently of each other are hydrogen, halogen, $C_1$-$C_6$alkyl, $C_1$-$C_6$halogenalkyl, $C_3$-$C_6$cycloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, $C_1$-$C_6$halogenalkoxy, $C_1$-$C_6$alkylthio or $C_1$-$C_6$halogenalkylthio;
or $R_1$ and $R_2$ together are a $C_2$-$C_5$alkylene group, which is unsubstituted or substituted by one or more $C_1$-$C_6$alkyl groups;
or $R_1$ and $R_3$ together are a $C_1$-$C_5$alkylene group, which is unsubstituted or substituted by one or more $C_1$-$C_6$alkyl groups;
or $R_3$ and $R_4$ together are a $C_2$-$C_5$alkylene group, which is unsubstituted or substituted by one or more $C_1$-$C_6$alkyl groups;
$R_{15}$ is hydrogen or $C_3$-$C_7$cycloalkyl;
B is $B_1$

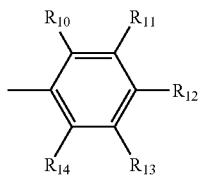

in which $R_{10}$, $R_{11}$, $R_{12}$, $R_{13}$ and $R_{14}$ each independently of each other stand for hydrogen, halogen, $C_1$-$C_6$alkoxy, —C(O)H, $C_1$-$C_6$-alkylcarbonyl, amino, $C_1$-$C_6$alkylamino, di-$C_1$-$C_6$alkyl-amino, $C_1$-$C_6$alkylcarbonylamino, $C_1$-$C_6$haloalkoxy, $C_1$-$C_6$haloalkylthio, cyano, nitro, —C($R^a$)=N(O$R^b$), —N=C($R^e$)—N($R^f$)$_2$, $C_1$-$C_6$alkyl, which is unsubstituted or substituted by one or more substituents $R_9$, $C_2$-$C_6$alkenyl, which is unsubstituted or substituted by one or more substituents $R_9$, $C_2$-$C_6$alkynyl, which is unsubstituted or substituted by one or more substituents $R_9$, $C_2$-$C_6$alkenyloxy, which is unsubstituted or substituted by one or more substituents $R_9$, $C_3$-$C_6$cycloalkyl, which is unsubstituted or substituted by one or more substituents $R_9$, $C_6$-$C_{14}$bicycloalkyl, which is unsubstituted or substituted by one or more substituents $R_9$, phenyl, which is unsubstituted or substituted b one or more substituents $R_9$, or phenyloxy, which is unsubstituted or substituted by one or more substituents $R_9$;

each $R_9$ is independently of each other halogen, nitro, $C_3$-$C_6$cycloalkyl, $C_1$-$C_6$alkoxy, $C_1$-$C_6$halogenalkoxy, $C_1$-$C_6$alkylthio, $C_1$-$C_6$halogenalkylthio, $C_3$-$C_6$alkenyloxy, $C_3$-$C_6$alkynyloxy, phenyl, halophenyl, tri-$C_1$-$C_6$alkyl-silyl or —C($R^c$)=N(O$R^d$);

each $R^a$, $R^c$, $R^e$ and $R^f$ is independently of each other hydrogen or $C_1$-$C_6$alkyl;

each $R^b$ and $R^d$ is independently of each other $C_1$-$C_6$alkyl;

provided that at least one of $R_{10}$, $R_{11}$, $R_{12}$, $R_{13}$ and $R_{14}$ is not hydrogen;

and tautomers/enantiomers of these compounds.

2. A compound of formula I according to claim 1, wherein $R_{15}$ is hydrogen.

3. A compound of formula I according to claim 1, wherein $R_1$ is methyl; and $R_2$, $R_3$ and $R_4$ are hydrogen.

4. A compound of formula I according to claim 1, wherein $B_1$ is $B_{1A}$

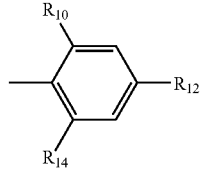

(B$_{1A}$)

in which $R_{10}$, $R_{12}$ and $R_{14}$ each independently of each other stands for hydrogen, halogen, $C_1$-$C_6$alkoxy, $C_1$-$C_6$haloalkoxy, $C_1$-$C_6$haloalkylthio, —C($R^a$)=N(O$R^b$), $C_1$-$C_6$alkyl, which is unsubstituted or substituted by one or more substituents $R_9$, $C_2$-$C_6$alkenyl, which is unsubstituted or substituted by one or more substituents $R_9$, $C_2$-$C_6$alkynyl, which is unsubstituted or substituted by one or more substituents $R_9$, phenyl, which is unsubstituted or substituted by one or more substituents $R_9$; phenyloxy, which is unsubstituted or substituted by one or more substituents $R_9$; and each $R_9$ is independently of each other halogen or $C_1$-$C_6$alkoxy; provided that at least one of $R_{10}$, $R_{12}$ and $R_{14}$ is not hydrogen.

5. A compound according to claim 4, in which $R_{10}$, $R_{12}$ and $R_{14}$ each independently of each other stands for hydrogen, halogen, $C_1$-$C_6$alkyl or $C_1$-$C_6$haloalkyl; provided that at least one of $R_{10}$, $R_{12}$ and $R_{14}$ is not hydrogen.

6. A method of controlling or preventing infestation of plants by phytopathogenic microorganisms, wherein a compound of formula I according to claim 1 is applied to the plants, to parts thereof or the locus thereof.

7. A composition for controlling and protecting against phytopathogenic microorganisms, comprising a compound of formula I according to claim 1 and an inert carrier.

* * * * *